United States Patent
Yasuda et al.

(10) Patent No.: US 9,447,447 B2
(45) Date of Patent: Sep. 20, 2016

(54) METHOD AND APPARATUS FOR TESTING CARDIOTOXICITY AND EVALUATING CARDIOMYOCYTES

(75) Inventors: Kenji Yasuda, Tokyo (JP); Tomoyuki Kaneko, Tokyo (JP); Fumimasa Nomura, Tokyo (JP)

(73) Assignees: National University Corporation Tokyo Medical and Dental University, Tokyo (JP); LSI Medience Corporation, Tokyo (JP)

( * ) Notice: Subject to any disclaimer, the term of this patent is extended or adjusted under 35 U.S.C. 154(b) by 311 days.

(21) Appl. No.: 13/876,992

(22) PCT Filed: Sep. 30, 2011

(86) PCT No.: PCT/JP2011/072618
§ 371 (c)(1),
(2), (4) Date: Mar. 29, 2013

(87) PCT Pub. No.: WO2012/043820
PCT Pub. Date: Apr. 5, 2012

(65) Prior Publication Data
US 2013/0230881 A1   Sep. 5, 2013

(30) Foreign Application Priority Data

Sep. 30, 2010  (JP) ................. 2010-222636
Oct. 19, 2010  (JP) ................. 2010-234498
Apr. 14, 2011  (JP) ................. 2011-090536

(51) Int. Cl.
*C12M 1/34*   (2006.01)
*C12Q 1/02*   (2006.01)
(Continued)

(52) U.S. Cl.
CPC ........... *C12Q 1/025* (2013.01); *G01N 33/5088* (2013.01); *C12M 35/02* (2013.01); *C12M 41/46* (2013.01); *C12M 41/48* (2013.01); *G01N 33/5061* (2013.01); *G01N 2800/32* (2013.01)

(58) Field of Classification Search
CPC ............. C12Q 1/025; G01N 33/5088; G01N 2800/32; G01N 33/4836; C12M 35/02; C12M 41/48
See application file for complete search history.

(56) References Cited

U.S. PATENT DOCUMENTS 8,877,457 B2 * 11/2014 Yasuda et al. .................. 435/29
2004/0067482 A1   4/2004 Yasuda et al.
(Continued)

FOREIGN PATENT DOCUMENTS

JP   2002-153260 A   5/2002
JP   2006-094703 A   4/2006
(Continued)

OTHER PUBLICATIONS

Brennan et al., "Do Existing Measures of Pointcare Plot Geometry Reflect Nonlinear Features of Heart Rate Variability?" IEEE Transactions on Biomedical Engineering, Nov. 2001, 48(11):1342-1347.
(Continued)

*Primary Examiner* — William H Beisner
(74) *Attorney, Agent, or Firm* — Foley & Lardner LLP

(57) ABSTRACT

In the present invention, a cardiomyocyte cluster is disposed on a transparent substrate, and the quality of the cardiomyocytes is evaluated from the response of the cells to a forced pulsation stimulus applied to the cardiomyocytes. The cardiomyocyte cluster is disposed on the transparent substrate, and is exposed to the flow of a liquid containing an agent in a manner so that the agent acts on the cells, which configure a network. The extent of cardiac toxicity resulting from the agent is evaluated from measuring the fluctuations obtained from a comparison of adjacent cardiomyocytes of the network.

16 Claims, 47 Drawing Sheets

(51) Int. Cl.
     *C12M 1/42*  (2006.01)
     *C12M 1/36*  (2006.01)
     *G01N 33/50* (2006.01)

(56) References Cited

U.S. PATENT DOCUMENTS

| | | | |
|---|---|---|---|
| 2007/0059763 A1 | 3/2007 | Okano et al. | |
| 2010/0178692 A1* | 7/2010 | Yasuda et al. | 435/288.7 |
| 2010/0304423 A1 | 12/2010 | Asai et al. | |
| 2011/0262958 A1 | 10/2011 | Yasuda et al. | |

FOREIGN PATENT DOCUMENTS

| | | |
|---|---|---|
| JP | 2010-130966 A | 6/2010 |
| WO | WO 2009/038079 A1 | 3/2009 |
| WO | WO 2010064700 A1 * | 6/2010 |

OTHER PUBLICATIONS

Kanters et al., "Lack of Evidence for Low-Dimensional Chaos in Heart Rate Variability," J. Cardiovasc. Electrophysiol., Jul. 1994, 5:591-601.

Saito et al., "Drug discovery and screening business using ES cells," Gekkan Medical Science Digest, 2007, 33(14):33(1272)-36(1275), with English translation, 7 pages.

Storella et al., "Approximate Entropy and Point Correlation Dimension of Heart Rate Variability in Healthy Subjects," Integrative Physiology and Behavioral Science, Oct.-Dec. 1998, 33(4):315-320.

Yasuda, Kenji, "On-chip cell culture and analysis system using precision processing technology," Oyo Butsuri, 2005, 74(7):890-895, with English translation, 12 pages.

Mitsuyasu Tabo thesis, "Studies of in vivo drug-induced QT interval prolongation in early-stage drug development," available online Mar. 25, 2010, Hokkaido University Collection of Scholarly and Academic Papers, http://hdl.handle.net/2115/42814, 77 pages.

Asai, Yasuyuki, "QTempo: An assay to identify cardiotoxicity using stem cell derived beating cardiomyocytes," Igaku No Ayumi, Jan. 9, 2010, 232(2):117-122, with English translation, 14 pages.

Braam et al., "Prediction of drug-induced cardiotoxicity using human embryonic stem cell-derived cardiomyocotes," Stem Cell Research, Mar. 2010, 4(2):107-116.

Horie et al., "Possibility of use of iPS Cells in Diagnosis and Treatment of Hereditary Arrhythmia," Saishin Igaku, Sep. 25, 2010, 65(Sep. extra edition):2095-2101, with English translation, 9 pages.

* cited by examiner (a) Pulse of cell population (b) Pulse of target cell (normal state)

(c) Pulse of target cell (on-drug state)

(a) Changes in volume of cell due to pulsation of cell population (b) Changes in volume of cell due to pulsation of target cell (normal state)

(c) Changes in volume of cell due to pulsation of target cell (on-drug state)

(a) Changes in extracellular potentials of target cell (normal state)

(b) Changes in extracellular potentials of target cell (on-drug state)

(a)

Convert FPD data into Poincare plots (b)

(a)

Number and arrangement of cells under control (b)

100 μm (a)

Cell population having a certain width that allows selection of conduction pathways (b)

Chamber
Length: 450 μm
Width: about 50 μm

Total: 50 cells
Myocyte: 32 cells
Fibroblast: 18 cells (c)

Blue: Nuclear
Green: Mitochondria (Cardiomyocyte)

6 Myocytes & 2 Fibroblasts in yellow box (a)

(b)

(a)

(b)

(c)

(a)

(b)

$$STV = \frac{\sum_{n=1}^{k} |(FPD_{n+1} - FPD_{mean}) - (FPD_n - FPD_{mean})|}{k \times \sqrt{2}}$$

$$= \frac{\sum_{n=1}^{k} |FPD_{n+1} - FPD_n|}{k \times \sqrt{2}} \quad \cdots \text{(Equation 1)}$$

(b)

$$LTV = \frac{\sum_{n=1}^{k} |(FPD_{n+1} - FPD_{mean}) + (FPD_n - FPD_{mean})|}{k \times \sqrt{2}}$$

$$= \frac{\sum_{n=1}^{k} |FPD_{n+1} + FPD_n - 2FPD_{mean}|}{k \times \sqrt{2}} \quad \cdots \text{(Equation 2)}$$

Table. 1 Heart rate correction of beating frequency, field potential duration

| | Beating Frequency | | | | FPD | | | FPDc | | |
|---|---|---|---|---|---|---|---|---|---|---|
| | Average (Hz) | S.D. (Hz) | C.V. (%) | Spike No. | Average (ms) | S.D. (ms) | C.V. (%) | Average (ms) | S.D. (ms) | C.V. (%) |
| 0.4 Hz (ctrl) | 0.37 | 0.01 | 1.5 | 110 | 795.3 | 13.9 | 1.7 | 536.7 | 9.7 | 1.8 |
| 0.5 Hz | 0.50 | 0.00 | 0.0 | 94 | 675.6 | 6.6 | 1.0 | 513.7 | 5.0 | 1.0 |
| 0.6 Hz | 0.60 | 0.00 | 0.0 | 142 | 638.5 | 7.5 | 1.2 | 521.8 | 6.1 | 1.2 |
| 0.8 Hz | 0.75 | 0.00 | 0.0 | 189 | 613.7 | 8.6 | 1.4 | 547.8 | 7.7 | 1.4 |
| 1.3 Hz | 1.28 | 0.00 | 0.0 | 253 | 489.4 | 11.5 | 2.4 | 540.2 | 12.7 | 2.4 |
| 1.8 Hz | 1.78 | 0.00 | 0.0 | 306 | 431.2 | 9.1 | 2.1 | 542.8 | 11.4 | 2.1 |

A. Core of the system

B. MEA Chip 2 cm

C. hES CM on MEA Chip

100um

METHOD AND APPARATUS FOR TESTING CARDIOTOXICITY AND EVALUATING CARDIOMYOCYTES

CROSS-REFERENCE TO RELATED APPLICATIONS

This application is a National Stage application of PCT/JP2011/072618, filed Sep. 30, 2011, which claims priority from Japanese application nos. JP 2010-222636, filed Sep. 30, 2010, JP 2010-234498, filed Oct. 19, 2010, and JP 2011-090536, filed Apr. 14, 2011.

TECHNICAL FIELD

The present invention relates to a method and an apparatus for testing myocardial toxicity and evaluating myocardial cells.

BACKGROUND ART

Bio-assays have been widely used to observe changes in the state of cells, the responsiveness of the cells to agents, and the like. In conventional bioassays, in general, cultured cells have been often used. In such systems, assays are performed using a plurality of cells, and an average of the values of a cell population has been measured as if it represented the characteristics of a single cell.

However, in fact, it is rare that there are cells whose cell cycle is synchronized in the cell population, and each cell synthesizes proteins in a different manner. Therefore, fluctuation is always the problem when analyzing the results of the response of the cells to a stimulus.

In other words, since the fluctuations of responses of the reaction mechanism of a cell itself are universally present, one can always only obtain an average of the responses. To solve this problem, there have been developed methodologies, such as synchronized culturing. However, to use a group of cells which are in the same stage, one must always continue to supply such cells, and therefore has become an obstacle to broad-based application of the bioassay.

In addition, in reality it has been difficult to decide on the fluctuation because there are two types of stimulation (signals) to cells: one is given by the amount of signal substances, nutrition, dissolved gas contained in the solution surrounding the cell, and the other is given by the physical contact and cell-to-cell interaction with other cells.

Difficulties in the physical contact and the cell-to-cell interaction problems of the cells can be resolved to some extent by performing bioassays on a cell mass such as tissue fragments. However, in such cases, unlike cultured cells, it is not always possible to obtain a cell mass with a homogeneous feature. Therefore, there is a problem that the resulting data can vary, and the information is buried in the population.

To enable measurement using an information processing model in which each cell in the cell population is a minimum structural unit, the inventors of the present application have proposed a microarray for aggregated cells (bioassay chip) comprising a plurality of cell culture compartments for confining a cell in the inside of specific spatial arrangement; a groove or a tunnel linking between adjacent compartments, wherein a cell cannot pass through the groove or the tunnel; and a plurality of electrode patterns for measuring a change in electric potential of the cell arranged in the groove or the tunnel or the cell culture compartment as shown in JP 2006-94703 (Patent Document 1).

In addition, a method for electrocardiogram analysis has been proposed for the evaluation of the electrocardiogram obtained by reflecting complex cardiac functions by utilizing a method typically used for measuring non-linear dynamics. For example, a Poincare plotting method has been the most commonly used for the analysis of electrocardiogram (Non-Patent Document 1). A point in the plot refers to information of two adjacent pulsation data, in which, for example, a rate of pulsation at one time point is indicated in the X axis and a rate of pulsation at a previous time point is indicated in the Y axis. Thus, the fluctuation in the cardiac pulsation is estimated by quantifying the distribution of the points on the graph. Other methods for measuring the fluctuation of the cardiac pulsation include a correlation dimension method, a nonlinear predictability method (Non-Patent Document 2), an approximate entropy method (Non-Patent Document 3), and the like.

BACKGROUND ART DOCUMENTS

Patent Document

[Patent Document 1] Japanese Laid-open Patent Publication No. 2006-94703

Non-Patent Document

[Non-Patent Document 1] Brennan M, Palaniswami M, Kamen P. Do existing measures of Poincare plot geometry reflect non-linear features of heart rate variability? Biomedical Engineering, IEEE Transactions on, Proc. IEEE Transactions on Biomedical Engineering, 2001, 48, 1342-1347

[Non-Patent Document 2] Kanters J K, Holstein-Rathlou N H, Agner E (1994) "Lack of evidence for low-dimensional chaos in heart rate variability" Journal of Cardiovascular Electrophysiology 5 (7): 591-601.PMID 7987529.

[Non-Patent Document 3] Storella R J, Wood H W, Mills K M et al (1994) "Approximate entropy and point correlation dimension of heart rate variability in healthy subjects" Integrative Physiological & Behavioral Science 33 (4): 315-20. PMID 10333974.

SUMMARY OF THE INVENTION

Problem to be Solved by the Invention

In conventional bioassays, cells were treated as a tissue fragment or as a single cell as in cultured cells. As mentioned in the above background art section, when the number of cells is excessive, information collected is averaged, and there is a problem that responses to agents cannot be obtained accurately. When the cells are used as a single cell, the cell is used in a separated independent state instead of cells in natural multi-cellular tissues. Consequently, the effect of the interaction between cells is not exhibited. Therefore, there is still a problem in obtaining an accurate agent response, that is, a bioassay data.

There is a need for the development of an apparatus or a system that enables accurate measurement of the membrane potential or the cell morphology in a unit of a single cell as a measure of propagation of pulsation from mutually adjacent fibroblasts or cardiomyocytes, and the accurate measurement of the membrane potential or the cell morphology in a unit of a single cell as a measure of the toxicity of agents on cardiac muscle cells.

Use in regenerative medicine or agent screening requires that the functional aspects of cardiomyocytes which are differentiated from human stem cells including human iPS cells or human ES cells must be evaluated quantitatively to ascertain whether the qualitative features of the cardiomyocytes are the same as cardiomyocytes in the human heart cells.

Means for Solving the Problem

In view of the above problems, the present invention provides an apparatus and method as described below.

(1) A quality evaluation apparatus for cells, comprising:
a substrate;
a plurality of stably pulsating subject cardiomyocytes or a cell population comprising the subject cells placed on the substrate;
a wall formed on the substrate to surround the periphery of the cell population and to fill a cell culture medium;
a culture-medium supply/drain channel for supplying and/or draining the cell culture medium to and/or from the area surrounded by the wall;
a microelectrode on which a single cell or a local portion of the cell population is placed;
a reference electrode provided in the area which is to be filled with the cell culture medium and is surrounded by the wall;
a potential-measuring means for measuring membrane potential of the cell that is placed on the microelectrode using lead wires which are respectively connected to each of the microelectrodes and a lead wire which is connected to the reference electrode; and
a control/recording means for controlling an electrical stimulation delivered to the microelectrode and for recording data of the potential measured by the potential measuring means,
wherein the quality evaluation apparatus is capable of varying the electrical stimulation to be sent to the microelectrode at an interval in a stepwise fashion, and of
(i) determining whether the cardiomyocytes or the cell population respond to forced pulsatile stimulation by the electrical stimulation at the same interval as the forced pulsatile stimulation; measuring as to how the response corresponds to the range of frequency of the forced pulsatile stimulation; and judging that one of the sufficient conditions for a healthy cardiomyocyte is met when it is observed that the pulsation of the cells can follow the forced pulsatile stimulation, and
(ii) judging that one of the sufficient conditions for a healthy cardiomyocyte is met when it is observed that the variation of FPD in response to the forced pulsatile stimulation is between the $FPD/(RR)^{1/3}$ and $FPD/(RR)^{1/2}$ within the frequency range in which the pulsation of the cell can follow the forced pulsatile stimulation intervals (RR) by the electrical stimulation.

(2) A quality evaluation apparatus for cells, comprising:
a substrate;
a cardiomyocyte population holding area comprising a plurality of cell holding units placed on the substrate to hold stably pulsating subject cardiomyocytes;
a spatial area defined by a surface of the substrate and a wall formed on the substrate and surrounding the periphery of the cardiomyocyte population holding area to be filled with a cell culture medium;
a culture-medium supply/drain channel for supplying and/or draining the cell culture medium to and/or from the area surrounded by the wall;
a microelectrode which is placed on the transparent substrate and on which the cardiomyocyte is placed in one or a part of the cell holding units in the cardiomyocyte population holding area;
a reference electrode provided in the spatial area for filling with the cell culture medium;
a potential-measuring means for measuring membrane potential of the cell that is placed on the microelectrode using lead wires which are connected respectively to each of the microelectrodes and a lead wire which is connected to the reference electrode; and
a control/recording means for controlling an electrical stimulation delivered to the microelectrode and for recording data of the potential measured by the potential measuring means,
wherein the quality evaluation apparatus is capable of varying the electrical stimulation to be sent to the microelectrode at an interval in a stepwise fashion, and of
(i) determining whether the cardiomyocytes or the cell population respond to forced pulsatile stimulation by the electrical stimulation at the same interval as the forced pulsatile stimulation; measuring the response in terms of the range of frequency of the forced pulsatile stimulation; and judging that one of the sufficient conditions for a healthy cardiomyocyte is met when it is observed that the pulsation of the cells can follow the forced pulsatile stimulation, and
(ii) judging that one of the sufficient conditions for a healthy cardiomyocyte is met when it is observed that the variation of FPD in response to the forced pulsatile stimulation is between the $FPD/(RR)^{1/3}$ and $FPD/(RR)^{1/2}$ within the frequency range in which the pulsation of the cell can follow the forced pulsatile stimulation intervals (RR) by the electrical stimulation.

(3) A quality evaluation method for cells comprising using a cell quality evaluation apparatus, wherein the apparatus comprising:
a substrate;
a plurality of stably pulsating subject cardiomyocytes or a cell population comprising the subject cells placed on the substrate;
a wall formed on the substrate to surround the periphery of the cell population and to fill a cell culture medium;
a culture-medium supply/drain channel for supplying and/or discharging the cell culture medium to and/or from the area surrounded by the wall;
a microelectrode on which a single cell of the cell population or a local portion of the cell population is placed;
a reference electrode provided in the area which is to be filled with the cell culture medium and is surrounded by the wall;
a potential-measuring means for measuring cell potential of the cell that is placed on the microelectrode using lead wires which are respectively connected to each of the microelectrodes and a lead wire which is connected to the reference electrode; and
a control/recording means for controlling an electrical stimulation delivered to the microelectrode and for recording data of the potential measured by the potential measuring means; and
the method further comprising:
varying the electrical stimulation to be sent to the microelectrode at an interval in a stepwise fashion, and
(i) determining whether the cardiomyocytes or the cell population respond to forced pulsatile stimulation by the electrical stimulation at the same interval as the forced pulsatile stimulation; measuring the response in terms of the range of frequency of the forced pulsatile stimulation; and judging that one of the sufficient conditions for a healthy cardiomyocyte is met when it is observed that the pulsation of the cells can follow the forced pulsatile stimulation, and (ii) judging that one of the sufficient conditions for a healthy cardiomyocyte is met when it is observed that the variation of FPD in response to the forced pulsatile stimulation is between the $FPD/(RR)^{1/3}$ and $FPD/(RR)^{1/2}$ within the frequency range in which the pulsation of the cell can follow the forced pulsatile stimulation intervals (RR) by the electrical stimulation.

(4) A quality evaluation method for cells comprising using a cell quality evaluation apparatus, wherein the apparatus comprising:

a substrate;

a cardiomyocyte population holding area comprising a plurality of cell holding units placed on the substrate to hold stably pulsating subject cardiomyocytes;

a spatial area defined by a surface of the substrate and a wall formed on the substrate and surrounding the periphery of the cardiomyocyte population holding area to be filled with a cell culture medium;

a culture-medium supply/drain channel for supplying and/or draining the cell culture medium to and/or from the area surrounded by the wall;

a microelectrode which is placed on the transparent substrate and on which the cardiomyocyte is placed in one or a part of the cell holding units in the cardiomyocyte population holding area;

a reference electrode provided in the area which is to be filled with the cell culture medium and is surrounded by the wall;

a potential-measuring means for measuring membrane potential of the cell that is placed on the microelectrode using lead wires which are connected respectively to each of the microelectrodes and a lead wire which is connected to the reference electrode; and a control/recording means for controlling an electrical stimulation delivered to the microelectrode and for recording data of the potential measured by the potential measuring means; and the method further comprising:

varying the electrical stimulation to be sent to the microelectrode at an interval in a stepwise fashion, and (i) determining whether the cardiomyocytes or the cell population respond to forced pulsatile stimulation by the electrical stimulation at the same interval as the forced pulsatile stimulation; measuring the response in terms of the range of frequency of the forced pulsatile stimulation; and judging that one of the sufficient conditions for a healthy cardiomyocyte is met when it is observed that the pulsation of the cells can follow the forced pulsatile stimulation, and (ii) judging that one of the sufficient conditions for a healthy cardiomyocyte is met when it is observed that the variation of FPD in response to the forced pulsatile stimulation is between the $FPD/(RR)^{1/3}$ and $FPD/(RR)^{1/2}$ within the frequency range in which the pulsation of the cell can follow the forced pulsatile stimulation intervals (RR) by the electrical stimulation.

The present invention also provides a cardiotoxicity testing apparatus, a cardiotoxicity testing tip, and a cardiotoxicity testing method as follows:

[1] A cardiotoxicity testing apparatus comprising:

a transparent substrate;

a cell population comprising a plurality of stably pulsating cardiomyocytes placed on the transparent substrate;

a cellular network comprising a plurality of cardiomyocytes and fibroblasts disposed on the transparent substrate, and arranged in series to transmit the pulsation of the cell population in conjunction with the cell population;

a wall formed on the transparent substrate and surrounding the periphery of the cell population and the cellular network to hold a cell culture medium;

a culture-medium supply/drain channel for supplying and/or draining the cell culture medium to and/or from the area surrounded by the wall;

an agent delivery channel for introducing an agent acting on the cells to the cell culture medium;

a microelectrode on which a single cell of the cell population or a local portion of the cell population is placed;

a microelectrode on which each individual cell of the cellular network is placed;

a reference electrode provided in the area to hold the cell culture medium that is surrounded by the wall;

a potential-measuring means for measuring the membrane potential of the cell that is placed on the microelectrode using lead wires which are connected respectively to each of the microelectrodes and a lead wire which is connected to the reference electrode; and a control/recording means for controlling an electrical stimulation delivered to the microelectrode and for recording data of the potential measured by the potential measuring means.

[2] A cardiotoxicity testing apparatus comprising:

a transparent substrate;

a cardiomyocyte population-holding area comprising a plurality of cell holding units ($CH_G$) for holding stably pulsating cardiomyocytes disposed on the transparent substrate;

a cellular-network area for holding cells that transmit the pulsation of the cardiomyocyte population in conjunction with one cell of the cell holding unit, comprising a plurality of cell holding units ($CH_n$) arranged in series, wherein the cell holding unit ($CH_n$) holds the cardiomyocytes or the fibroblasts;

a spatial area for being filled with a cell culture medium, wherein the spatial area is defined by a surface of the transparent substrate and a wall which is formed on the surface of the transparent substrate and surrounding the periphery of the cardiomyocyte population-holding area and the cellular-network area;

a culture-medium supply/drain channel for supplying and/or draining the cell culture medium to and/or from the spatial area;

an agent delivery channel for introducing an agent acting on the cells to the cell culture medium;

a microelectrode, provided on the transparent substrate, for placing thereon the cardiomyocyte in one or a part of the cell holding units ($CH_G$) in the cardiomyocyte population-holding area;

a plurality of microelectrodes, provided on the transparent substrate, for placing thereon individual cells at a plurality of cell holding units ($CH_n$) of the cellular-network area;

a reference electrode provided in the spatial area for being filled with a cell culture medium;

a potential-measuring means for measuring the membrane potential of the cell that is placed on the microelectrodes using a lead wire which is connected to the reference electrode and lead wires which are connected respectively to each of the microelectrodes; and a control/recording means for controlling an electrical stimulation delivered to the microelectrode and for recording data of the potential measured by the potential-measuring means.

[3] The cardiotoxicity testing apparatus according to [1] or [2] above, wherein the apparatus is configured to enable provision of forced-pulsatile stimulation at uniform intervals to the cells that are placed on the microelectrodes via at least one of the microelectrodes for placing the cells in the cellular network.

[4] The cardiotoxicity testing apparatus according to any one of [1] to [3] above, wherein the apparatus is configured to measure the magnitude of fluctuation of a waveform of a field potential of the pulsating cardiomyocytes collected from each of the microelectrodes on which the cells are respectively mounted through comparison of the adjacent pulsation signals.

[5] The cardiotoxicity testing apparatus according to any one of [1] to [3] above, wherein the apparatus is configured to measure the magnitude of fluctuation of elapsed time (field potential duration) between the peak position of the outflow of sodium ions and the peak position of the outflow of potassium ions from the cells by comparison of adjacent pulsation signals in a waveform of a field potential.

[6] The cardiotoxicity testing apparatus according to any one of [1] to [3] above, wherein the apparatus is configured to measure the magnitude of fluctuations of a field potential waveform of cardiopulsation collected from each of the microelectrodes on which the cells are respectively placed by a comparison of adjacent pulsation signals in relation to the fluctuation of time or the speed of transmission of the pulsation from the area in which the pulsation of the cell of the cellular network generates to an observation electrode.

[7] The cardiotoxicity testing apparatus according to any one of [1] to [3] above, wherein the apparatus is configured to measure the membrane potential by differentiating each field potential waveform of cardiopulsation collected from each of the microelectrodes on which the cells are respectively placed.

[8] The cardiotoxicity testing apparatus according to any one of [1] to [3] above, wherein the apparatus is configured to measure the degree of disturbance of the transmission of the pulsation of the entire cell population to for a comparison with the electrocardiogram data by overlapping the field potential waveforms of the pulsating cardiomyocytes collected from each of the electrodes on which the cells are respectively placed to generate a composite field potential waveform.

[9] The cardiotoxicity testing apparatus according to any one of [1] to [3] above, wherein the apparatus is configured to analyze the amount of current supplied by an electric control mechanism using a feedback control mechanism to maintain a constant potential of the microelectrode on which the cell is placed.

[10] The cardiotoxicity testing apparatus according to any one of [1] to [3] above, wherein the apparatus is configured to start measurements after at least 30 seconds from the start of the periodic forced pulsatile stimulation on the cell.

[11] The cardiotoxicity testing apparatus according to any one of [1] to [10] above, further comprising an optical system and an optical camera for optically measuring the state of the cells placed on the transparent substrate, wherein image data acquired by the optical camera is recorded on the control/recording means.

[12] The cardiotoxicity testing apparatus according to [2] to [11] above, wherein each of the cell holding units ($CH_G$, $CH_n$) is defined as a space surrounded by a non-cell-adherent wall arranged on the transparent substrate, and wherein the wall has one or more gaps that do not allow the cell to pass through.

[13] The cardiotoxicity testing apparatus according to any one of [2] to [12] above, comprising a barrier provided between the cardiomyocyte population-holding area and the cellular network area, wherein the barrier restricts a flow of the cell culture medium, and has an opening that allows a cell housed in one of the plurality of the cell holding units ($CH_G$) in the cardiomyocyte population-holding area and a cell housed in the end unit of the cell holding units ($CH_n$) of the cellular network area to associate with each other.

[14] A cardiotoxicity testing apparatus comprising:
a transparent substrate;
a cardiomyocyte population-holding area comprising a plurality of cell holding units ($CH_G$) arranged on the transparent substrate;
a cellular network area comprising a plurality of cell holding units ($CH_n$) which are arranged in series to transmit the pulsation of the cardiomyocyte population in conjunction with one cell of the cell holding units ($CH_G$) of the cardiomyocyte population-holding area, wherein the cell holding units ($CH_n$) hold cardiomyocytes or fibroblasts;
a spatial area for being filled with a cell culture medium, wherein the spatial area is defined by a surface of the transparent substrate and a wall which is formed on the surface of the transparent substrate and surrounding the cardiomyocyte population-holding area and the cellular network area;
a supply/drain means for supplying and/or draining the culture medium in and/or from the spatial area surrounded by the wall;
an agent delivery means for introducing an agent acting on the cells to the cell culture medium;
a microelectrode provided on the transparent substrate and having thereon a cardiomyocyte in one of the cell holding units ($CH_G$) in the cardiomyocyte population-holding area;
a plurality of microelectrodes provided on the transparent substrate and having thereon a cardiomyocyte or a fibroblast in each of the plurality of the cell holding units ($CH_n$) in the cellular network area;
a reference electrode provided in the area surrounded by the wall;
a means for measuring and recording potentials of the cells placed on the microelectrodes by using lead wires connected to the respective microelectrodes and a lead wire connected to the reference electrode;
a stage on which the transparent substrate is placed and which is driven in the X-Y direction; and
means for optically measuring the state of the cells on the transparent substrate that is placed on the stage.

[15] A cardiotoxicity testing chip comprising:
a transparent substrate;
a cardiomyocyte population-holding area comprising a plurality of cell holding units ($CH_G$) provided on the transparent substrate for holding cardiomyocytes;
a cellular network area comprising a plurality of cell holding units ($CH_n$) which are arranged in series to transmit the pulsation of the cardiomyocyte population in conjunction with one cell of the cell holding units ($CH_G$), wherein the cell holding units ($CH_n$) hold cardiomyocytes or fibroblasts;
an area for being filled with a cell culture medium, wherein the area is defined by a surface of the transparent substrate and a wall which is formed on the surface of the transparent substrate and surrounding the cardiomyocyte population-holding area and the cellular network area;

a microelectrode provided on the transparent substrate and having thereon a cardiomyocyte in one of the cell holding units ($CH_G$) in the cardiomyocyte population-holding area;

a plurality of microelectrodes provided on the transparent substrate and each having thereon a cardiomyocyte or a fibroblast in each of the plurality of the cell holding units ($CH_n$) in the cell communication channel;

a reference electrode provided within the area surrounded by the wall; and lead wires connected to the respective microelectrodes and a lead wire connected to the reference electrode.

[16] A method for testing cardiotoxicity using the cardiotoxicity testing apparatus according to any one of [1] to [14] above or the cardiotoxicity testing chip according to [15] above, comprising:

examining cardiotoxicity of an agent that acts on cardiomyocytes by assessing whether or not the rate at which the pulsation produced by the population of the cardiomyocytes propagates in the cellular network area is delayed when the agent acting on the cells is introduced into the culture medium.

[17] A method for testing cardiotoxicity of an agent that acts on the cardiomyocytes, comprising:

assessing whether or not the rate at which the pulsation produced by the population of the cardiomyocytes propagates in the cellular network area is delayed when an agent acting on the cells is added to the culture medium using the cardiomyocyte toxicity testing apparatus according to [1] or [2] above;

wherein the method further comprising at least one of the following steps:

(i) providing forced pulsatile stimulation at regular intervals to a cell, wherein the cell is placed on at least one of the microelectrodes for placing the cells of the cellular network;

(ii) measuring the magnitude of fluctuation of a field potential waveform of the cardiopulsation collected from each microelectrode on which the cell is placed by comparison of adjacent pulsation signals;

(iii) measuring the magnitude of fluctuation of an elapsed time (field potential duration) between a peak position of an outflow of potassium ions from the cell and a peak position of an outflow of sodium ions from the cell by comparison of the adjacent pulsation signals in the waveform of the field potential;

(iv) measuring the magnitude of fluctuations of a field potential waveform of the cardiopulsation collected from each microelectrode on which the cell is placed by comparison of adjacent pulsation signals with respect to fluctuations in time or the speed of transmission of the pulsation that transmits from the area in which the pulsation of the cell of the cellular network generates to the observation electrode;

(v) measuring a membrane potential by differentiating each field potential waveform of the myocardial pulsation collected from each microelectrode on which the cell is placed;

(vi) measuring the degree of disturbance of transmission of the pulsation of an entire cell population for a comparison with to electrocardiogram data by overlapping field potential waveforms of the pulsating cardiomyocytes collected from each of the electrodes on which the cells are placed to generate a composite field potential waveform;

(vii) analyzing an amount of current supplied by an electric control mechanism using a feedback control mechanism to maintain a constant potential of the microelectrode on which the cell is placed; and (viii) starting measurements after at least 30 seconds from the start of the periodic forced pulsatile stimulation on the cell.

[18] The cardiotoxicity testing apparatus according to any one of [1] to [14] above, further comprising a reference electrode for noise cancellation, wherein the reference electrode is placed near the microelectrode.

[19] The cardiotoxicity testing apparatus according to [18], wherein the microelectrode comprises a stimulation electrode and a measurement electrode.

[20] The cardiotoxicity testing apparatus according to [19], comprising:

a mechanism for continuously introducing an agent solution from the bottom of the cardiomyocyte culturing area thereto, and draining from the upper surface of the solution;

a mechanism for monitoring and maintaining the temperature of the agent solution at an appropriate temperature; and a tube having an area that is optically transparent for measuring the concentration of the agent solution that is introduced, wherein the apparatus allows quantitative spectrophotometric measuring of the absorption in the wavelength range of 280 nanometers to 800 nanometers.

[21] The cardiotoxicity testing apparatus according to any one of [1] to [14], and [18] to [20] above, wherein the microelectrode is transparent.

[22] The cardiotoxicity testing apparatus according to [21] above, further comprising a metal layer provided on the wiring of the transparent electrode that is disposed in an area other than the area for observation by an optical system to reduce the resistance of microelectrodes.

[23] The cardiotoxicity testing apparatus according to any one of [1] to [14], and [18] to [22] above, wherein a plurality of the cultured cardiomyocytes are arranged linearly on the substrate to form a cardiomyocyte network, and an electrode is arranged to stimulate locally at an endpoint of the linear cardiomyocyte network.

[24] The cardiotoxicity testing apparatus according to [23] above, further comprising a linear measurement electrode on which a majority of the myocardial cells in the linear myocardial-cellyocyte network can be disposed.

[25] The cardiotoxicity testing apparatus according to any one of [1] to [14], and [18] to [22] above, wherein a plurality of the cultured cardiomyocytes are arranged in an annular fashion on the substrate to form an annular network, and a portion of the annular network is cut-out and an electrode is arranged at the cut-out point for local stimulation.

[26] The cardiotoxicity testing apparatus according to [25] above, further comprising one ring-shaped measurement electrode on which a majority of the cardiomyocytes in the ring-like cardiomyocyte network can be disposed.

[27] A method for testing cardiotoxicity using the cardiotoxicity testing apparatus according to any [1] to [26] above, comprising:

examining cardiotoxicity of an agent that acts on cardiomyocytes by assessing whether or not the rate at which the pulsation produced by the population of the cardiomyocytes propagates in the cellular network area is delayed when the agent acting on the cells is introduced into the culture medium.

[28] A method for testing cardiotoxicity of an agent that acts on the cardiomyocytes using the cardiotoxicity testing apparatus according to any one of [1] to [14], and [18] to [26] above, comprising:

assessing whether or not the rate at which the pulsation produced by the population of the cardiomyocytes propagates in the cellular network area is delayed when the agent acting on the cells is introduced into the culture medium;

wherein the method further comprising at least one of the following steps:

(i) providing forced pulsatile stimulation at uniform intervals to a cell, wherein the cell is placed on at least one of the microelectrodes for placing the cells of the cellular network;

(ii) measuring the magnitude of fluctuation of a field potential waveform of the cardiopulsation collected from each microelectrode on which the cell is placed by comparison of adjacent pulsation signals;

(iii) measuring the magnitude of fluctuation of an elapsed time (field potential duration) between a peak position of an outflow of potassium ions from the cell and a peak position of an outflow of sodium ions from the cell by comparison of the adjacent pulsation signals in the waveform of the field potential;

(iv) measuring the magnitude of fluctuations of a field potential waveform of the cardiopulsation collected from each microelectrode on which the cell is placed by comparison of adjacent pulsation signals with respect to fluctuations in time or the speed of transmission of the pulsation that transmits from the area in which the pulsation of the cell of the cellular network generates to the observation electrode;

(v) measuring a membrane potential by differentiating each field potential waveform of the cardiopulsation collected from each microelectrode on which the cell is placed;

(vi) measuring the degree of disturbance of transmission of the pulsation of an entire cell population to be compared to electrocardiogram data by overlapping field potential waveforms of the pulsating cardiomyocytes collected from each of the electrodes on which the cells are placed to generate a composite field potential waveform;

(vii) analyzing an amount of current supplied by an electric control mechanism using a feedback control mechanism to maintain a constant potential of the microelectrode on which the cell is placed; and (viii) starting measurements after at least 30 seconds from the start of the periodic forced pulsatile stimulation on the cell.

[29] The method for testing cardiotoxicity according to [27] or [28] above, comprising plotting the average value of prolongation of the FPD value of signals of the extracellular potential obtained by the apparatus according to any one of the above [1] to [14], [18] to [26] on the X-axis, and the STV value, which is the fluctuation of the FPD value, on the Y-axis, respectively, and assessing their relative positions after the addition of the agent to be evaluated in order to evaluate the cardiotoxicity.

[30] A cardiotoxicity testing apparatus, comprising:
a transparent substrate;
an area surrounded by a wall formed on the transparent substrate, wherein the area is filled with a cell culture medium;
a cell population comprising a plurality of stably pulsating cardiomyocytes which are disposed in the area filled with the cell culture medium;
a microelectrode provided in the area that is filled with the cell culture medium, wherein a cardiomyocyte of the cell population or a local portion of the cell population is placed on the microelectrode;
a reference electrode provided in the area that is filled with the cell culture medium;

a potential-measuring means for measuring the potential of the cardiomyocytes placed on the microelectrodes using lead wires which are connected to the respective microelectrodes and a lead wire which is connected to the reference electrode;

a recording means for recording data of the potential of the cardiomyocytes measured by the potential-measuring means before and after addition of an agent to be tested; and an analyzing means for calculating an elapsed time from a peak inflow of sodium ions into the cell to a peak outflow of potassium ions from the cell (extracellular potential duration) (FPD) and the magnitude of fluctuation of the FPD of the waveform of field potential (FP) based on the data of the potential acquired to assess the cardiotoxicity of the agent using the calculated FPD and STV as an index.

[31] A cardiotoxicity testing apparatus, comprising:
a transparent substrate;
an area surrounded by a wall which is formed on the surface of the transparent substrate, wherein the area is filled with a cell culture medium;
a cardiomyocyte population-holding area for holding a cell population comprising a plurality of stably pulsating cardiomyocytes in the area surrounded by the wall on the transparent substrate;
a microelectrode provided in the cardiomyocyte population-holding area on the transparent substrate for placing the cardiomyocytes thereon;
a reference electrode provided in the area to be filled with the cell culture medium on the transparent substrate;
a potential measuring means for measuring the potential of cardiomyocytes which are placed on the microelectrodes using a lead wire which is connected to the reference electrode and a lead wire which is connected to each of the microelectrodes;
a recording means for recording data of the potential of the cardiomyocytes measured by the potential measuring means before and after addition of an agent to be tested; and
an analyzing means for calculating elapsed time from the peak inflow of the sodium ion into the cells to the peak outflow of potassium ions from cells (extracellular potential duration) (FPD) and a magnitude of the fluctuation of the FPD of the waveform of field potential (FP) based on the data of the potential cells acquired to assess the cardiotoxicity of the agent using the calculated FPD and STV as an index.

[32] The cardiotoxicity testing apparatus according to [30] or [31] above, wherein the magnitude of the fluctuation of the FPD is the short-term variability (STV) of the FPD.

[33] The cardiotoxicity testing apparatus according to [30] or [31] above, further comprising a feedback potential-control mechanism to maintain a constant voltage of the microelectrode on which the cardiomyocyte is placed.

[34] The cardiotoxicity testing apparatus according to any one of [30] to [33] above, further comprising an optical system and an optical camera for measuring optically the state of the cardiomyocytes disposed on the transparent substrate, wherein image data collected by the optical camera is recorded in the recording means.

[35] The cardiotoxicity testing apparatus according to any one of [30] to [34] above, comprising a temperature control mechanism to maintain the temperature of the cardiomyocytes at an appropriate temperature.

[36] The cardiotoxicity testing apparatus according to any one of [30] to [33] above, which is configured to measure the magnitude of the fluctuation of the FPD by comparing adjacent waveforms of the field potential (FP) signals.

[37] The cardiotoxicity testing apparatus according to any one of [30] to [33] above, wherein the apparatus is configured to measure the magnitude of the fluctuation of the elapsed time (field potential duration) between the peak position of the outflow of sodium ions and the peak position of the outflow of potassium ions from the cells by comparison of the adjacent pulsation signals in the waveform of the field potential.

[38] The cardiotoxicity testing apparatus according to any one of [30] to [33] above, wherein the apparatus is configured to measure the membrane potential by differentiating each field potential waveform of the cardiopulsation collected from each microelectrode on which the cells is placed.

[39] The cardiotoxicity testing apparatus according to any one of [30] to [33] above, wherein the apparatus is configured to measure the degree of the disturbance of the transmission of the pulsation of the entire cell population for comparison with the electrocardiogram data by overlapping the field potential waveforms of the pulsating myocardial cells collected from each electrode on which the cell is placed to generate a composite field potential waveform.

[40] The cardiotoxicity testing apparatus according to any one of [30] to [34] above, wherein the microelectrodes are composed of a multi-electrode array consisting of a plurality of microelectrodes.

[41] The cardiotoxicity testing apparatus according to any one of [30] to [35] above, wherein the apparatus is configured to start measurements after at least 30 seconds from the start of the periodic forced pulsatile stimulation on the cell.

[42] The cardiotoxicity apparatus according to any one of [30] to [37] above, further comprising a reference electrode for noise cancellation, wherein the reference electrode is placed near the microelectrode.

[43] The cardiotoxicity testing apparatus of [42] above, wherein the microelectrode comprises a stimulation electrode and a measurement electrode.

[44] The cardiotoxicity testing apparatus according any one of [30] to [39] above, comprising a culture-medium supply/drain channel for supplying and/or draining the cell culture medium to and/or from the area surrounded by the wall.

[45] The cardiotoxicity testing apparatus according to any one of [30] to [39] above, comprising an agent supply/drain channel for continuously introducing a test agent solution from the bottom of the cardiomyocyte culturing area thereto, and draining from the upper surface of the solution, and a mechanism for monitoring and maintaining the temperature of the agent solution at an appropriate temperature, wherein a part of the channel is optically transparent for being capable of measuring the concentration of the agent solution that is introduced, and the apparatus allows quantitative spectrophotometric measuring of the absorption in the wavelength range of 280 nanometers to 800 nanometers.

[46] The cardiotoxicity testing apparatus according to any one of [30] to [31] above, wherein the microelectrode is transparent.

[47] The cardiotoxicity testing apparatus according to [43] above, further comprising a metal layer provided on the wiring of the transparent electrode that is disposed in an area other than the area for observation by an optical system to reduce the resistance of microelectrodes.

[48] The cardiotoxicity testing apparatus according to any one of [30] to [44] above, wherein a plurality of the cultured cardiomyocytes are arranged linearly on the substrate to form a cardiomyocyte network, and an electrode is arranged to stimulate locally at an endpoint of the linear cardiomyocyte network.

[49] The cardiotoxicity testing apparatus according to [45] above, further comprising a linear measurement electrode on which a majority of the cardiomyocytes in the linear cardiomyocyte network can be disposed.

[50] The cardiotoxicity apparatus according to any one of [30] to [44] above, wherein a plurality of the cultured cardiomyocytes are arranged in an annular fashion on the substrate to form an annular network, and a portion of the annular cardiomyocyte network is cut-out and an electrode is arranged at the cut-out point for local stimulation.

[51] The cardiotoxicity testing apparatus according to [47] above, further comprising a single ring-shaped measurement electrode on which a majority of the cardiomyocytes in the ring-like cardiomyocyte network can be disposed.

[52] A method for testing cardiotoxicity of an agent that acts on the cardiomyocytes using the cardiotoxicity testing apparatus according to any one of [30] to [48] above, comprising:

adding a test agent to a cardiomyocyte population including a plurality of stably pulsating cardiomyocytes which are cultured in the cell culture medium, and evaluating changes in the pulsation produced by the population before and after the addition of the agent to the cell culture medium, wherein an prolongation of the FPD waveform and the increase in the magnitude of the fluctuation of the FPD are used as an index when evaluating the change in the pulsation.

[53] A cardiotoxicity testing method, comprising steps of:

preparing a cell population containing a plurality of stably pulsating cardiomyocytes;

culturing the cell population in the culture vessel, wherein a multi-electrode array is disposed on the bottom surface of the culture vessel;

adding a subject agent to the cell population being cultured to measure the membrane potential of the culture cell population using the multi-electrode array, wherein the membrane potential of the culture cell population is measured and the data of the membrane potential is acquired before and after the addition of the agent; and calculating an elapsed time from a peak inflow of sodium ions into the cells to a peak outflow of potassium ions from the cells (extracellular potential duration) (FPD) and the magnitude of fluctuation of the FPD of a waveform of the field potential (FP) based on data of the potential acquired to assess the cardiotoxicity of the agent using as an index a combination of the calculated FPD and the magnitude of the fluctuation of the FPD.

[54] The method according to [19] and [53] above, wherein the magnitude of the fluctuation of the FPD is the short-term variability (STV) of the FPD.

[55] The method according to [53] above, comprising evaluating the cardiotoxicity of the agent using an prolongation of the FPD waveform and an increase in the STV after addition of the agent as an indicator in assessing the cardiotoxicity of the agent.

[56] The method according to [55] above, comprising creating a two-dimensional plot with the FPD frequency in which an prolongation of the FPD waveform is greater than a predetermined threshold and the STV frequency in which an increase in STV is greater than a predetermined threshold, and assessing the cardiotoxicity of the agent on the basis of the two-dimensional plot.

[57] The method according to [56] above, comprising assessing the cardiotoxicity of the agent from the relative position of the plot of multiple agents in the two-dimensional plot.

More specifically, the present invention provides the following apparatus and method.

(1) A quality evaluation apparatus for cells, comprising:
a substrate;
a plurality of stably pulsating subject cardiomyocytes or a cell population comprising the subject cells placed on the substrate;
a wall formed on the substrate and surrounding the periphery of the cell population to hold a cell culture medium;
a culture-medium supply/drain channel for supplying and/or draining the cell culture medium to and/or from the area surrounded by the wall;
a microelectrode on which a single cell or a local portion of the cell population is placed;
a reference electrode provided in the area which is to be filled with the cell culture and surrounded by the wall;
a potential-measuring means for measuring a membrane potential of the cell that is placed on the microelectrode using lead wires which are connected respectively to each of the microelectrodes and a lead wire which is connected to the reference electrode; and
a control/recording means for controlling an electrical stimulation delivered to the microelectrode and recording data of the potential measured by the potential measuring means,
wherein the quality evaluation apparatus is capable of varying the electrical stimulation to be sent to the microelectrode at an interval in a stepwise fashion, and of
(i) determining whether the cardiomyocytes or the cell population respond to forced pulsatile stimulation by the electrical stimulation at the same interval as the forced pulsatile stimulation; measuring the response in terms of the range of frequency of the forced pulsatile stimulation; and judging that one of the sufficient conditions for a healthy cardiomyocyte is met when it is observed that the pulsation of the cells can follow the forced pulsatile stimulation, and
(ii) judging that one of the sufficient conditions for a healthy cardiomyocyte is met when it is observed that the variation of FPD in response to the forced pulsatile stimulation is between the $FPD/(RR)^{1/3}$ and $FPD/(RR)^{1/2}$, within the frequency range in which the pulsation of the cell can follow the forced pulsatile stimulation intervals (RR) by the electrical stimulation.

(2) A quality evaluation method for cells comprising using a cell quality evaluation apparatus, wherein the apparatus comprising:
a substrate;
a plurality of stably pulsating subject cardiomyocytes or a cell population comprising the subject cells placed on the substrate;
a wall formed on the substrate and surrounding the periphery of the cell population to hold a cell culture medium;
a culture-medium supply/drain channel for supplying and/or draining the cell culture medium to and/or from the area surrounded by the wall;
a microelectrode on which a single cell of the cell population or a local portion of the cell population is placed;
a reference electrode provided in the area which is to be filled with the cell culture and is surrounded by the wall;
a potential-measuring means for measuring membrane potential of the cell that is placed on the microelectrode using lead wires which are connected respectively to each of the microelectrodes and a lead wire which is connected to the reference electrode; and
a control/recording means for controlling an electrical stimulation delivered to the microelectrode and recording data of the potential measured by the potential measuring means; and
the method further comprising:
varying the electrical stimulation to be sent to the microelectrode at an interval in a stepwise fashion, and
(i) determining whether the cardiomyocytes or the cell population respond to forced pulsatile stimulation by the electrical stimulation at the same interval as the forced pulsatile stimulation; measuring the response in terms of the range of frequency of the forced pulsatile stimulation; and judging that one of the sufficient conditions for a healthy cardiomyocyte is met when it is observed that the pulsation of the cells can follow the forced pulsatile stimulation, and
(ii) judging that one of the sufficient conditions for a healthy cardiomyocyte is met when it is observed that the variation of FPD in response to the forced pulsatile stimulation is between the $FPD/(RR)^{1/3}$ and $FPD/(RR)^{1/2}$ within the frequency range in which the pulsation of the cell can follow the forced pulsatile stimulation intervals (RR) by the electrical stimulation.

(3) A cardiotoxicity testing apparatus configured to measure the magnitude of the fluctuation of the field potential waveform of the pulsation of cardiomyocytes by comparison of adjacent pulsation signals.

(4) The cardiotoxicity testing apparatus according to (3) above, wherein the apparatus is configured to measure the magnitude of fluctuation of field potential duration (FPD), i.e., an elapsed time from a peak position of sodium-ion outflow from the cell to a peak position of potassium-ion outflow from the cell on the field potential waveform by comparison of adjacent pulsation signals (5) The cardiotoxicity testing apparatus according to (3) or (4) above, wherein the apparatus is configured to calculate the magnitude of the FPD and the fluctuation of the FPD, and to use an index configured from a combination of the calculated magnitude of the FPD and fluctuation of the FPD.

(6) The cardiotoxicity testing apparatus according to any one of (3)-(5) above, wherein the magnitude of the fluctuation of the FPD is the short-term variability (STV) of the FPD.

(7) The cardiotoxicity testing apparatus according to any one of (3)-(6) above, comprising:
a transparent substrate;
an area surrounded by a wall formed on the transparent substrate, wherein the area is filled with a liquid cell culture medium;
a cell population comprising a plurality of stably pulsating cardiomyocytes which are disposed in the area that is filled with the cell culture medium;
a microelectrode provided in the area that is filled with the cell culture medium, wherein a cardiomyocyte of the cell population or a local portion of the cell population is placed on the microelectrode;
a reference electrode provided in the area that is filled with the cell culture medium;
an electrical potential measuring means for measuring the electrical potential of the cardiomyocyte placed on the microelectrode, comprising lead wires which are connected respectively to each of the microelectrodes and a lead wire which is connected to the reference electrode; and
a recording means for recording data of the electrical potential of the cardiomyocytes before and after addition of a test agent measured by the electrical potential measuring means.

(8) The cardiotoxicity testing apparatus according to any one of (3)-(7) above, wherein the cell population comprising the stably pulsating cardiomyocytes comprises a cellular network comprising a plurality of cardiomyocytes and fibroblasts that are capable of transmitting the pulsation.

(9) The cardiotoxicity testing apparatus according to any one of (3)-(8) above, comprising:

a transparent substrate;

a pacemaker area comprising a cell population including a plurality of stably pulsating cardiomyocytes placed on the transparent substrate;

a cellular network comprising a plurality of cardiomyocytes and fibroblasts that are arranged in series, disposed on the transparent substrate and transmit the pulsation in conjunction with the cell population;

a wall formed on the transparent substrate to surround the periphery of the cell population and the cellular network and to fill a cell culture medium;

a culture-medium supply/drain channel for supplying and/or draining the cell culture medium to and/or from the area surrounded by the wall;

an agent delivery channel for introducing an agent acting on the cells to the cell culture medium;

a microelectrode on which a single cell of the cell population or a local portion of the cell population is placed;

microelectrodes on which each individual cell of the cellular network is respectively placed;

a reference electrode provided in the area which is filled with the cell culture medium and is surrounded by the wall;

a potential-measuring means for measuring a cell potential of the cell that is placed on the microelectrode using lead wires which are connected respectively to each of the microelectrodes and a lead wire which is connected to the reference electrode; and a control/recording means for controlling an electrical stimulation delivered to the microelectrode and recording data of the potential measured by the potential measuring means.

(10) The cardiotoxicity testing apparatus according to any one of (3)-(9) above, which is configured to enable provision of at least one microelectrode on which the cell is placed with a stimulus for forced pulsation at regular intervals, wherein the microelectrode is for placing a cell containing a stably pulsating cardiomyocyte.

(11) The cardiotoxicity testing apparatus according to any one of (8)-(10) above, comprising an electrode for providing a stimulus locally at an end point of the cellular network in which cells are arranged in series.

(12) The cardiotoxicity testing apparatus according to any one of (8)-(11) above, wherein the cellular network is arranged in a ring shaped, and wherein a portion of the ring is cutout and an electrode for locally providing a stimulus is located at the cutout point.

(13) The cardiotoxicity testing apparatus according to any one of (8)-(11) above, wherein the apparatus is configured to measure the magnitude of the fluctuation of the waveform of the field potential of the cardiopulsation collected from each of the microelectrodes on which each of the cells is placed by comparing between the adjacent pulsations, which measures the fluctuations of transmission time or transmission speed of the pulsation of the cells of the cellular network from the area where the pulsation of the cell is generated to the observation electrode.

(14) The cardiotoxicity testing apparatus according to any one of (1)-(13) above, comprising a temperature control module to maintain the cardiomyocytes at an appropriate temperature.

(15) The cardiomyocyte testing apparatus according to any one of (1)-(14) above, wherein the microelectrodes constitute a multi-electrode array consisting of a plurality of microelectrodes.

(16) A cardiotoxicity testing method, comprising:

measuring the magnitude of fluctuation of a waveform of the field potential of pulsating cardiomyocytes by comparison of adjacent pulsation signals.

(17) The cardiotoxicity testing method according to (16) above, comprising steps of:

preparing a cell population containing a plurality of stably pulsating cardiomyocytes;

culturing the cell population in a culture vessel, wherein a multi-electrode array is disposed on the bottom surface of the culture vessel;

adding a subject agent to the cell population being cultured to measure a membrane potential of the culture cell population using a multi-electrode array, wherein the membrane potential of the culture cell population is measured and data of the membrane potential is acquired before and after the addition of the agent; and calculating an elapsed time from a peak inflow of sodium ions into the cell to a peak outflow of potassium ions from the cell (extracellular potential duration) (FPD) and the magnitude of the fluctuation of the FPD of the waveform of the field potential (FP) based on the data of the membrane potential acquired to assess the cardiotoxicity of the agent using as an index a combination of the calculated FPD and the magnitude of the fluctuation of the FPD.

(18) The cardiotoxicity testing method according to (16) or (17) above, comprising:

examining the toxicity of an agent that acts on cardiomyocytes by assessing whether or not the rate at which the pulsation produced by the population of the cardiomyocytes propagates in the cellular network area is delayed when the agent acting on the cells is added to the culture medium using the cardiotoxicity testing apparatus according to any one of (8)-(15) above.

(19) The cardiotoxicity testing method according to any one of (16) to (18) above comprising:

examining the toxicity of an agent that acts on cardiomyocytes by assessing whether or not the rate at which the pulsation produced by the population of the cardiomyocytes propagates in the cellular network area is delayed when the agent acting on the cells is added to the culture medium using the cardiotoxicity testing apparatus according to any one of (8)-(15) above, the method further comprising at least one of the following steps:

(i) providing a forced pulsatile stimulation at regular intervals to a cell, wherein the cell is placed on at least one of the microelectrodes for placing the cells of the cellular network;

(ii) measuring the magnitude of the fluctuations of the field potential waveform of cardiopulsation collected from each microelectrode on which the cell is placed by comparison of the adjacent pulsation signals;

(iii) measuring the magnitude of the fluctuation of the elapsed time (field potential duration) between the peak position of the outflow of potassium ions from the cell and the peak position of the outflow of sodium ions from the cell by comparison of the adjacent pulsation signals in the waveform of the field potential;

(iv) measuring the magnitude of the fluctuations of the field potential waveform of cardiopulsation collected from each microelectrode on which the cell is placed by comparing the adjacent pulsation signals the fluctuation of time or the speed of transmission of the pulsation from the area in which the pulsation of the cell of the cellular network generates to the observation electrode;

(v) measuring the membrane potential by differentiating each field potential waveform of cardiopulsation collected from each microelectrode on which the cells is placed;

(vi) measuring the degree of disturbance of the transmission of the pulsation of the entire cell population to be compared to the electrocardiogram data by overlapping the field potential waveforms of the pulsating cardiomyocytes collected from each electrode on which the cell is placed to generate a composite field potential waveform;

(vii) analyzing the amount of current supplied by an electric control mechanism using a feedback control mechanism to maintain a constant potential of the microelectrode on which the cell is placed; and (viii) starting measurements after at least 30 seconds from the start of the periodic forced pulsatile stimulation on the cell.

(20) The method according to any one of (16)-(19) above, wherein the magnitude of the fluctuation of the FPD is the short-term variability (STV) in FPD.

According to the present invention, changes in the response of cardiomyocytes and fibroblasts to an agent can be accurately evaluated by measuring fluctuations of cells.

Conventionally, proposals have been made to test cardiotoxicity independently using field potential duration (FPD) (see description below) and the magnitude of the fluctuation of adjacent pulsations of adjacent cardiomyocytes (for example, short-term variability: STV). However, no proposals have been made in relation to testing of cardiotoxicity using a combination of both those features. The method for testing cardiotoxicity of the present invention enhances the accurate evaluation of cardiotoxicity by using not only the prolongation of the FPD waveform, but also an increase in the magnitude of the fluctuation of the adjacent pulsations of the cardiomyocytes (STV).

BRIEF DESCRIPTION OF THE DRAWINGS

FIG. 35 is a table summarizing the results shown in FIG. 33 and FIG. 34 regarding an example of the response of the cell population when forced pulsation is given to a partial area of the cardiomyocyte population during the cardiomyocyte-network measurements which are measurable by the measurement system of the present invention.

MODE FOR CARRYING OUT THE INVENTION

Figure 1:
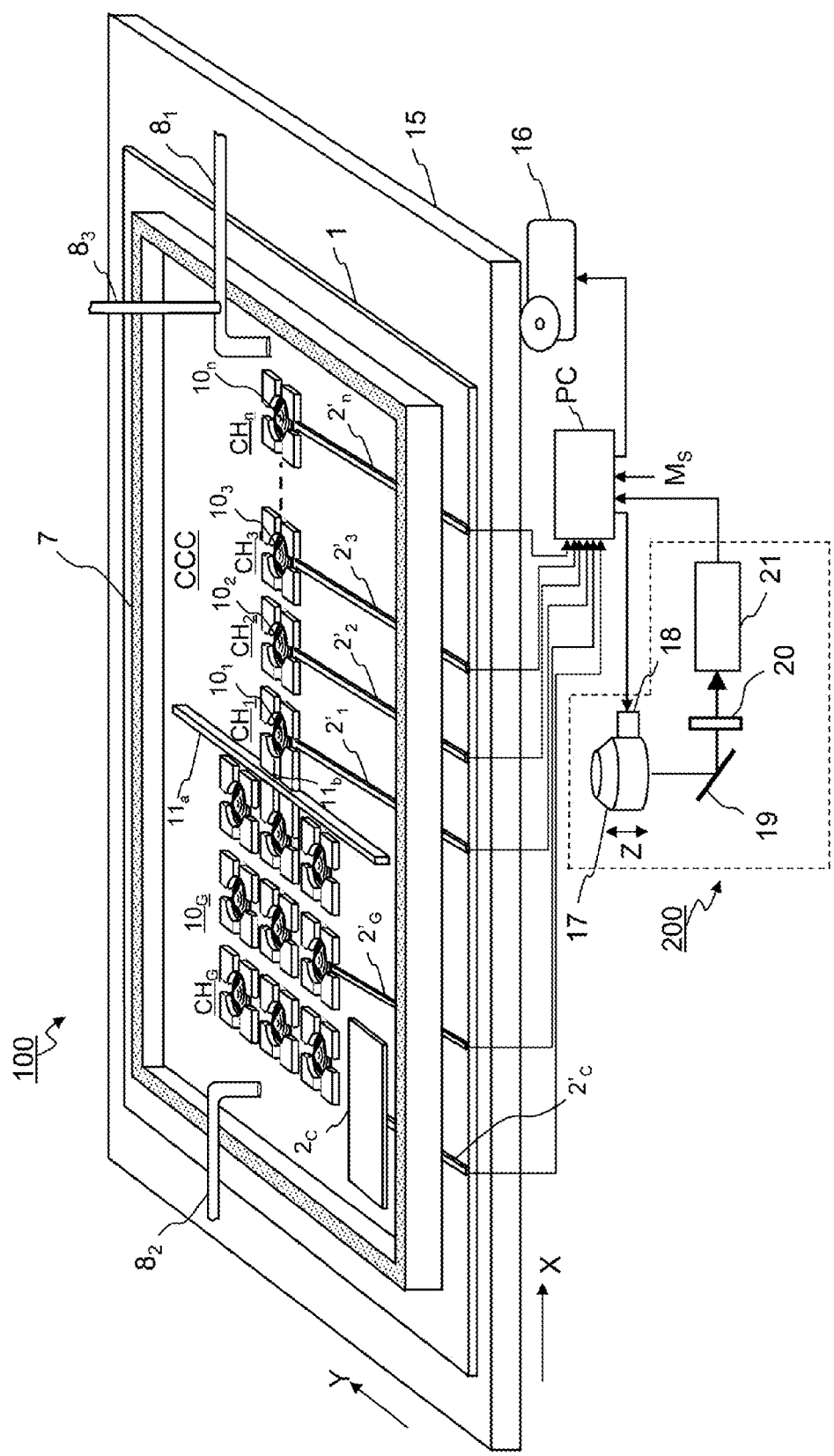
FIG. 1 is a perspective view schematically showing an exemplary structure of a cardiotoxicity testing apparatus according to an example of the present invention.
Figure 2:
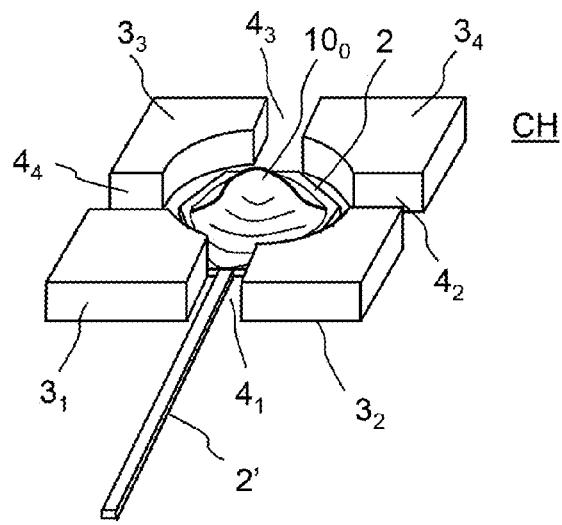
FIG. 2 is a perspective view schematically showing an exemplary structure of a cell holding unit CH of the cardiotoxicity testing apparatus shown in FIG. 1.
Figure 3:
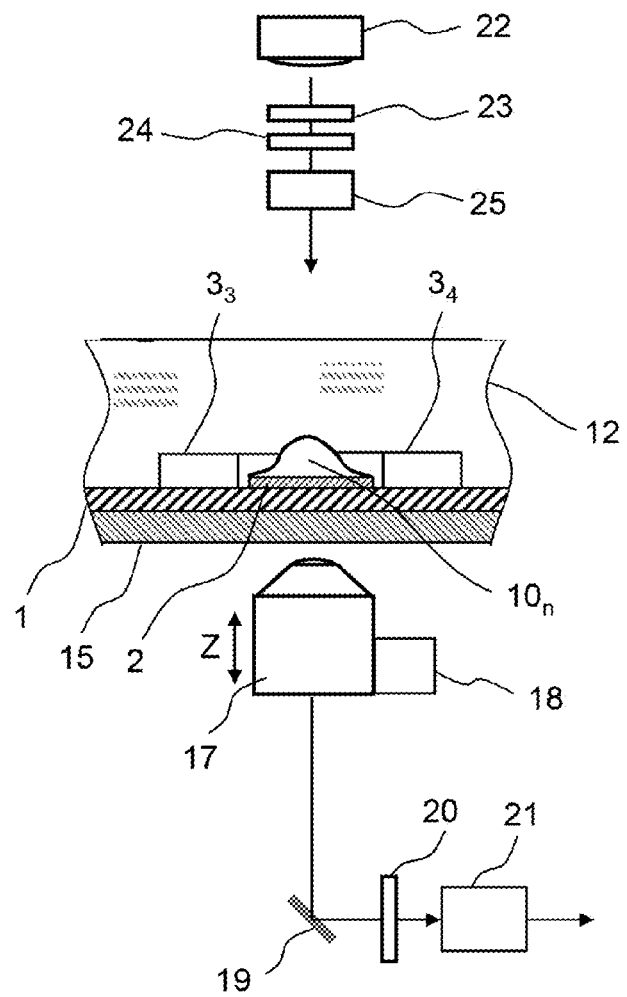
FIG. 3 is a diagram for illustrating an optical system for optically detecting a cell on the cell holding unit CH of the cardiotoxicity testing apparatus shown in FIG. 1.

FIG. 1 is a perspective view schematically showing an exemplary structure of an apparatus for testing cardiotoxicity according to an example of the present invention. FIG. 2 is a perspective view schematically showing an exemplary structure of a cell holding unit CH of the cardiotoxicity testing apparatus shown in FIG. 1. FIG. 3 is a view for illustrating an optical system for optically detecting the cell retained in the cell holding unit CH of the cardiotoxicity testing apparatus shown in FIG. 1.

Referring to FIG. 1 and FIG. 2, the cardiotoxicity testing apparatus 100 mainly consists of parts built on a transparent substrate 1. The transparent substrate 1 is an optically transparent material, for example, a glass substrate or a silicon substrate. The microelectrodes 2 are transparent ITO electrodes, for example, arranged on the transparent substrate 1. Reference numeral 2' denotes readout lines from the microelectrodes 2. Reference numerals $3_1$, $3_2$, $3_3$ and $3_4$ denote agarose gel walls, which are arranged around each of the microelectrode 2 with gaps $4_1$, $4_2$, $4_3$ and $4_4$. The agarose gel walls $3_1$, $3_2$, $3_3$ and $3_4$ are cutout in the middle to form a space as cell housing. The microelectrode 2 is placed on the transparent substrate 1, as necessary, within the space as the cell housing formed with the agarose gel walls $3_1$, $3_2$, $3_3$ and $3_4$. Regardless of the presence of the microelectrode 2, a single cell 10 can be retained in the cell housing. In FIG. 2, the microelectrode 2 is arranged on the transparent substrate 1 within the space as the cell housing formed with the agarose gel walls $3_1$, $3_2$, $3_3$ and $3_4$, where a cardiomyocyte 10 is additionally retained on the microelectrode 2. The microelectrode 2 is shown to be connected to the readout line 2'. A material, e.g., collagen, which enhances cellular adherence to the electrode surface or the transparent substrate, is preferably applied onto the cell-bearing surface of the microelectrode 2 or, directly onto the transparent substrate 1 when the cell is disposed in the absence of the microelectrode 2. Since the cell within the cell housing formed with the agarose gel walls $3_1$, $3_2$, $3_3$ and $3_4$ is non-adherent to the agarose gel, the cell 10 will not transfer beyond the walls even if its height is equivalent to the heights of these walls $3_1$, $3_2$, $3_3$ and $3_4$. Furthermore, since the gaps $4_1$, $4_2$, $4_3$ and $4_4$ surrounding the cell housing formed by cutting out in the middle of the agarose gel walls $3_1$, $3_2$, $3_3$ and $3_4$ are smaller than the size of the cell, the cell 10 will not move across these gaps $4_1$, $4_2$, $4_3$ and $4_4$.

With reference to FIG. 1, the cell holding units $CH_1$, $CH_2$, $CH_3$ and $CH_n$ each retains a cardiomyocyte or a fibroblast $10_1$, $10_2$, $10_3$ or $10_n$ in the cell housing. Each holding unit is provided, although not evident from the figure, with the microelectrode 2 from which extends the readout line $2'_1$, $2'_2$, $2'_3$ or $2'_n$. These cardiomyocytes or fibroblasts form a tandemly arranged cell communication channel CCC. Here, "n" is, for example, 20. Although these twenty tandemly-arranged cardiomyocytes and fibroblasts may be allocated randomly, the cells in the cell holding units $CH_1$ and $CH_{20}$ are preferably cardiomyocytes. On the left side of this cell communication channel CCC are provided 3×3 cell holding units $CH_G$ to form a region that retains a cardiomyocyte population $10_G$ where each cell holding unit CH retains a cardiomyocyte 10. This cell population $10_G$ serves as a stably-pulsating pacemaker. Among the cell population $10_G$, only one of the cell holding units CH is provided with the microelectrode 2 from which extends the readout line $2'_G$. In addition, the right middle cell holding unit CH of the cell population $10_G$ is arranged to face the cell holding unit $CH_1$ of the cell communication channel CCC. A barrier $11_a$ is provided on the right of the cell population $10_G$ and the left of the cell communication channel CCC. A small opening $11_b$ is formed in the lower middle part of this barrier $11_a$. On both sides of this opening $11_b$, the right middle cell holding unit CH of the cell population $10_G$ is facing the cell holding unit $CH_1$ of the cell communication channel CCC to allow physical contact/intercellular interaction between the cells retained in the cell housings via the gaps 4 at the periphery of the housings. A comparison electrode $2_C$ is provided below the cell population $10_G$, from which the readout line $2'_C$ extends.

Reference numeral 7 denotes a surrounding wall that surrounds the cell population $10_G$, the cell communication channel CCC and the comparison electrode $2_C$. Reference numerals $8_1$ and $8_2$ denote pipes for supplying a cell culture solution into the region surrounded by the wall 7 and for draining the cell culture solution from the region surrounded by the wall 7. In the case of this figure, a culture solution is supplied from the pipe $8_1$ extending toward the bottom surface of the substrate 1 and drained from the pipe $8_2$ extending from the bottom surface of the substrate 1. A pipe $8_3$ is connected to the culture solution-supplying pipe $8_1$ near the culture solution outlet so that an agent that acts on the cells is supplied via this pipe $8_3$. Accordingly, the cells 10 are exposed to the cell culture solution supplied from the pipe $8_1$ into the region surrounded by the wall 7, while being stably retained on the microelectrodes 2. Once the cells no longer need to be exposed to the culture solution, the culture solution can be drained from the region surrounded by the wall 7 with the pipe $8_2$. Moreover, when the culture solution needs to be exchanged with a fresh culture solution, the culture solution may be supplied after or while draining the cell culture solution. On the other hand, if one wants to affect the cells with an agent, the agent for affecting the cells may be added to the culture solution via the pipe $8_3$ for supply together with the culture solution via the pipe $8_1$ while draining the cell culture solution from the pipe $8_2$. In this case, due to the barrier $11_a$ provided between the cell population $10_G$ and the cell communication channel CCC, when the culture solution containing the agent is supplied into the region surrounded by the wall 7 from the pipe $8_1$, the cells of the cell population $10_G$ are less influenced by the agent than the cells of the cell communication channel CCC. Specifically, when an agent-containing culture solution is supplied via the pipe $8_1$, this culture solution flows through the spacing between the wall 7 and the both edges of the barrier $11_a$ as well as over the top of the barrier $11_a$ toward the cell population $10_G$. Thus, the cells of the cell population $10_G$ are also affected by the agent. This influence, however, is indirect compared to the influence on the cells of the cell communication channel CCC, and thus it does not affect the function as a pacemaker. The structures and arrangements of the pipes $8_1$, $8_2$ and $8_3$ may arbitrarily be changed depending on the measurement configuration. For example, the pipes $8_1$ and $8_3$ may be separated, or the pipe $8_2$ may be omitted while using the pipe $8_1$ for both supply and drainage.

PC refers to a personal computer (potential measurement means, control/recording means), which measures and records the membrane potentials between the readout lines 2' from the microelectrodes 2 of the cell holding units CH and the readout line 2' from the comparison electrode $2_C$. Furthermore, operation signals Ms from an operator are input into the personal computer 9.

The cardiotoxicity testing apparatus 100 may be mounted on an XY stage 15 of the optical observation device 200 where the pulsation of a certain cell 10 of the cell communication channel CCC can be observed with an optical system. The XY stage 15 is optically transparent and may be moved to a given position with an X-Y drive unit 16 according to the signal given by the personal computer PC reflecting the operation signal Ms from the operator. FIG. 3 shows an exemplary configuration for observing the pulsating state of a cell $10_n$ of the cell communication channel CCC. Reference numeral 12 denotes a culture solution.

Reference numeral 22 denotes a light source of a phase-contrast microscope or a differential interference microscope. Generally, a halogen lamp is used. Reference numeral 23 denotes a bandpass filter that only allows transmission of light with a specific wavelength from the light source for observation with a stereoscopic microscope such as a phase-contrast microscope. For example, in the case of observing the cell $10_n$, narrow-band light having a wavelength in the vicinity of 700 nm is used to prevent damage to the cell $10_n$. Reference numeral 24 denotes a shutter that has a function of blocking irradiation light when image measurement is not executed, for example, while moving the XY stage 15. Reference numeral 25 denotes a condenser lens, where a phase ring is installed for phase-contrast observation or a polarizer for differential interference observation. The cardiotoxicity testing apparatus 100 formed on the substrate 1 is mounted on the XY stage 15 which can be moved with the X-Y drive unit 16 to observe and measure a certain location of the cardiotoxicity testing apparatus 100. The pulsating state of the cell $10_n$ in the cardiotoxicity testing apparatus 100 is observed with an objective lens 17. The focal position of the objective lens 17 can be transferred in the Z-axis direction with a drive unit 18 according to the signal from the PC. The magnification of the objective lens 17 may be 40 or higher. The objective lens 17 allows observation of a phase-contrast image or a differential interference image of the cell $10_n$ obtained with light transmitted from the light source 22. A diachronic mirror 19 and a bandpass filter 20 that reflect light having the same wavelength as the light that passes through the bandpass filter 23 allow observation of only a phase-contrast microscope image or a differential interference microscope image with a camera 21. The image signal observed with the camera 21 is input into the personal computer PC. In addition, although it is not illustrated in a diagram, images are displayed on a monitor or a display connected to the PC.

Exemplary dimensions of the structures of the cardiotoxicity testing apparatus 100 shown in FIG. 1 are as follows. In this example, the size of a cell is 10 μmφ. The transparent substrate 1 has dimensions of 100 mm×150 mm, the microelectrode 2 has dimensions of 8 μm×8 μm and each of the agarose gel walls $3_1$, $3_2$, $3_3$ and $3_4$ has dimensions of 20 μm×20 μm×10 μm (height). Each of the gaps $4_1$, $4_2$, $4_3$ and $4_4$ has a width of 2 μm, the cell housing formed with the agarose gel walls $3_1$, $3_2$, $3_3$ and $3_4$ has a 12 μmφ cylindrical space, and the wall 7 has external dimensions of 5 mm×5 mm with a height of 5 mm. The height of the barrier $11_a$ is 1 mm. Although the microelectrode 2 has a square shape of 8 μm×8 μm in this example, it may be an annular electrode of 10 μmφ that corresponds to the shape of the cell housing made with the agarose gel walls $3_1$, $3_2$, $3_3$ and $3_4$ and the widths of the gaps $4_1$, $4_2$, $4_3$ and $4_4$.

Hereinafter, an exemplary structure of the cell response measurement apparatus 100 of the present invention and a specific example of measurement using the same will be described.

Figure 4:
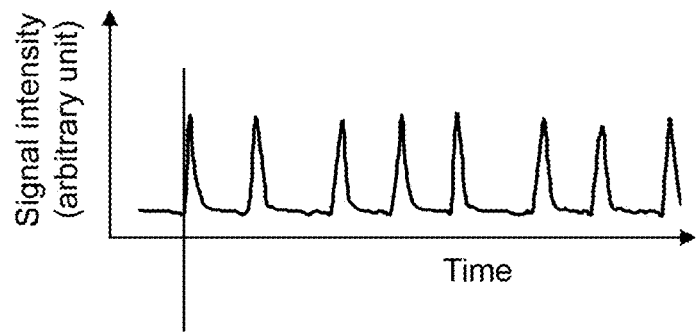
FIGS. 4(a), 4(b) and 4(c) are diagrams showing signals associated with measurement of membrane potentials. Each diagram shows time along the horizontal axis and the membrane potential between the microelectrode 2 and the comparison electrode $2_C$ along the vertical axis.
Figure 4:
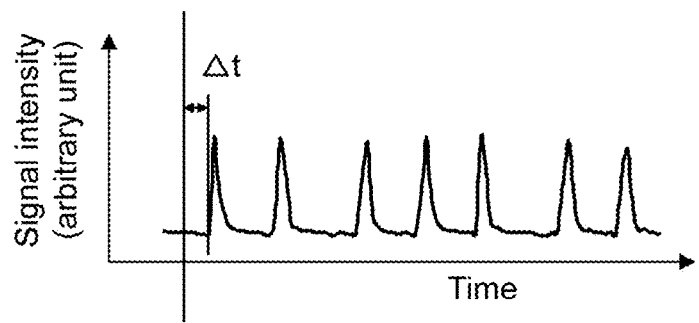
Figure 4:
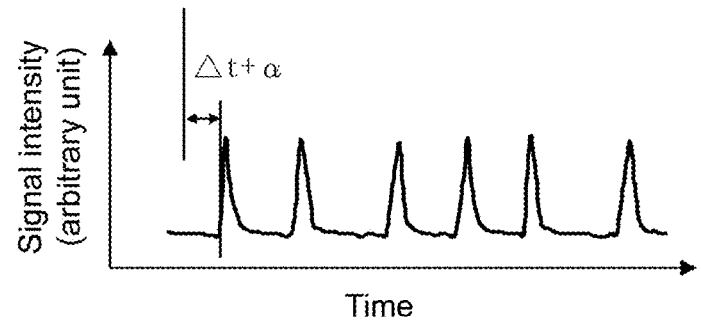

FIGS. 4(a), 4(b) and 4(c) are diagrams showing signals associated with measurement of membrane potentials. Each diagram shows time along the horizontal axis and the membrane potential between the microelectrode 2 and the comparison electrode $2_C$ along the vertical axis. FIG. 4(a) shows membrane potentials resulting from the pulses of the cell population $10_G$. Here, a potential refers to an electric difference between the readout line $2'_G$ extending from one of the cell population $10_G$ and the readout line $2'_C$ extending from the comparison electrode $2_C$ shown in FIG. 1. The diagram shows stable pulses indicating that the cells are capable of serving as a pacemaker. FIG. 4(b) shows membrane potentials resulting from the pulses of a target cell in a normal state where the culture solution does not contain an agent. Here, a cell targeted for measurement is the cell $10_n$ of the cell communication channel CCC, where the potential between the readout line $2'_n$ extending from the cell $10_n$ and the readout line $2'_C$ extending from the comparison electrode $2_C$ are measured. As can be appreciated from comparison with the waveform of FIG. 4(a), the time required for conducting the pulse of the cell 10 of the cell communication channel CCC is delayed by Δt. Meanwhile, FIG. 4(c) shows membrane potentials resulting from the pulse of the target cell in a state where the culture solution contains an agent. Again, the cell targeted for measurement is the cell $10_n$ of the cell communication channel CCC for the sake of facilitating comparison with FIG. 4(b). As can be appreciated from comparison with the waveforms of FIGS. 4(a) and 4(b), the time required for conducting pulse of the cell 10 of the cell communication channel CCC is found to be delayed not just by Δt but by Δt+α. This means that the level of the Na-ion inhibition due to the agent acting on the cell of the cell communication channel CCC appears as the increase in the delayed time, i.e., +α. Specifically, toxicity of an agent on a cardiomyocyte can be assessed as sodium-ion inhibition. It should be noted that microelectrodes that are used for observation may be referred to as observation electrodes herein.

Figure 5:
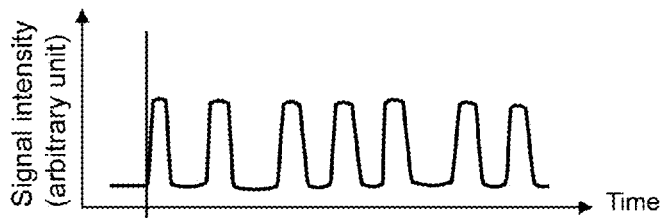
FIGS. 5(a), 5(b) and 5(c) are diagrams showing signals associated with the changes in the volume due to cell pulsation, which is measured with the optical system.
Figure 5:
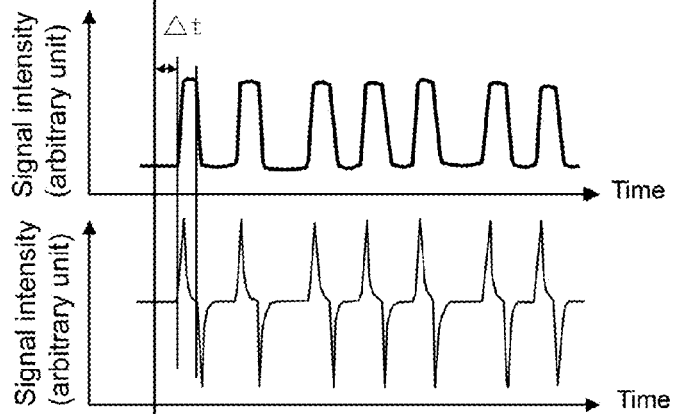
Figure 5:
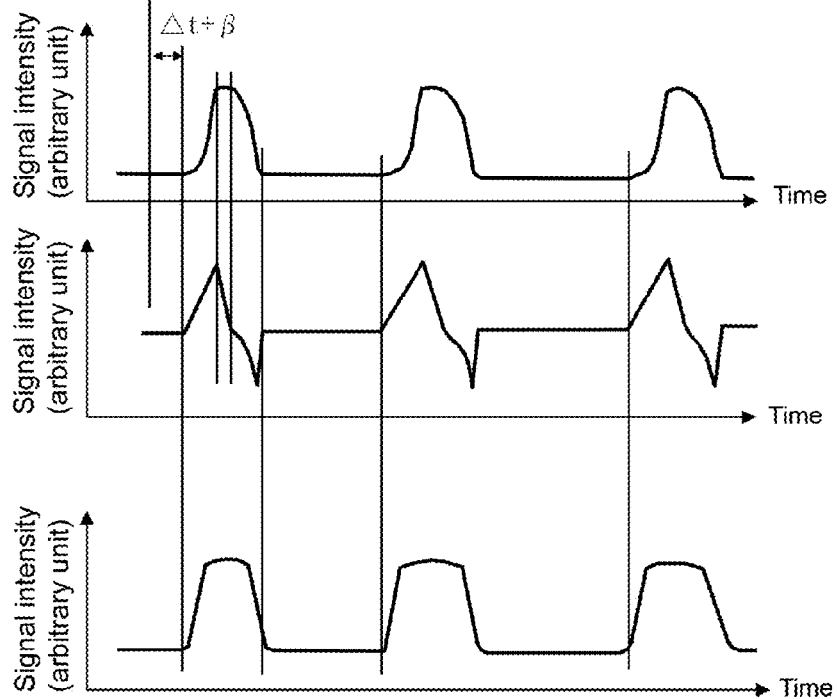

FIGS. 5(a), 5(b) and 5(c) are diagrams showing signals associated with the changes in the volume due to pulse of cells, which is measured with the optical system. FIG. 5(a) shows the change in the volume associated with pulse of a cell of cell population $10_G$, where the pulse of one of the cells of the cell population $10_G$ is optically detected with the configuration shown in FIG. 3. The contraction and dilatation associated with the pulsation of the cell can be observed as pulse-shaped changes. The cycle of this waveform is the same as the cycle of the changes in the membrane potential associated with the pulsation shown in FIG. 4(a). FIG. 5(b) shows, in the upper diagram, the change in the volume associated with the pulsation of the target cell under the normal state where the culture solution is free of the agent, and shows, in the lower diagram, a waveform of the same in time-differential values for evaluation as electric signals. Again, the cell targeted for measurement is the cell $10_n$ of the cell communication channel CCC, where the pulse of the cell $10_n$ is optically detected with the configuration shown in FIG. 3. As can be appreciated from comparison with the waveform shown in FIG. 5(a), the time required for conducting pulse of the cell 10 of the cell communication channel CCC is delayed by $\Delta t$. Meanwhile, FIG. 5(c) shows diagrams for evaluating changes in the volume associated with the pulsation of the target cell under the state where the culture solution contains an agent. In FIG. 5(c), the time axes are extended when compared to those in FIGS. 5(a) and 5(b). The upper diagram represents a waveform corresponding to the waveform of the upper diagram of FIG. 5(b), where the time required for conducting pulse of the cell 10 of the cell communication channel CCC is further delayed by $\beta$ in addition to $\Delta t$ as can be appreciated by comparison with the waveform shown in FIG. 5(a). The influence on the change in the volume associated with the pulsation of the target cell is more prominent in a smaller inclination of the change in the volume rather than the increase in the delay. This is apparent from comparison with the change in the volume with an agent-free culture solution shown as a reference waveform in the lower diagram in FIG. 5(c). The middle diagram of FIG. 5(c) shows the waveform of the upper diagram processed as time-differential values for evaluation thereof. As can be appreciated from comparing the time-differential values with those shown in the lower diagram of FIG. 5(b), the smaller the peak value becomes, the smoother the inclination becomes. This means that the agent decreased the contraction rate of cardiac muscle and therefore the cardiac output is also decreased. In other words, toxicity of an agent on the cardiomyocyte can be evaluated as a decrease in the contraction rate.

Figure 6:
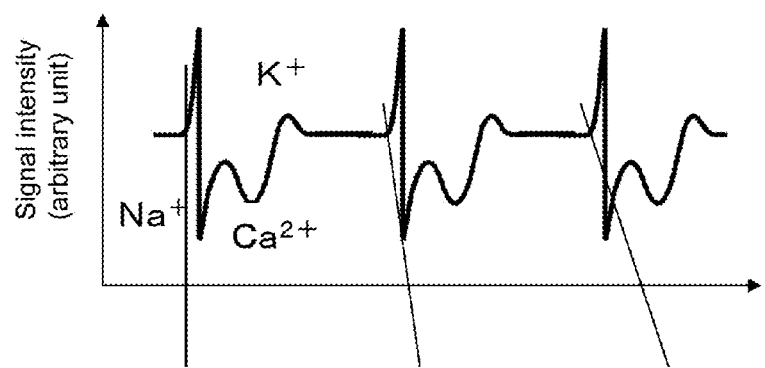
FIG. 6(a) shows changes in the potentials according to the amounts of $Na^+$, $Ca^{2+}$ and $K^+$ ion in- and out-flow into/from the target cells under a normal state where the culture solution is free of agent.
FIG. 6(b) shows changes in the potentials according to the amounts of $Na^+$, $Ca^{2+}$ and $K^+$ ion in- and out-flow into/from the target cells under a state where the culture solution contains an agent.
Figure 6:
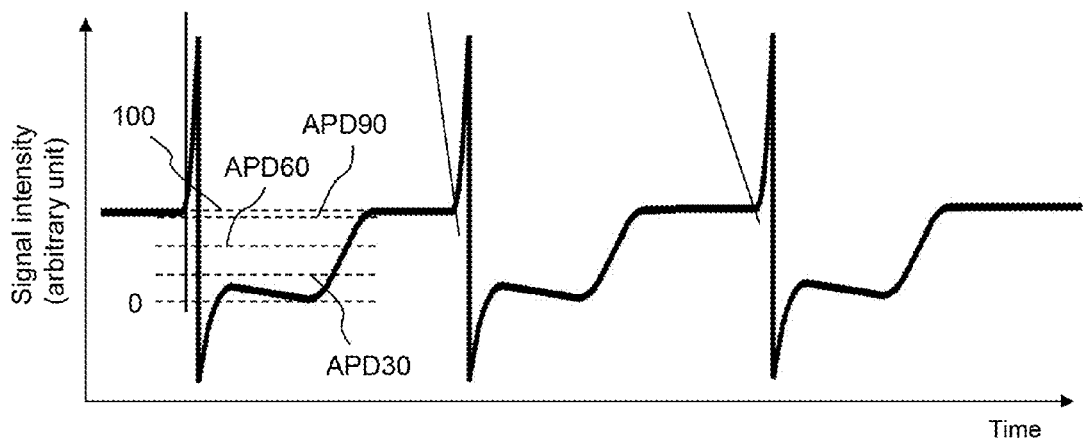

FIG. 6(a) shows changes in the potentials according to the amounts of $Na^+$, $Ca^{2+}$ and $K^+$ ion in- and out-flow into/from the target cells under a normal state where the culture solution is free of agent. FIG. 6(b) shows changes in the potentials according to the amounts of $Na^+$, $Ca^{2+}$ and $K^+$ ion in- and out-flow into/from the target cells under a state where the culture solution contains an agent. As can be appreciated by a cursory comparison of FIGS. 6(a) and 6(b), QT prolongation emerges where the waveform is extended along the time axis. Moreover, the waveform is largely deformed due to in- and out-flow of the $K^+$ ions. In order to evaluate this as an electric signal, the durations of the detected 30%, 60% and 90% values are shown as APD30, APD60 and APD90, respectively, with respect to the broken lines indicating the values between "0" and "100" in the diagram. Here, APD stands for action potential duration. Evaluations of the magnitudes and percentages of these values can provide evaluation of influence of the agent on the amounts of the $Na^+$, $Ca^{2+}$ and $K^+$ ion in- and out-flow.

Figure 7:
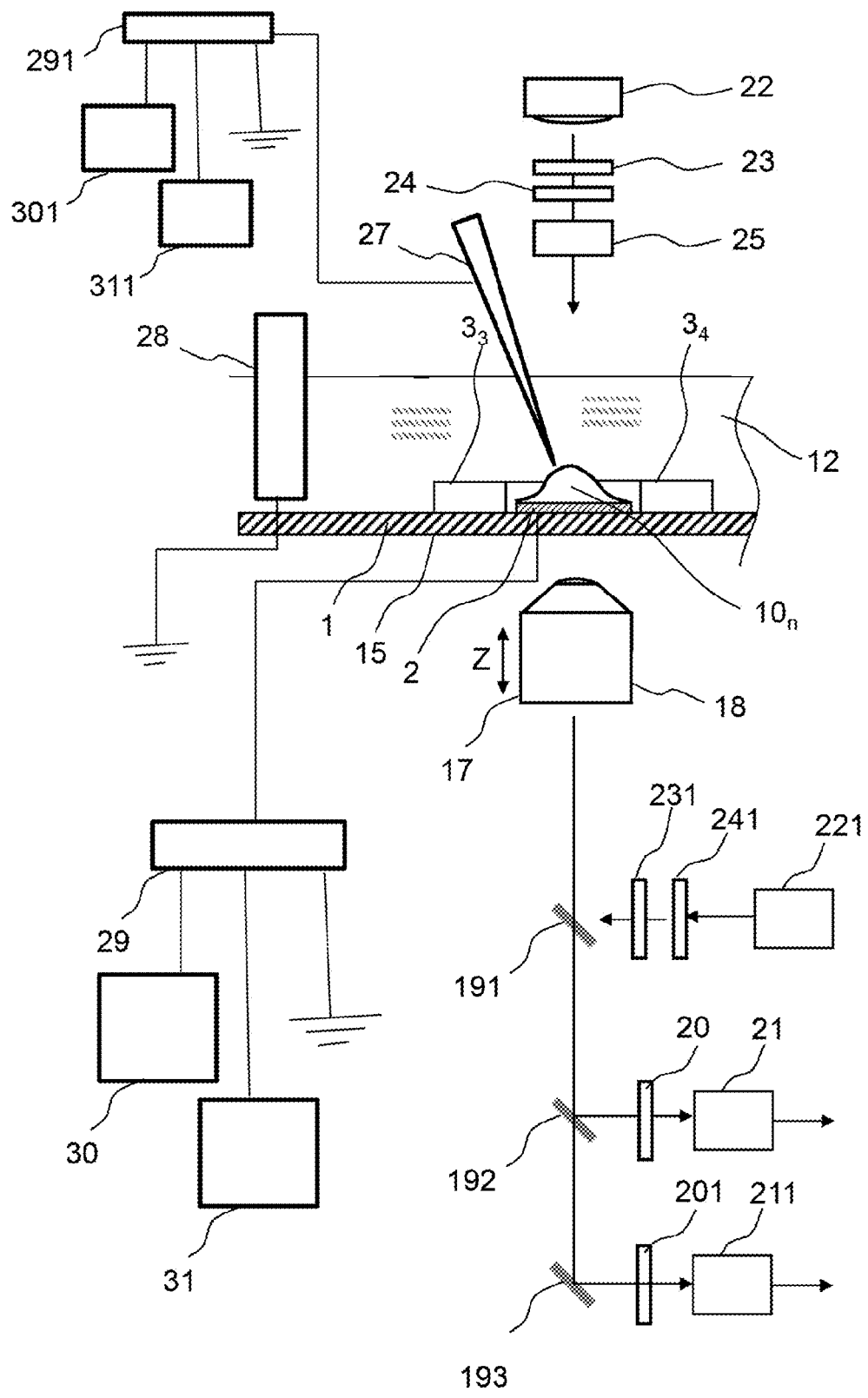
FIG. 7 illustrates an exemplary arrangement of an optical system and a movable electrode of the cardiotoxicity testing apparatus for optically detecting the cells.

FIG. 7 is a view illustrating an exemplary arrangement of an optical system and a movable electrode of the cardiotoxicity testing apparatus for optically detecting the cells, in which observation of the pulsating state, for example, of the cell $10_n$ to be measured is exemplified. Reference numeral 12 denotes a culture solution. Reference numeral 22 denotes light source for a phase-contrast microscope or a differential interference microscope, which is generally a halogen lamp. Reference numeral 221 denotes a fluorescent light source for fluorescent measurement of the cells, which is generally a mercury lamp, a monochromatic laser, an LED light source, or the like. Reference numeral 23 denotes a bandpass filter that allows transmission of only light with a particular wavelength from the light source for observation with a stereoscopic microscope such as a phase-contrast microscope, while reference numeral 231 denotes a bandpass filter that allows transmission of only light with an excitation wavelength that excites particular fluorescence from the fluorescent light source 221. For example, in the case of observing the change in the shape such as information of change in the volume of the pulse of the cell $10_n$, an image that passed the bandpass filter 20 that allows only light with a wavelength for measuring the cell shape is measured with the camera 21 on a real-time basis, where narrowband light having the wavelength in the vicinity of 700 nm is used for measurement to prevent damage of the cell $10_n$. Reference numerals 24 and 241 denote shutters that have a function of blocking irradiation light when image measurement is not executed, for example, while moving the XY stage 15. Reference numeral 25 denotes a condenser lens, where a phase ring is installed for phase-contrast observation or a polarizer for differential interference observation. In the case of fluorescent measurement, for example, in the case of intracellular calcium release measurement, a combination of a bandpass filter that selectively passes light with the excitation wavelength of approximately 500 nm and a bandpass filter that selectively passes light with the fluorescent measurement wavelength of approximately 600 nm is used, to measure, with the camera 201, the fluorescent image that passed through the bandpass filter 201 that only selectively passes light with the fluorescent wavelength. In this case, if calcium release per cell unit in the cell network is to be measured in terms of time to determine the pathway of the signal conduction in the cell network, continuous high-speed images can be acquired with the time resolution of the camera being 0.1 ms or less. The cardiotoxicity testing apparatus 100 formed on the substrate 1 is mounted on the XY stage 15 which can be moved with the X-Y drive unit 16 to observe and measure certain location of the cardiotoxicity testing apparatus 100. The pulsating state of the cell $10_n$ in the cardiotoxicity testing apparatus 100 is observed with an objective lens 17. The focal position of the objective lens 17 can be transferred in the Z-axis direction with a drive unit 18 according to the signal from the personal computer PC. The magnification of the objective lens 17 may be 40 or higher. The objective lens 17 allows observation of a phase-contrast image or a differential interference image of the cell $10_n$ obtained with light transmitted from the light source 22. A diachronic mirror 192 and a bandpass filter 20 that reflect light with the same wavelength as the light that passes through the bandpass filter 23 allow observation of only a phase-contrast microscope image or a differential interference microscope image with a camera 21. The image signal observed with the camera 21 is input into the personal computer PC. Moreover, according to this example, a movable electrode 27 for stimulating a cell is arranged with a position controlling mechanism for adjusting the coordinates of the movable electrode with respect to not only within the plane parallel to the plane of the XY stage but also with respect to its height. Using this position controlling mechanism, the tip of the movable electrode is transferred to stimulate one or more particular cells in the cell network.

The movable electrode may be a metal electrode provided with an insulating coating except for the tip, a glass electrode having the opening size of the tip of about 5 micrometers or less, or the like, where any electrode that can apply electrical stimulation only to a particular cell or cells in the vicinity of the tip of the movable electrode can be used. When a metal electrode is used, platinum black or the like may be applied to the tip surface for effectively transmitting electrical stimulation to the cell(s). The positioning of the tip of the movable electrode can be adjusted according to the level of the response of the cell(s) to the electrical stimulation, and may make a contact with the cell(s) or placed near the cell(s). In addition, in order to accurately apply stimulation from the stimulation electrode to the target cell(s), the electrode 2 for measuring the membrane potentials may be used as a ground electrode by switching the electrode at the moment of applying electrical stimulation, or a separate ground electrode 28 may be provided. Moreover, in order to stimulate a particular cell, the existing microelectrode 2 may be used as a stimulation electrode. In this case, the switching circuit 29 connected to the microelectrode is switched upon stimulation so that the microelectrode that is usually connected to an electric signal measurement circuit 30 is connected to an electrical stimulation circuit 31 for applying square-wave stimulation signals to the microelectrode 2. Furthermore, when the movable electrode 27 is used to provide stimulation, the switching circuit 29 may be switched to a grounding state. On the other hand, the movable electrode may also be used not only as a stimulation electrode, but also as an electrode for measuring the electric signal of the cell(s) or as a ground electrode. In this case, the movable electrode is connected to a switching circuit 291, and switched, according to its use, i.e., for membrane potential measurement, for cell stimulation or as a ground electrode, to be connected to an electric signal measurement circuit 301 to measure the membrane potential, to be connected to an electrical stimulation circuit 311 for applying a square-wave stimulation signal to the cell(s) or to be grounded for use as a ground electrode, respectively. The timings of the electrical stimulation applied to the cells with the electrical stimulation circuits 31 and 311 can be employed primarily for the following two applications. One is to apply irregular stimulations between the pulse intervals of the normal cardiomyocyte network in an autonomous pulsation configuration. The other is to provide pulse interval to the cardiomyocyte network without an autonomous pulsation configuration. In both cases, changes in the response of the cell network can be traced through measurement by gradually shortening the cycle of the pulse interval (time interval between two pulses) by 5 ms. In order to do so, the electrical stimulation circuits 31 and 311 can analyze the pulsation cycle information acquired with the electric signal measurement circuits 30 and 301 and conduct feedback regulation based on the acquired results to determine the timing of the stimulation. Moreover, when the movable electrode 27 is used for the electric signal measurement, measurement can equivalently be carried out in the present system without the microelectrode 2. Since the pulsation cycle of each cell in the cell network can be measured by the optical measurement installed in the system, a change from a stable state to an unstable state such as abnormal cardiac rhythm in this pulsation cycle can be measured only with the optical measurement device arranged in the system. Then, if necessary, the movable electrode is used to acquire the data of the electric property of the particular cell from these results. In this case, the number of the microelectrodes arranged on the system in the first place is not limited, and a larger cell network can be configured freely as long as optical measurement is possible.

Figure 8:
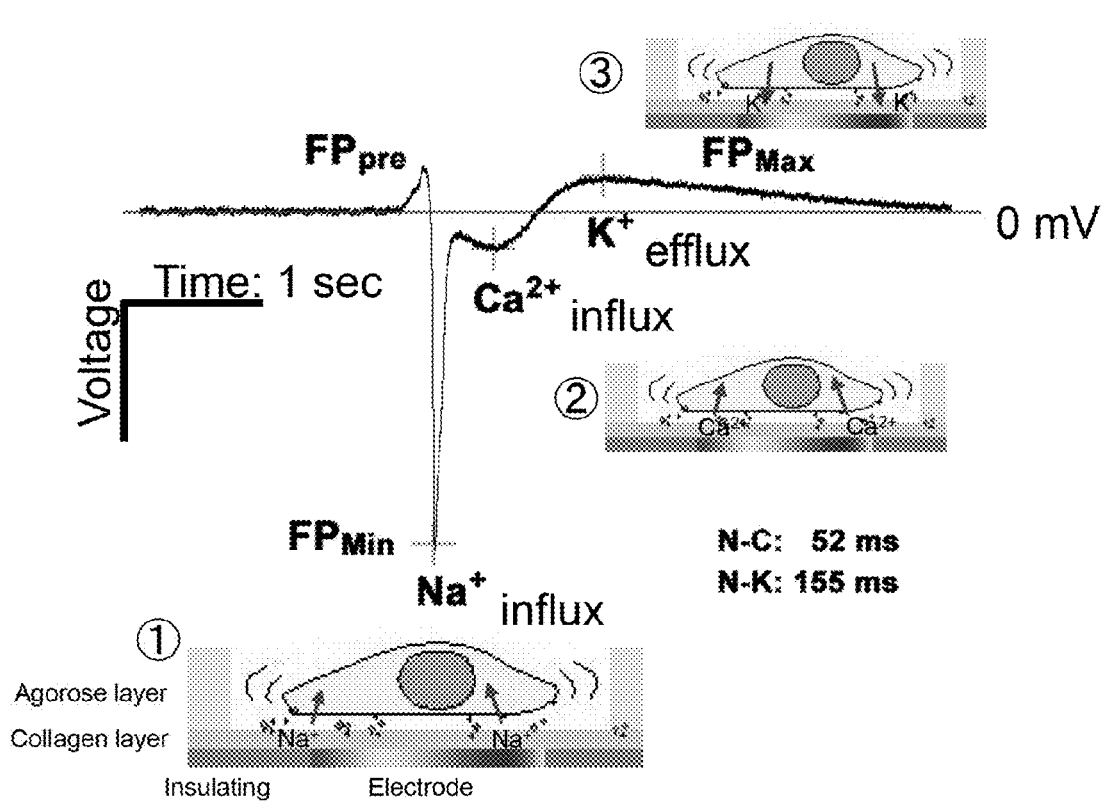
FIG. 8 is a schematic view for illustrating generation of an electric signal of a cell.

FIG. 8 shows a schematic view of an example of generation of an electric signal of a cell. First, inflow of sodium ions into a cell occurs via sodium-ion channels on the cellular membrane, where the membrane potential is rapidly decreased. Then, the membrane potential is decreased after a slight delay due to inflow of calcium ions, and then as the subsequent step, outflow of potassium ions from the cell occurs where the membrane potential is increased. The changes in the membrane potentials occur due to the different response imparted by the properties of various ion channels present in the cardiomyocyteular membrane. By analyzing the positions of the peaks of change in the potentials caused by the respective ion channels as time characteristic of the ion channels, the changes in the waveforms of the electric signals can be measured for each type of the ion channels that are blocked due to the effect of the agent. As a result, inhibition effect of the agent on the ion channels can be estimated. There are four particularly important ion channels for evaluation of an agent, i.e., FastNa, SlowNa, Ca, IKr and IKs. Blocking of these four types of ion channels can be measured.

Figure 9:
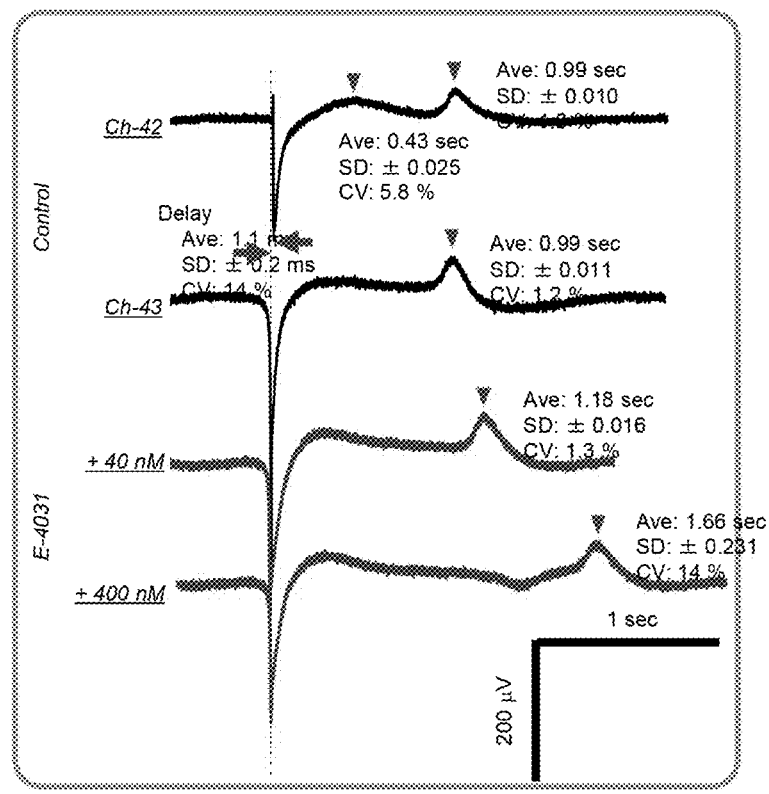
FIG. 9(a) shows an exemplary change in the membrane potentials upon addition of an agent.
FIG. 9(b) shows one example of Poincare plots for evaluating homology between two successive pulses with respect to the change in the membrane potentials upon each pulsation.
Figure 9:
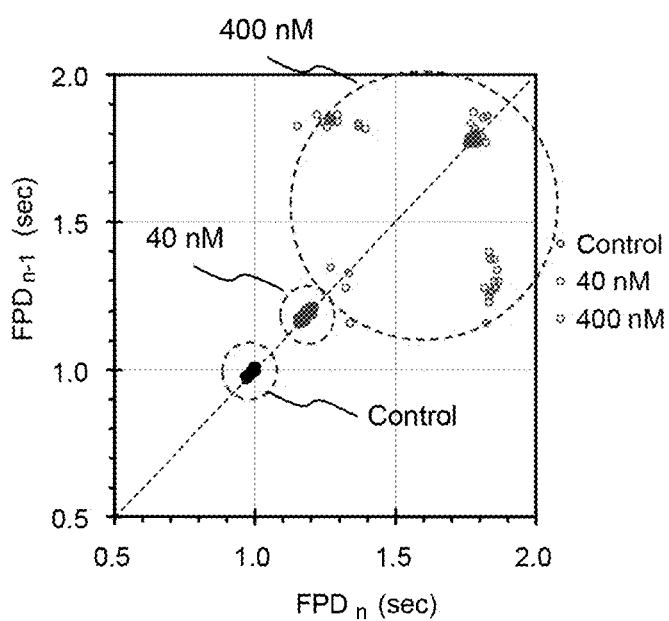

FIG. 9(*a*) shows influence on the electric signals of the cell shown in FIG. 8 upon actual addition of reagent E-4031 at various concentrations that selectively inhibits the potassium-ion channels. Since the IKr-ion channel that is responsible for outflow of K-ion from the cells and that increases the membrane potential is inhibited, a change in the membrane potentials can be observed to be gradually delayed in the positive direction as the concentration of the agent increases. FIG. 9(*a*) shows data of a particular single pulsation of a cellular response. In practice, the magnitude of the fluctuation width of the responses between the successive pulses is an important index for estimating the influence of the agent. FIG. 9(*b*) shows one example of an analysis technique where successive pulse data called Poincare plots are compared correlatively. Here, X-axis represents plots of response time of a particular ion channel upon the n-th pulse while Y-axis represents plots of the response time of the same ion channel upon the (n+1)-th pulse. Accordingly, if the properties of the successive pulses are the same, the plots will be drawn along the Y=X line represented by the broken line in the graph. If there is a significant fluctuation in the responses between the successive pulses, the plots observed will be placed distant from the Y=X line. In fact, in this example, although addition of 40 nM results in the delay of the response time as compared to the control without addition of the agent, homology between the successive pulses remains the same. At the same time, these plots reveal that addition of the agent up to 400 nM further delays the response time, and homology is no longer retained between the successive pulses, resulting in generation of an unstable pulsation cycle. This result agrees with the results of prolongation in the QT interval measurement representing cardiac toxicity. Generation of a prolongation of the QT interval can be estimated by using the Poincare plots as an index of increase in the fluctuations of the successive pulses at a cellular level. This phenomenon can be described as follows: when a particular ion channel is blocked with an agent, only a phenomenon of decrease in the ion outflow ability is observed where the degree of the blocking is small and the cell response is not yet unstable. In contrast, when the degree of blocking increases as the number of functioning ion channels becomes extremely decreased, the reproducibility of the ion outflow ability deteriorates and fluctuation for the same cell increases. Hence, the magnitude of this fluctuation can be used as an index of likelihood of generating a prolongation of QT interval.

Figure 10:
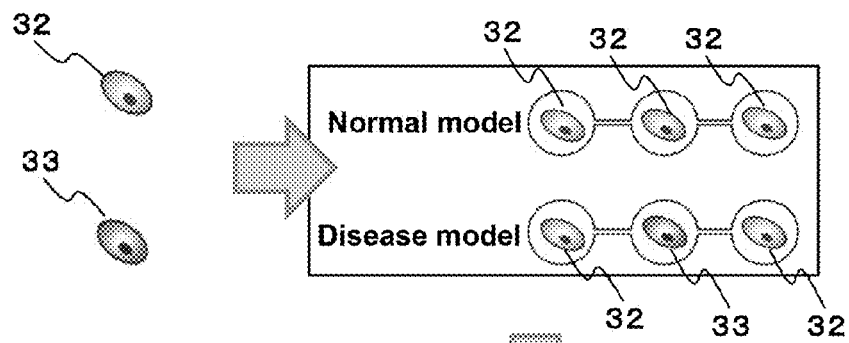
FIG. 10(a) is a schematic view showing an exemplary re-entry circuit prepared with an annular network of cardiomyocytes by means of a cell arrangement technique at single-cell level.
FIG. 10(b) is a micrograph showing an actual exemplary arrangement of the cells on the microelectrodes.
Figure 10:
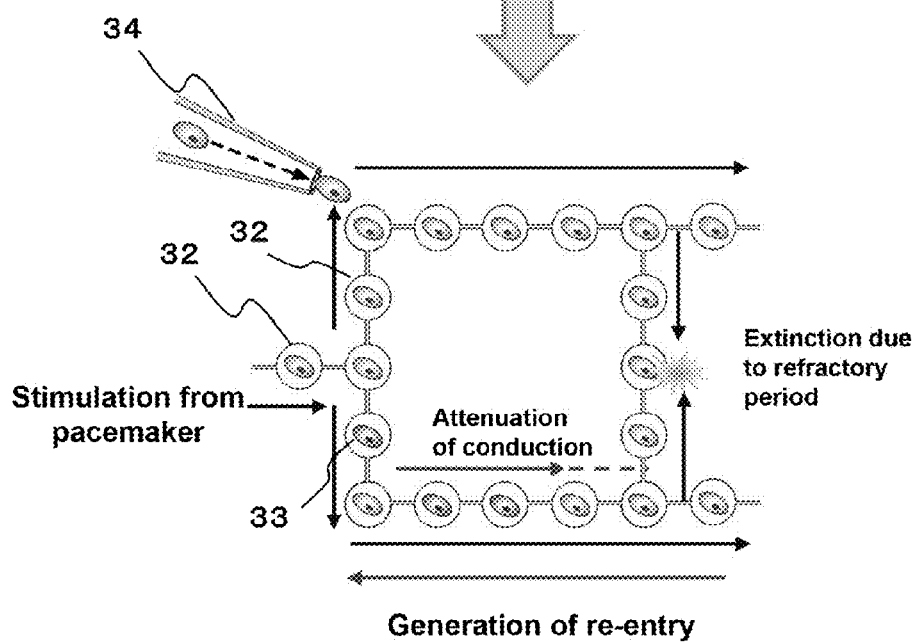
Figure 10:

FIG. 10(a) is a schematic view showing an example of an agent for a re-entry circuit with an annular network of cardiomyocytes using a cell arrangement technique at a single-cell level. An annular network produced with only cardiomyocytes is used as a normal network model. A pathologic model such as cardiac hypertrophy is realized by incorporating fibroblast cells into the cell network. The fibroblast cells present in the network will cause delay of the conduction velocity or attenuation of the conduction of the cardiomyocyte network, as a result of which, generation of premature contraction can be estimated. FIG. 10(b) is a microscopic picture showing an example of actual arrangement of cardiomyocytes on the microelectrodes. In fact, when the cells are arranged on the microelectrodes in cell units as shown in this picture, delay in the signal conduction between the adjacent cardiomyocytes can be measured. Since this conduction velocity depends on the magnitude of the first electric signal generated upon pulsation, data for delay in this signal conduction can be interpreted as the inhibitory effect on the sodium-ion channel.

Figure 11:
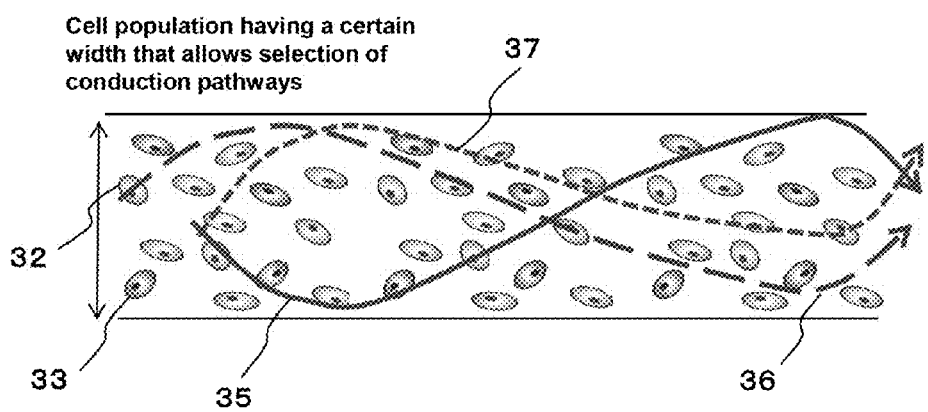
FIG. 11(a) is a schematic view showing an exemplary re-entry circuit prepared with an annular network of cardiomyocytes using a cell population having a certain width.
FIG. 11(b) is a microscopic picture showing an actual exemplary arrangement of the cells on the microelectrodes.
FIG. 11(c) is a microscopic picture showing an actual exemplary annular arrangement of the cell population on the microelectrode array.
Figure 11:
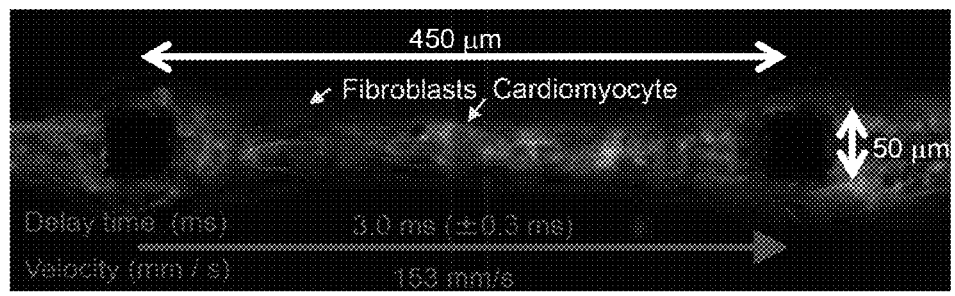
Figure 11:
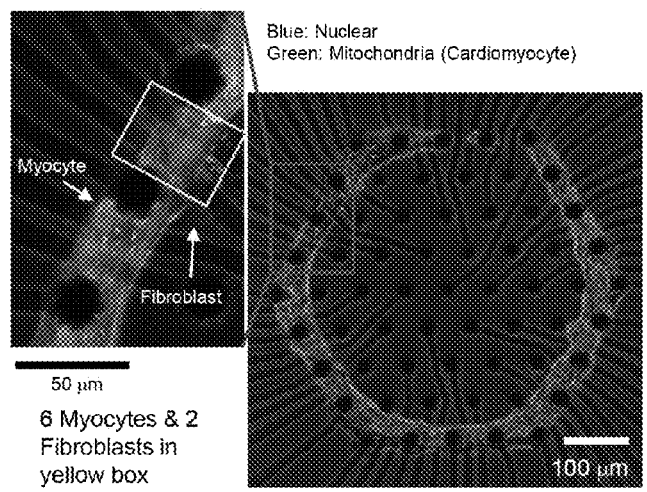

FIG. 11(a) is a schematic view showing an exemplary re-entry circuit by an annular network of cardiomyocytes using a cell population having a certain width. In the annular cell network in cell units shown in FIG. 10, pulsation signals of the cardiomyocytes are uniquely transmitted, and the cells will transmit pulsation signals between the adjacent cells while maintaining the same property unless there are fluctuations in the pulses of the cells themselves as shown in FIG. 9. On the other hand, when the cells were arranged with a certain width to form an annular network as shown in FIG. 11, the cell population will be imparted with the flexibility to have different conduction pathways for different pulses as represented by solid line 35, broken line 36 and dotted line 37. In particular, when a large fluctuation occurs in the response property of each cardiomyocyte due to the addition of an agent as described with reference to FIG. 9, the cells that are likely to respond differ in response to the travel of the stimulation signals through the annular network, thereby rendering the difference in the pathways significant. Since this is the same mechanism as the mechanism of premature contraction, i.e., a fatal cardiac status called spiral/re-entry, measurement of spiral/re-entry becomes possible by particularly using an annular network based on cell population having such a width. FIG. 11(b) is a microscopic picture showing an actual exemplary arrangement of the cell population on the microelectrodes, in which the cell population has about 60% cardiomyocytes and about 40% fibroblasts. In fact, such an arrangement increases fluctuations between successive pulses in the conduction velocity between adjacent electrodes. Since the increase in the fluctuation becomes significant particularly by the addition of the agent, generation of spiral/re-entry can be estimated according to the change in the fluctuation width of the conduction velocity between successive pulses. FIG. 11(c) is a microscopic picture showing another example of actual annular arrangement of the cell population on the microelectrode array. For actual measurement of spiral/re-entry, calcium spike firing in each cell of the cell population network can be estimated at the single-cell level by using the high-speed fluorescent measurement camera shown in FIG. 7. As a result, actual analysis of the pathway taken by the signal conduction of the cells and actual analysis of the change in the pathways at each round can be realized.

FIG. 12(a) is a schematic view showing an exemplary re-entry circuit measurement device using an annular electrode. In this example, an annular electrode 38 with an electrode width of 50-100 micrometers is formed into a ring shape to have a diameter of 1-3 mm and arranged on each of the bottom surfaces of a 96-well plate 42. The bottom surface of the plate other than the electrode is coated with a non-cell-adhesive material such as agarose so that the cell population 41 is annularly placed only on the electrode surface. A reference electrode ring 39 is placed concentrically on this non-cell-adhesive coated region, and a flow passage 40 is provided for entrance and exit of a reagent. By using such an electrode, abnormal pulsation of a cardiomyocyte can be simply and conveniently measured. FIG. 12(b) is a graph showing normal pulse data and abnormal pulse data actually measured with the electrode. Although an annular electrode is used in this example, a system for optically measuring abnormal pulsation which is equivalently effective as this annular electrode can be constructed by using the optical measurement system shown in FIG. 7. In this case, an electric signal to be measured can be acquired by allowing the moving electrode shown in FIG. 7 to make contact with the annular cell network.

Figure 13:
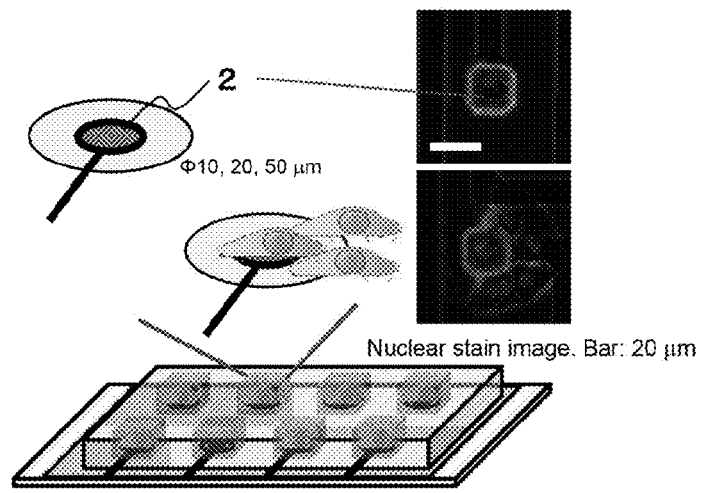
FIG. 13(a) is a schematic view showing an exemplary arrangement of an electrode for measuring potentials of a single cell and the cell.
FIG. 13(b) shows a picture of the isolated single cell on the electrode actually measured with the electrode and electric pulse data thereof.
FIG. 13(c) shows a picture of a cell population measured on the electrode and a graph showing electric pulse data of one of the cells of the cell population.
Figure 13:
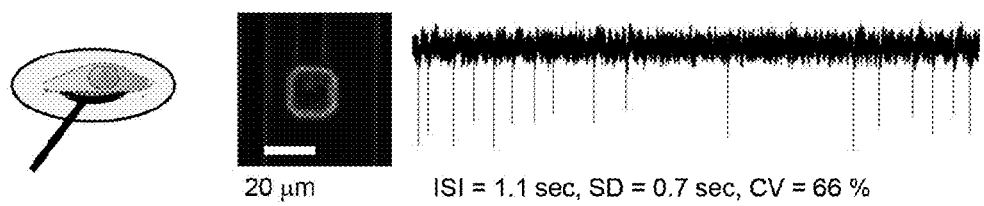
Figure 13:
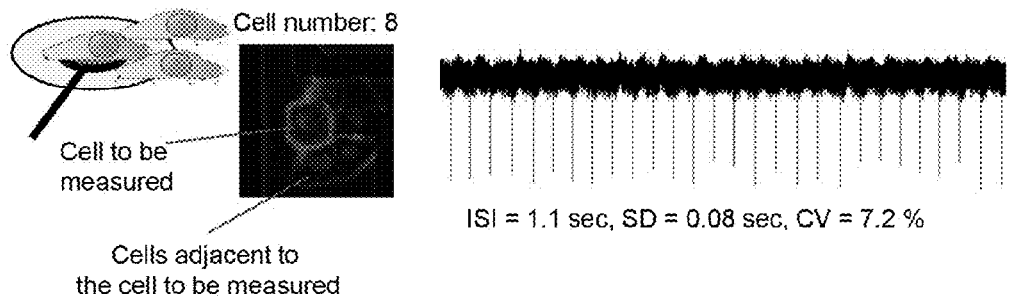

FIG. 13(a) is a schematic view showing an exemplary arrangement of a cell and a microelectrode 2 for measuring a potential of a single cell, which illustrates a measurement technique in which a single cell targeted for measurement is arranged on the microelectrode 2 with a diameter of 10 to 50 micrometers. Again in this example, likewise in other examples, the area of the bottom surface other than the electrode is coated with a non-cell-adhesive material such as agarose such that the cell is retained on that place on the electrode. FIG. 13(b) is a view of an isolated single cell on the electrode which was actually measured with the microelectrode 2, and electric pulse data thereof. Signals from the isolated single cell are unstable and pulses undergo a large fluctuation as shown in the graph. On the other hand, in FIG. 13(c), a single cell is placed on the microelectrode 2 like FIG. 13(b) but to form a cell population with other cells, thereby realizing stability of the pulsation cycle as can be appreciated from the pulsation signal graph. In an actual pulse measurement at the single-cell level, the magnitude of the fluctuation between successive pulses serves as an index as shown in FIG. 9. Therefore, as described in the present example, a measurement system is useful in that only a specific cell to be measured is placed on the microelectrode while other cardiomyocytes are not provided on the electrode to thereby maintain stability of the specific cell. Accordingly, pulse data of a single cell can be acquired while realizing stability by providing a cell population.

Figure 14:
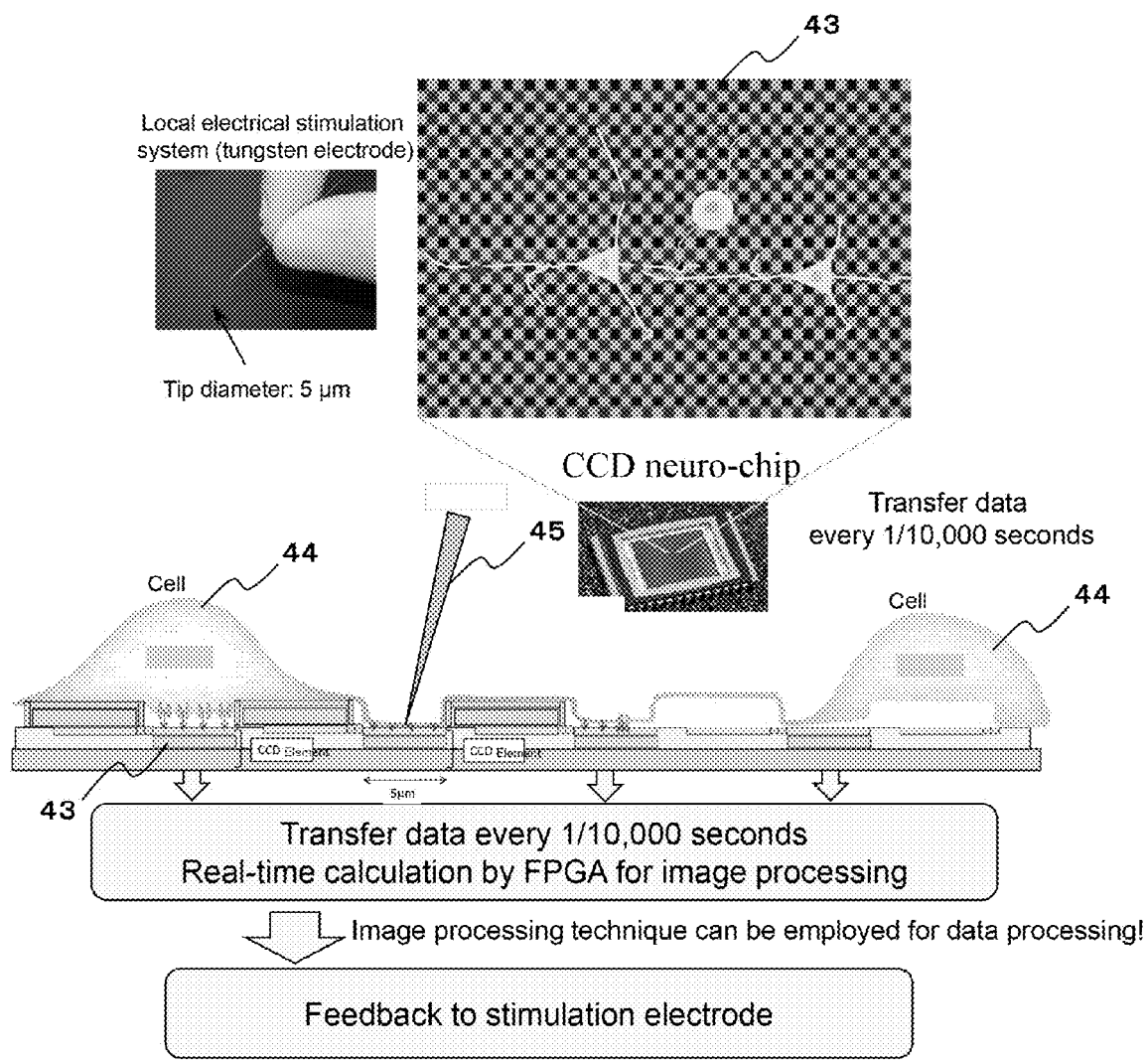
FIG. 14 is a schematic view illustrating an example of the present invention in which a photo-sensitive element of the camera is used for measuring potentials of a single cell.

FIG. 14 is a schematic view for illustrating an example using a photo-sensitive element of the camera for measuring a potential of a single cell according to the present invention. In general, a photo-sensitive element of the camera converts a light signal into an electric signal on a photoelectric conversion surface to use this electric signal for measurement. This photoelectric conversion surface can be removed and an electric signal array can be used to obtain an electric signal in two dimensions. Therefore, since an electrode array at the single-cell level can be used, for example, a change in the signal conduction pathway in the cell population network with certain spaced intervals as shown in FIG. 11, i.e., generation of spiral/re-entry, can be measured, which requires simultaneous measurement of electric signals of respective cells in the cell population. The required interval for pixel measurement in an actual measurement is about 1/10,000 seconds, and thus a photo-sensitive element of a high-speed camera with a shutter speed of 1/10,000 seconds is required. In this case, an image processing technique employed in conventional cameras can directly be applied to the acquired signal data of the cells, which allows real-time processing using FPGA for image processing. In addition, feedback stimulation can be applied to the stimulation electrode based on the data obtained by this real-time processing.

Figure 15:
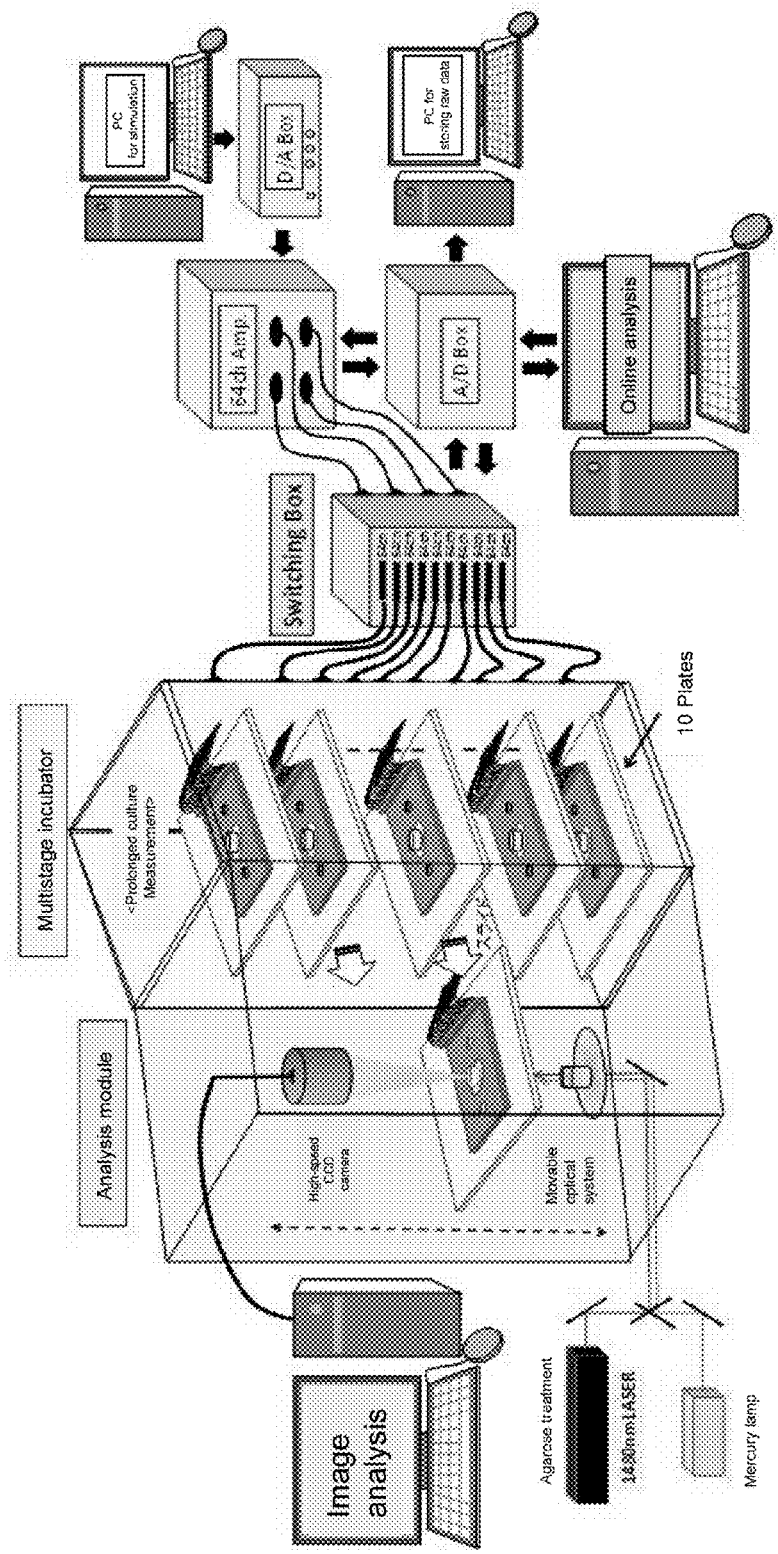
FIG. 15 is a schematic view illustrating an exemplary mechanism for measuring a plurality of samples with a cell measurement system of the present invention.

FIG. 15 is a schematic view for illustrating an exemplary mechanism for measuring a plurality of samples with a cell measurement system of the present invention. The system of this example comprises an analysis module, a multistage incubator, an electroanalysis module and an online analysis module connected thereto via an online network. Here, the analysis module comprises a phase-contrast microscope or a differential interference microscope for measuring changes in the cellular shape, optical measurement means associated with a fluorescent microscope and a camera photography analysis, and an agarose processing technique that can locally dissolve agarose at a micrometer scale with a microscopic system. Multiple cell culture baths are arranged in the multistage incubator, where microelectrode chips are arranged in the cell culture bath such that measurement of electric signals of each cell and electrical stimulation can be sequentially processed in parallel in the incubator. The obtained electric signals are subjected to real-time measurement in the electroanalysis module, and resulting data are recorded in a storage that is accessible online such that the results of optical measurement data and electric measurement data are recorded with the same time stamp. The analysis module can appropriately access to these record data online for analysis.

Figure 16:
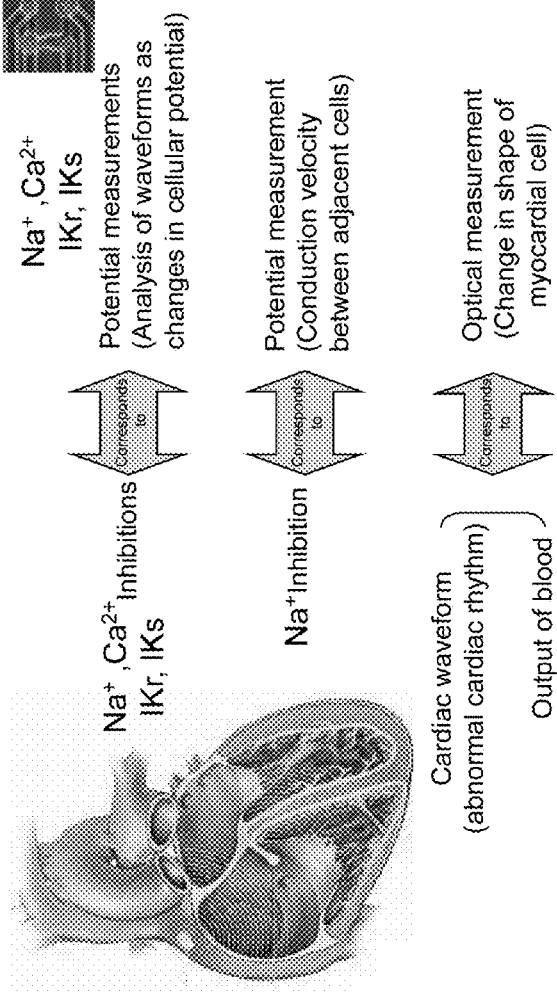
FIG. 16 is a schematic view illustrating cardiac information that can be measured with a cell measurement system of the present invention.
Figure 16:
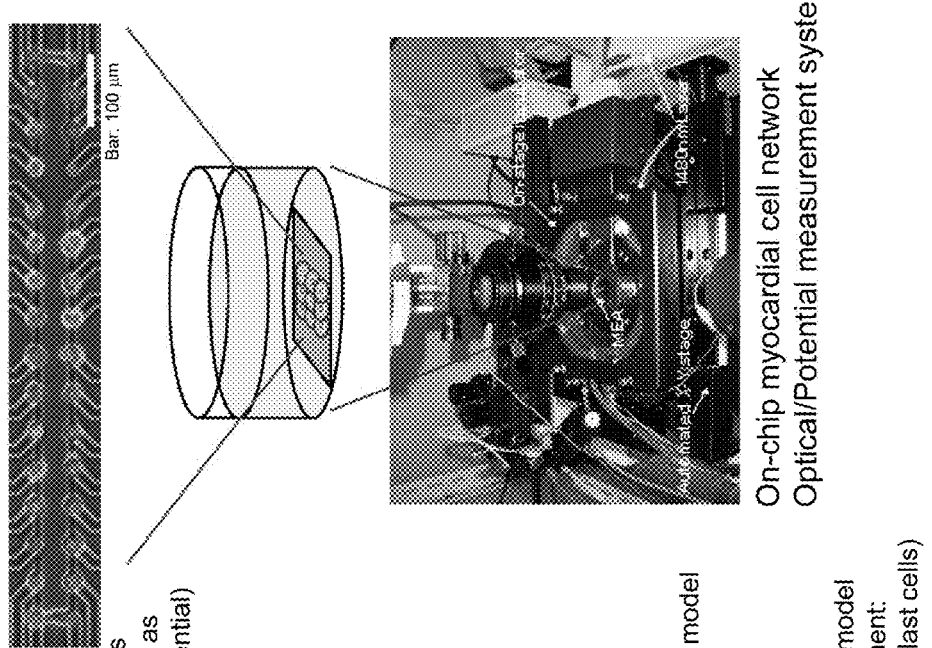

FIG. 16 is a schematic view for illustrating information of heart measured with a cell measurement system of the present invention. Electric signal measurement for a single cell on a microelectrode enables measurement of signal data of ion channels such as Na-, Ca-, IKr- and IKs-ion channels and sodium-ion channel inhibition can be measured by measuring the changes in the signal conduction velocities between adjacent cardiomyocytes. In addition, optical measurement of the change in the shape of a single cell allows measurement of the generation of abnormal cardiac rhythm as well as estimation of cardiac output. Furthermore, generation of re-entry can be measured by annularly arranging the cell network. Moreover, measurement as a cardiac pathologic model such as cardiac hypertrophy can be realized by adding fibroblast cells to the cell arrangement.

Figure 17:
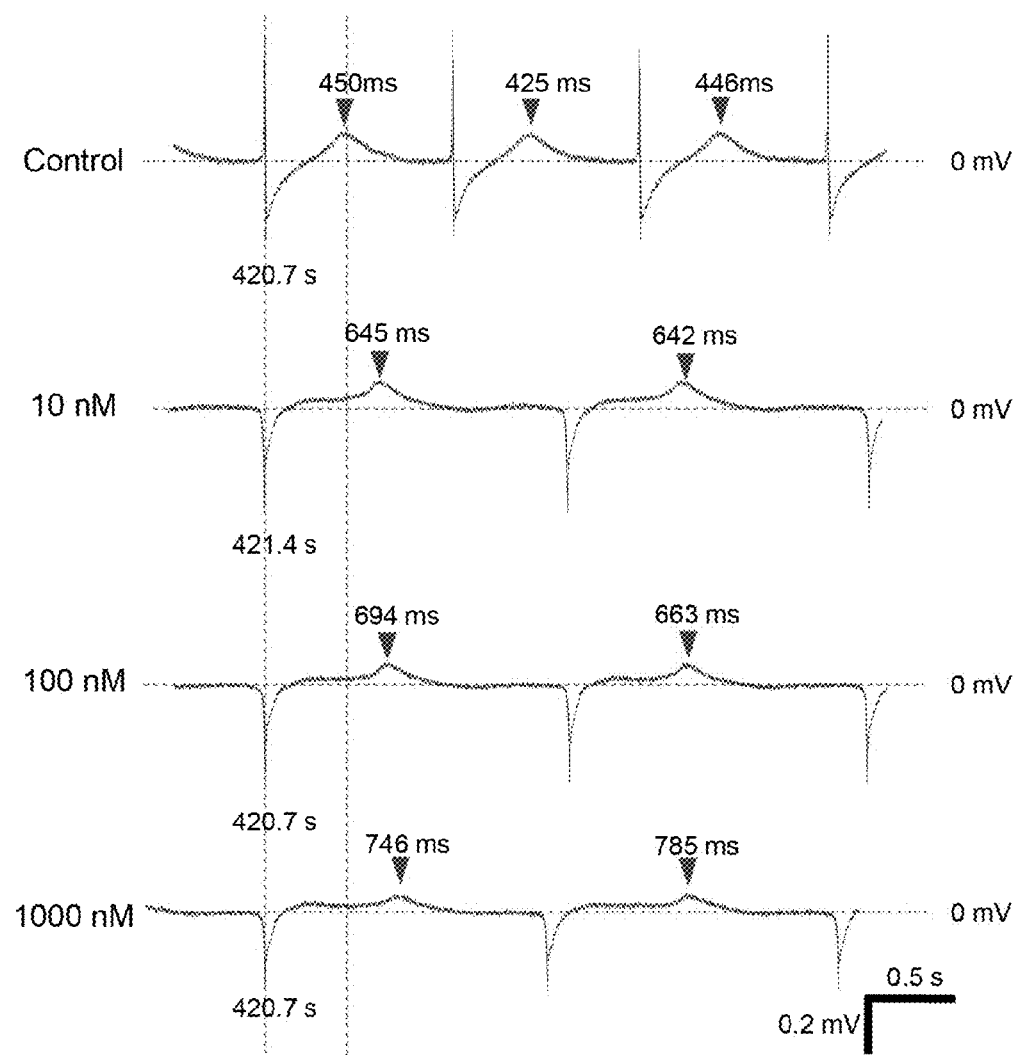
FIG. 17 is an example of a graph illustrating the addition of the agent changes to the field potential signal waveform of the cells measurable by the measurement system of the present invention cells.

FIG. 17 is a graph illustrating an example of changes in the field potential (FP) signal waveform of cells obtained from autonomously pulsating cardiomyocytes in response to the addition of agents in accordance with the cell measurement system of the present invention. The signal waveform of the field potential of the cells shows a change in a membrane potential generated by ions flowing into the cells and ions flowing out of the cells as shown in FIG. 8. The signal waveform represents a differential value of the membrane potential, i.e. the sum of an ion current flow per unit time. In this case, the inward ion current, such as sodium or calcium ions or the like in the process leading to depolarization, tends towards negative, and the outward ion current, such as potassium ions in the subsequent process of repolarization, tends towards positive. As shown in FIG. 17, information for the FP signal waveform of the cells is usually extracted as one FP waveform as a mean value of a plurality of adjacent waveforms to eliminate the effects of noise components or differences in adjacent waveforms, rather than focusing on the differences between each other for each adjacent pulsation, and detailed analysis of one waveform reflecting the average value is used to estimate the state of each of the ion channels. However, in the present invention, rather than acquiring the average value of the adjacent FP signal waveforms, the adjacent FP signal waveforms are compared and any difference due to the fluctuation of the response of the ion channel is extracted. Based on the size of the fluctuation, the amount of the blocked ion channel is estimated quantitatively. The magnitude of the fluctuations is in general represented by $[1/(n)^{1/2}]$, the reciprocal of the square root of n elements, to facilitate comprehension thereof. That is, given that when $10^4$ channels of the number of ion channels in the cell surface are working, for example, the magnitude of the fluctuation of the function as a sum of the ion channels will be 1% $[1/(10^4)^{1/2}]$, while if the number of the working ion channels decreases to $10^2$ due to blockage by an agent, then the magnitude of the fluctuation increases sharply to 10% $[1/(10^2)^{1/2}]$, resulting in a big change in its feature of the adjacent FP waveform. In other words, if it is possible to estimate the magnitude of the fluctuation by comparing the change in the adjacent FP waveform, then the total amount of ion channels that are blocked can be estimated from the magnitude of the fluctuation.

For the change of the adjacent waveform, focusing on the location of the peak of the outward ion current generated by the release of potassium ions, in particular, taking the time at which sodium ions flow into the cell as a reference (zero), for example, and defining the time from the reference point to the peak of the emission potassium ions as field potential duration (FPD), then the change in the length of the FPD will be the peak value of the inflow of potassium ions subsequent to in- and out-flows of ions such as sodium ions and calcium ions. It can thus be used as an indicator of the amount of change as the sum of the change in in- and out-flows of the ions generated by blocking of various ion channels on cells by an agent. In addition, this fluctuation of the position of the FPD reflects the sum of the fluctuations of the adjacent FP waveforms of all the involved ion channels of the cell. In fact, when the position of the FPD (position of the red arrowhead) in FIG. 17 is checked, it is seen that the FPD is between 425-450 ms prior to the addition of E4031, which is an inhibitor of potassium ion channels, but then became 642-645 ms due to the addition of 10 nM, 663-694 ms due to the addition of 100 nM, and 746-785 ms due to the addition of 1 μM E4031. Thus, the value of the FPD increased monotonically due to the addition of the inhibitor. Consequently, adjacent FPDs will not take the same value, but will take a different value to reflect the fluctuation.

Figure 18:
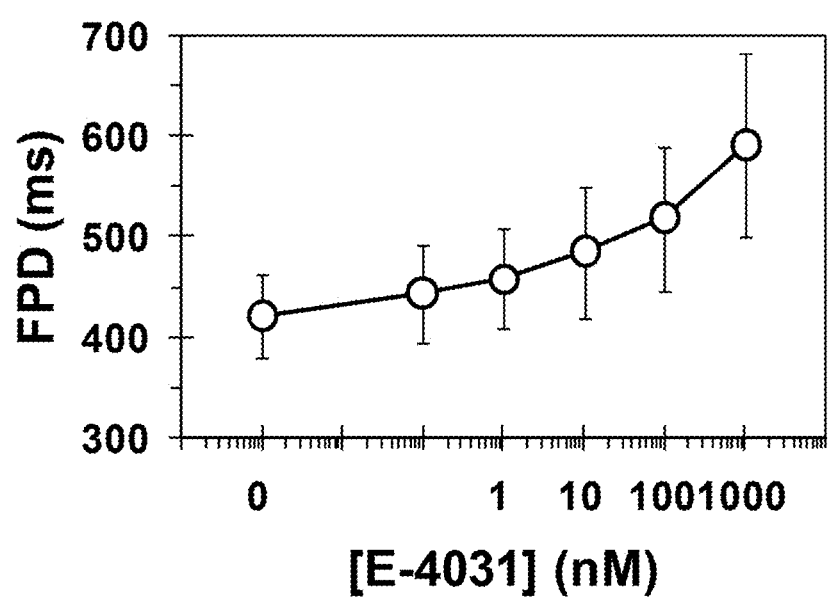
FIG. 18 is an example of a graph illustrating an example of the average value of the changes in response to the addition of a potassium ion channel inhibitor E4031 in connection with elapsed time (FPD: field potential duration) of the peak position of the release of potassium ions from the release time of sodium ions in the signal waveform of the field potential of the cells that can be measured by the cell measurement system of the present invention.

FIG. 18 shows an actual example of the experimental results of E4031-concentration-dependency on the prolongation of the FPD when potassium ion channels of the cell were inhibited by an E4031 agent having the ability to specifically inhibit potassium ion channels. Here, it is estimated that the ion outflow is delayed by the inhibition of the potassium ion channels, and the FPD is prolonged in a concentration-dependent manner. Next, measurements of fluctuations in relation to the results of this experiment will be described in the same manner as above.

Figure 19:
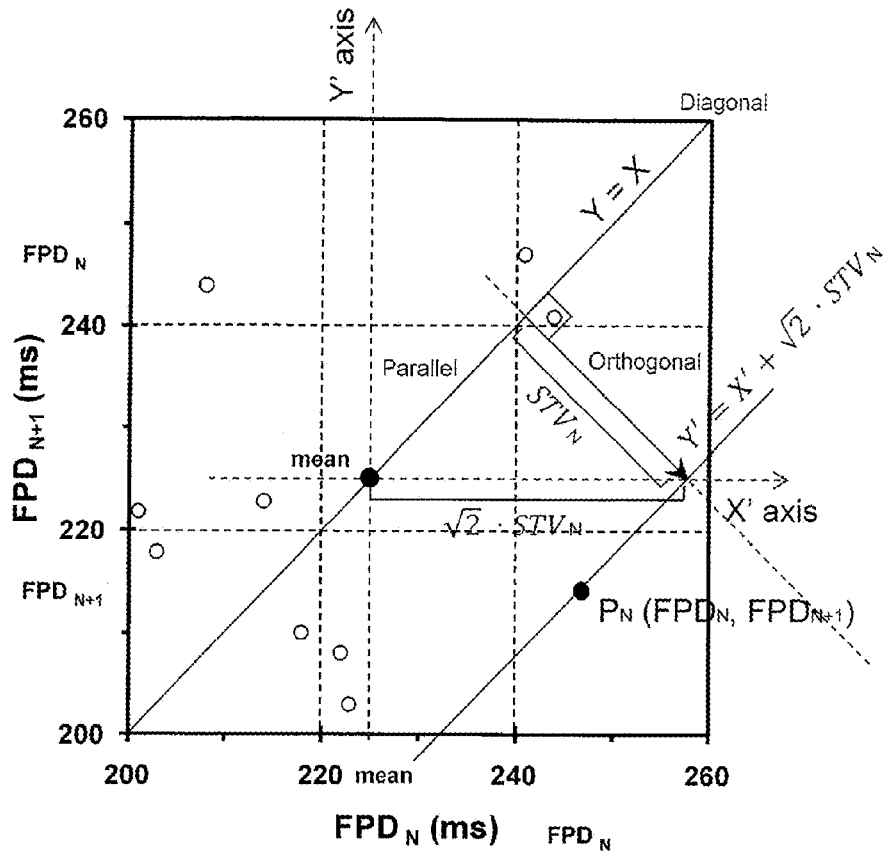
FIG. 19 is an example of a graph and a formula illustrating one of the methods for evaluating quantitatively the size of fluctuation of short-term variability of adjacent pulsations on the basis of Poincare plotting in connection with elapsed time (FPD: field potential duration) of the peak position of the release of potassium ions from the release time of sodium ions in the signal waveform of the field potential of the cells that can be measured by the cell measurement system of the present invention.

FIG. 19 illustrates the estimation of the magnitude of the fluctuation of the adjacent pulsations (short-term variability: STV) among other points of interest in estimating to what extent the FPD of adjacent pulsations shift from a homologous state when the fluctuation of the FPD is observed using the Poincare plotting for measuring the fluctuation of pulsation in the electrocardiogram in general to evaluate the value of the FPD in the FP waveform. In FIG. 19 (*a*), the diagonal, in which X=Y, corresponds to the case where the size of adjacent pulsations $FPD_n$ and $FPD_{n+1}$ have exactly the same FPD size, and the vertical distance of the magnitude of the difference between two FPDs (i.e., $FPD_{n+1}-FPD_n$) from the diagonal is the size of the standardized fluctuation of the adjacent pulsation itself. In particular, for the number of samples "k", it can be evaluated by a formula such as the formula (I) shown in FIG. 19 (*b*).

Figure 20:
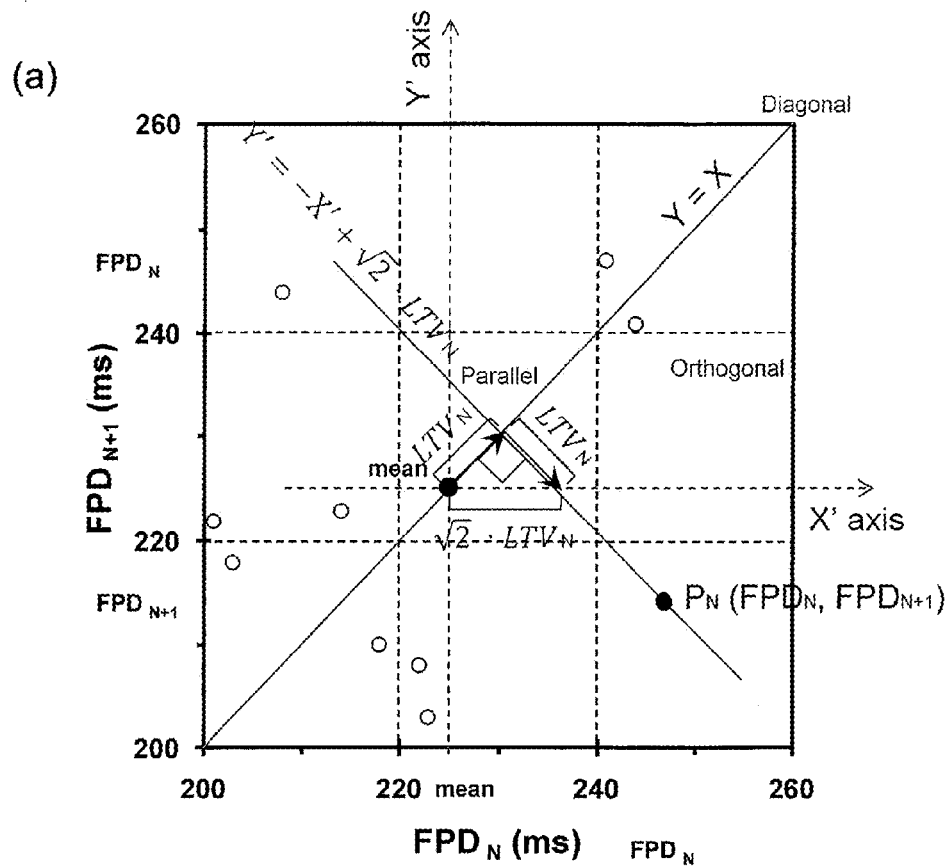
FIG. 20 is an example of a graph and a formula illustrating one of the methods for evaluating quantitatively, based on Poincare plotting, the size of the fluctuation of elapsed time (FPD: field potential duration) of the peak position of the release of potassium ions from the release time of sodium ions in the signal waveform of the field potential of the cells that can be measured by the cell measurement system of the present invention.

On the other hand, FIG. 20 illustrates, among other methods for estimating to what extent the FPD of adjacent pulsations shifted from a homologous state, how to estimate the magnitude of the fluctuation of pulsations (: Long-Term Variability: LTV) in terms of to what extent each adjacent pulsation is shifted from the average value of the pulsations (the sum of all samples and corresponding to the ideal value of the response of the ion channel) when the fluctuation of the FPD is observed using the Poincare plotting. In FIG. 20(*a*), the magnitude of $[(FPD_{n+1}-FPD_{mean})+(FPD_n-FPD_{mean})]$, which are the two distance values between two FPD values, i.e., adjacent pulsation $FPD_n$ and $FPD_{n+1}$, respectively, and $FPD_{mean}$, the average value of the FPD, which corresponds to the diagonal X=Y, is the magnitude of fluctuation from the mean value of the FPD and the vertical distance from the diagonal which has been normalized. In particular, with respect to the number of samples "k", it can be evaluated by the formula 2 of FIG. 20 (*b*). This shows the deviation from the symmetry of X=−Y, and this size can be used as an index to find out whether or not it is merely a fluctuation of beating near the average value, or whether there is an historical correlation.

Figure 21:
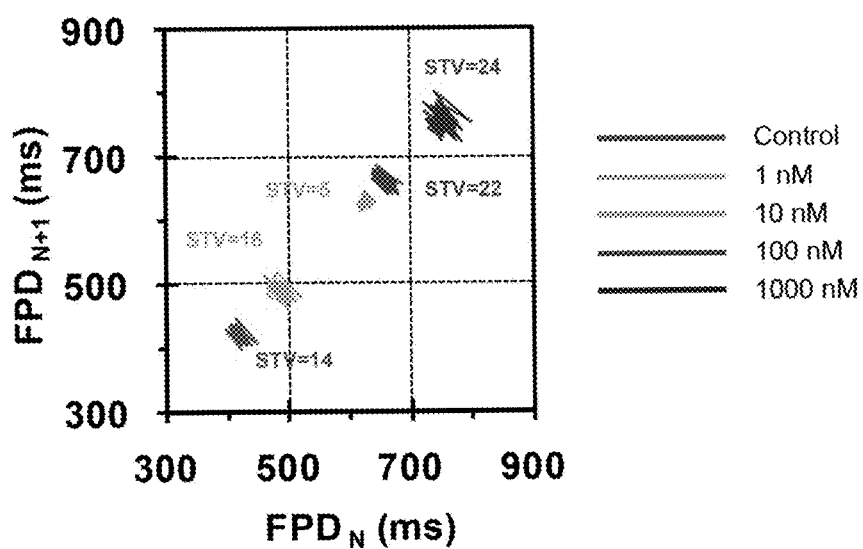
FIG. 21 is an example of a representation of the size of the fluctuation produced by the addition of EE4031 in (a) Poincare plotting and (b) STVs in connection with elapsed time (FPD: field potential duration) of the peak position of the release of potassium ions from the release time of sodium ions in the signal waveform of the field potential of the cardiomyocytes that can be measured by the cell measurement system of the present invention.
Figure 21:
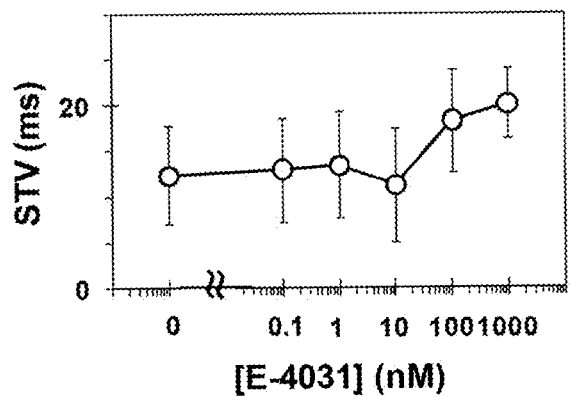

FIG. 21 shows, in Poincare plotting, one example of the fluctuation of the FPD of the response of cardiac muscle cells when E4031 was actually added stepwise; and a quantitative summary as STV. It can be seen that it is estimated that ion channels are blocked in response to the addition of E4031 by an prolongation of the length of time of the FPD, while the value of the STV increases rapidly by, in particular, the addition of high concentrations.

Figure 22:
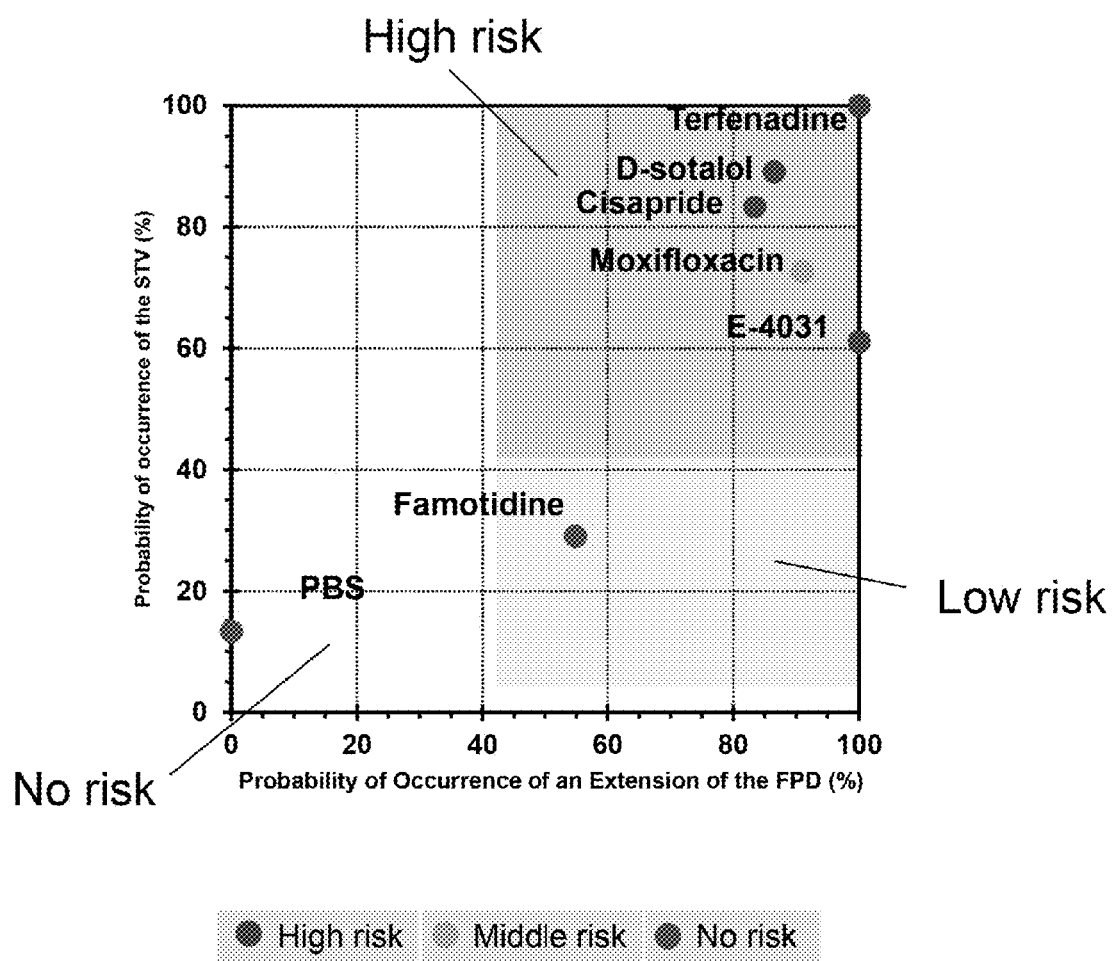
FIG. 22 shows FPD and STV in the case of adding agents known to have a variety of cardiotoxicities on cardiomyocytes and a reference agent measurable by the measurement system cells of the present invention.

FIG. 22 shows an example of an evaluation of chemical agents that are known to have cardiac toxicity and that are known to have no cardiac toxicity wherein the X-axis is the percentage (%) of observed prolongation of the FPD using the cardiomyocytes, which corresponds to conventional measurement of QT prolongation, and the Y-axis is the percentage (%) of observed increase in the STV. In a conventional toxicity test of agents, the evaluation had been made only with the results of the data of the FPD on the X-axis. When the evaluation is made with additional results of the STV on the Y-axis, as can be seen from the figure, it is found that there are three areas, i.e., areas for high risk (High risk), low risk (Low risk) and no risk (No risk) of cardiotoxicity in a two-dimensional mapping on a graph, the same distribution as the known result from the relevant literature. From this result, it is found that a more accurate and simplified prediction on the probability of cardiac toxicity of an agent is possible by use of the STV in addition to the conventional FPD.

Figure 23:
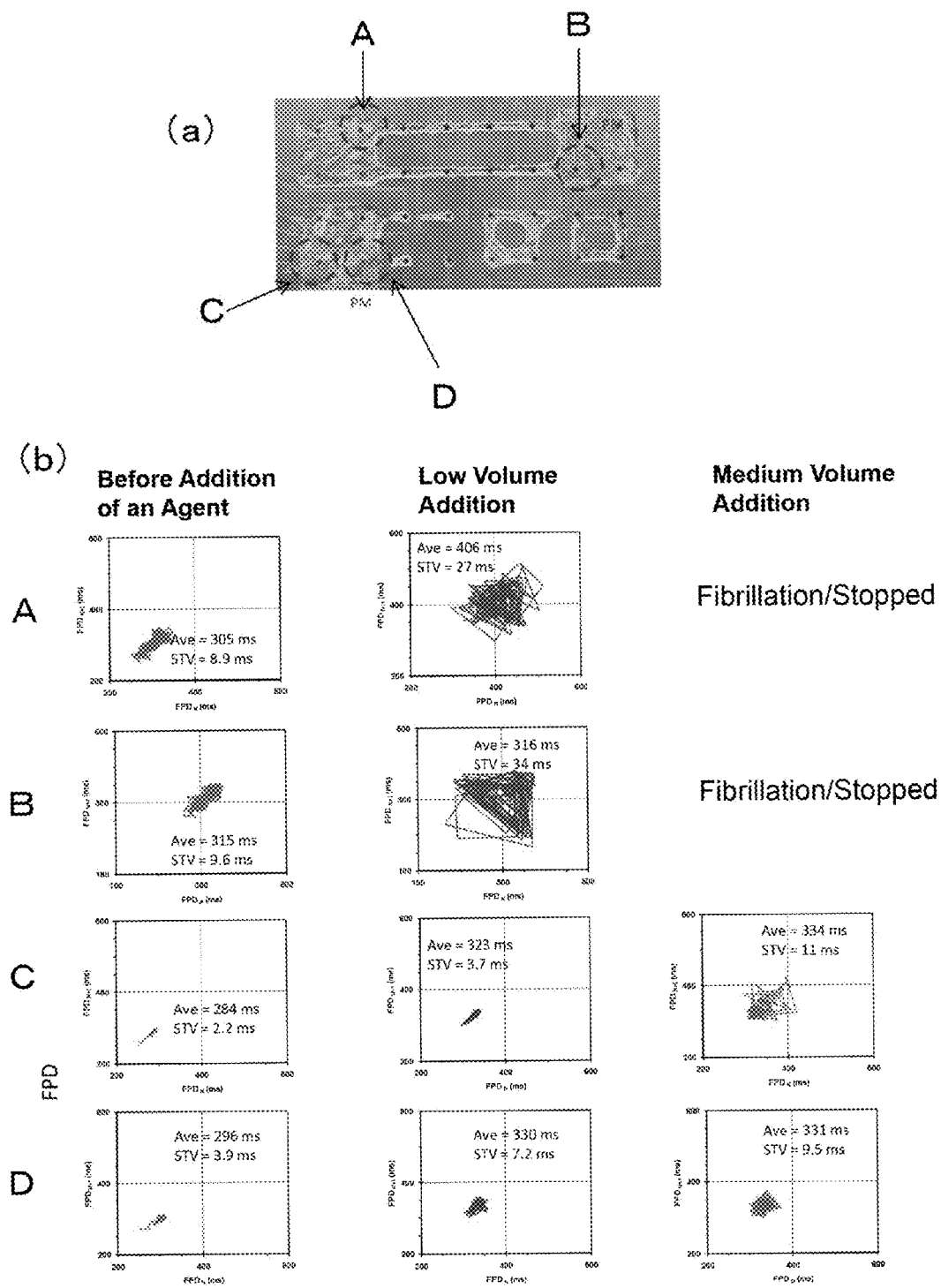
FIG. 23 shows an example of Poincare plotting of FPD against addition of an agent in terms of the difference in the shape of the cardiomyocyte network and the difference in position thereof which can be measured by the measurement system of the present invention. (a) A micrograph showing an example of an actual cellular network (a); (b) A graph showing measured changes at points A, B, C and D of (a).

FIG. 23 shows the differences in the responses of the STV with regard to the FPD in response to addition of agents. FIG. 23 (*a*) shows an example of a Poincare plotting (A, B) for the FPD for a local portion where a cardiomyocyte-network has been constituted, and (b) a Poincare plotting (C, D) of a local portion of a myocardial sheet having a two-dimensional sheet configuration. In this example, B and D are located near, and A and C are located separated from the pacemaker area PM. In (b), as for FPDs that were distributed on the diagonal of X=Y of a Poincare plotting prior to the addition of the agent, a large fluctuation is observed to occur in both the annular models (A, B) by the addition of low volume of a cardiac toxic agent, and an increase in the STV is observed, while little fluctuation occurs in the two-dimensional sheet model (C, D). In response to addition of an agent in a medium volume, the pulsation changes to a fibrillation state or a stopped state in the annular model (A, B), while an increase in the STV is observed in the area C located away from the PM in the two-dimensional sheet model (C, D). A lower rate of an increase in the STV than the area C is observed in the vicinity of the area D. As can be seen from this example, as for prediction of cardiac toxicity of an agent by measuring the STV of the FPD, it is evident that a population (network) of cells which are arranged linearly from the pacemaker area reflects more accurately the effects of the agent than a sheet-like two-dimensional cell population (network).

Figure 24:
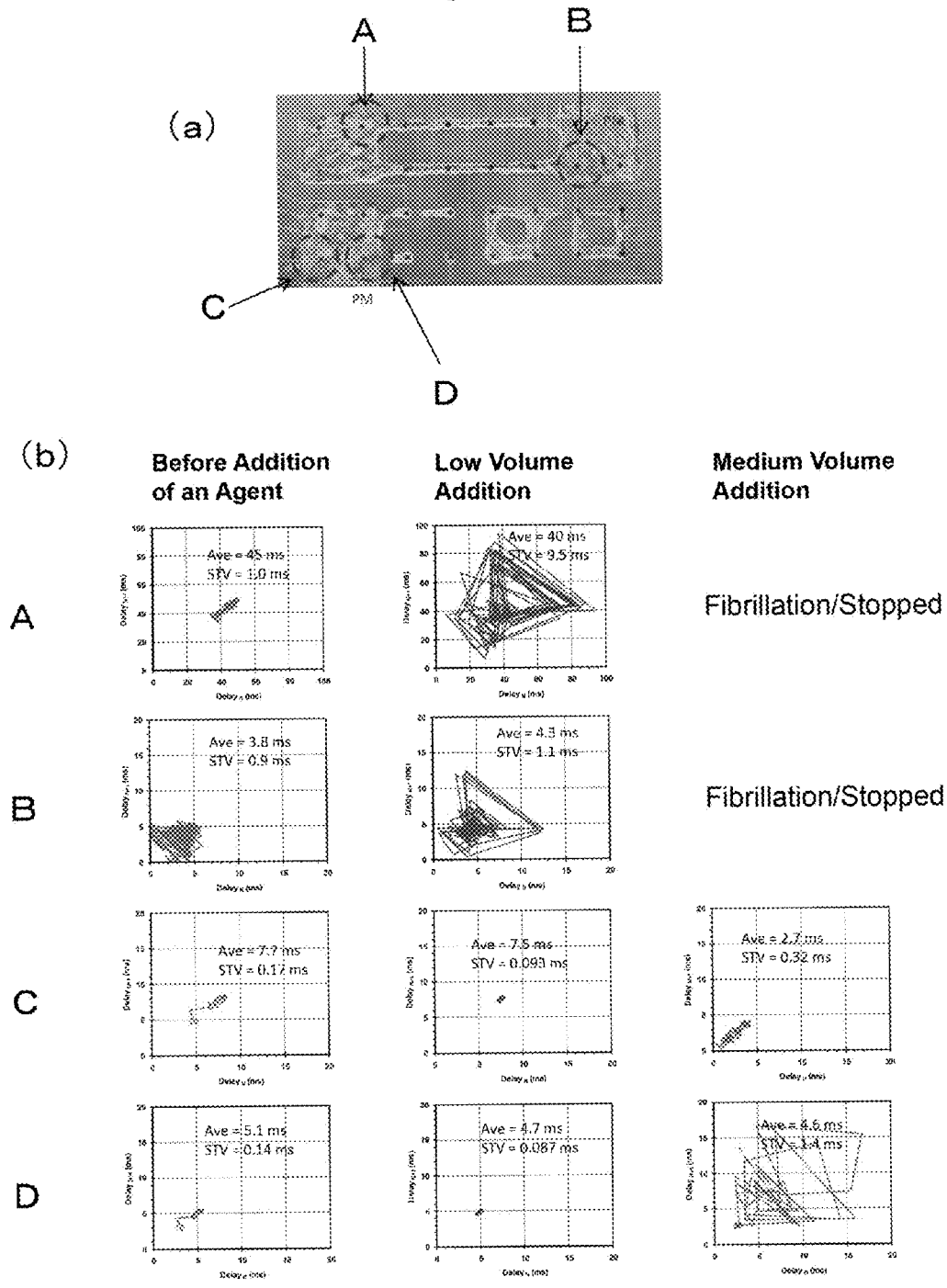
FIG. 24 shows an example of Poincare plotting of the transmission time to a local point from the pacemaker area in response to an addition of an agent in terms of the difference in the shape of the cardiomyocyte network and the difference in the position thereof which can be measured by the measurement system of the present invention. (a) A micrograph showing an example of an actual cellular network (a); (b) A graph showing measured changes at points A, B, C and D of (a).

FIG. 24 shows the difference in the response of the STV for the transmission speed (V) of pulsatile stimulation from the PM area in response to an addition of an agent. Torsade de Pointes (TdP), which is caused by cardiac toxicity, is a transmission defect in myocardial tissue, is a method for estimating the agent toxicity by checking to what extent the fluctuation of the transmission speed from the PM area is actually generated. In this case, as shown in (Equation 3) in FIG. 24 (*c*) in relation to the definition of the STV, the transmission time T from the PM area or (an apparent transmission rate V at the observation point, which is the distance from the PM divided by this transmission time) is used for the measurements instead of the FPD. The definition of LTV is also derived from changing the FPD in terms of T or V in the same way as the STV. As an example of measurement results, a Poincare plotting of transmission time T for a local point in the case of an annularly-constituted cardiomyocyte network is shown in FIG. 24 (*a*) (A, B); and a Poincare plotting for a local point in the case of a two-dimensionally spread myocardial sheet is shown in FIG. 24 (*b*) (C, D). In the same manner as FIG. 23, B and D in this example are also located in proximity to, and A and C are located separated from the pacemaker area PM. In FIG. 24(*b*), for the FPDs, which were distributed on the diagonal of X=Y of a Poincare plotting prior to the addition of an agent, a large increase in the fluctuation is observed to occur for both the annular models (A, B) as well as an increase in the STV showing a great fluctuation in transmission time by the addition of a low volume of the cardiac toxic agent, while little fluctuation is observed to occur for the 2-dimensional sheet model (C, D). In response to the addition of a medium volume of the agent, the pulsation changes to a fibrillation state or a stopped state in the annular model (A, B), while an increase in the STV is observed in the area C located away from the PM in the two-dimensional sheet model (C, D). A lower rate of an increase in the STV than the area C is observed in the vicinity of the area D. As can be seen from this example, as for the prediction of cardiac toxicity of an agent by measuring the STV of the transmission time T (or an apparent transmission time at each local point), a population (network) of cells which are arranged linearly from the pacemaker area reflects more accurately the effects of the agent than a sheet-like two-dimensional cell population (network), and at the same time, it can be seen that a generation of the fluctuation, which exhibits a spatial-dependent arrangement, can be measured more effectively.

Figure 25:
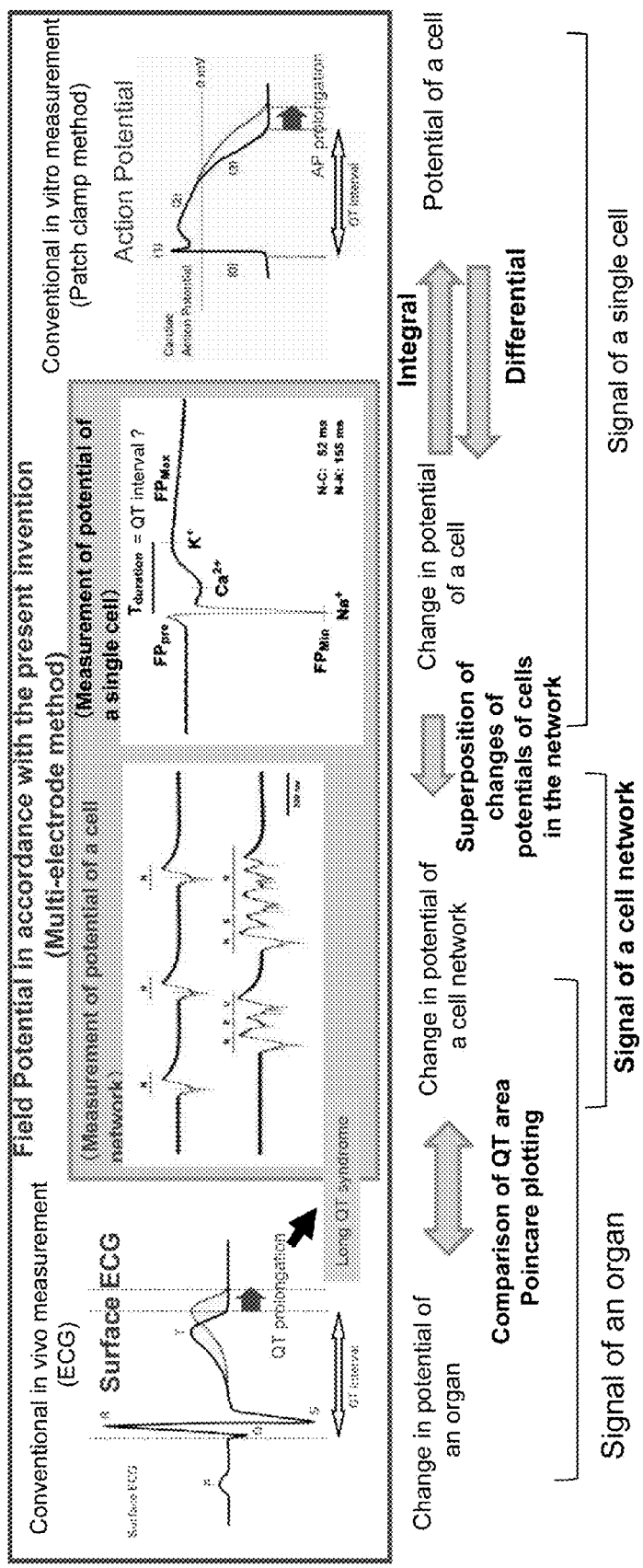
FIG. 25 is a diagram schematically showing a relationship between a conventional in vitro measurement method and a conventional in vivo measurement method, and a relationship between an FP waveform of a single cell and a composite FP waveform of a cellular network during the measurements of a network of cardiomyocytes measurable by the cell measurement system of the present invention.

FIG. 25 schematically illustrates an electrical FP waveform obtained from a cardiomyocyte in accordance with the cardiomyocyte network of the present invention in relation to a conventional in vitro measurement technique (e.g., patch clamp technique) and a conventional in vivo measurement technique (e.g., electrocardiogram). The waveform obtained by measuring the FP of the cell in accordance with the present invention indicates the magnitude of ion current per unit time into and out from the cell, which is equivalent to information on changes in the potential of the cell (which is electrically ion current), and which has the differential- and integral-relationships with the electric potential of the cell obtained from conventional in vitro measurements on a cell base as depicted in FIG. 25. Then, a composite waveform of the FP for the cellular network can be obtained by superposing the FP waveform which is measured for each cell (or a local point of the cell network) and collected from one electrode on each of the FP waveforms collected from a plurality of electrodes that are arranged in a plurality of areas of the cellular network. This data has a homology with the electrocardiogram data of the QT area corresponding to a response of a ventricular tissue portion of the electrocardiogram which is a signal waveform of a potential change obtained from the heart.

Figure 26:
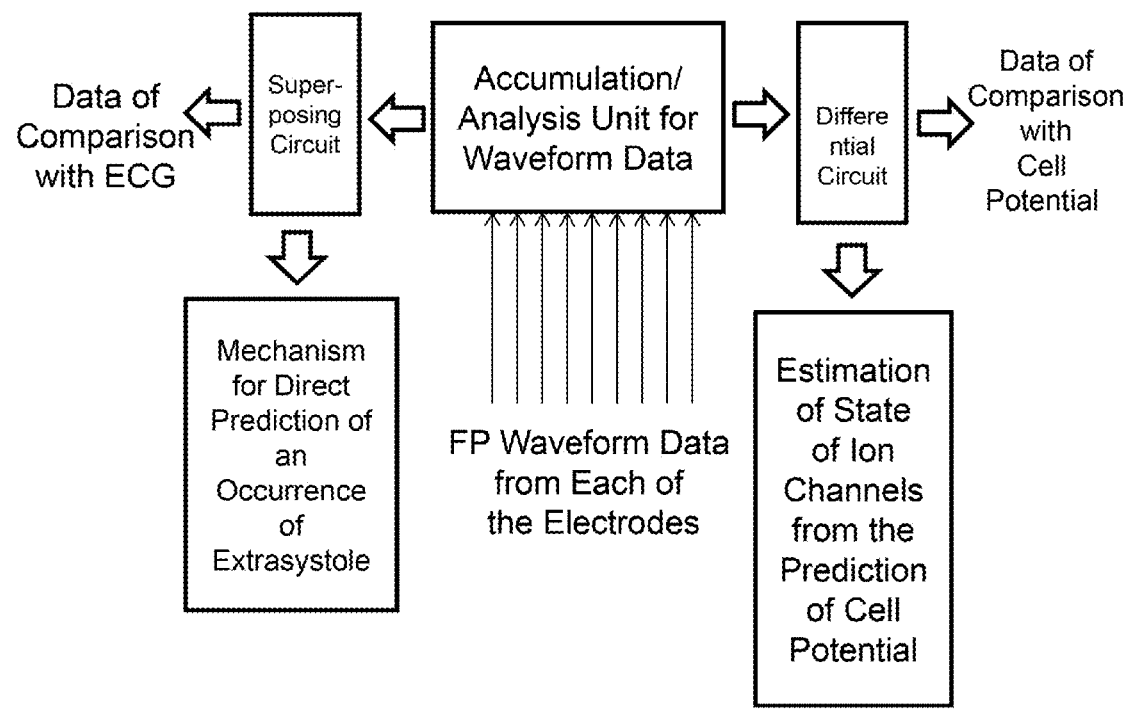
FIG. 26 is a diagram schematically showing a configuration of an apparatus having a function to estimate membrane potentials of cells from the FP waveform of the cells collected from each electrode and a function to compose a comparison waveform of an electrocardiogram from a composite FP waveform of the cellular network during the cardiomyocytes-network measurements which are measurable by the cell measurement system of the present invention.

FIG. 26 schematically shows a configuration of an apparatus system for estimating a correlation between information measured by the conventional technique as described in FIG. 25 above and the FP data obtained with the apparatus of the present invention. The apparatus system is comprised of an arithmetic circuit that has a function to integrate the FP data obtained from each one of the plurality of microelectrodes which are arranged to be able to measure the FP of one cell or a local portion of the cellular network to estimate the membrane potential by differentiating their respective FP data; or an arithmetic circuit that is capable of comparing the data of each electrode with an electrocardiogram waveform of the ventricular portion (Q-T portion) of the electrocardiogram by superposing each electrode data. In particular, in addition to analysis of the FP data of a single electrode that is made possible by using the superposing circuit, it is also possible to makes predictions similar to electrocardiogram analysis using the results obtained by, for example, composing data of an array of a plurality of microelectrodes which are arranged in series and equally spaced on a cellular network so that data reflecting the state of intercellular transmission as well as results of the FP of the cell on each electrode can be displayed; and in particular, by transferring the information of the results of the superposing circuit directly to the prediction mechanism after occurrence of extrasystole for estimating arrhythmia which is an abnormal transmission between cardiomyocytes. This is due to the fact that an abnormality in the transmission is reflected in the waveform of the FP. On the other hand, data of a membrane potential obtained from the differentiation circuit is used to assess the state of ion channels which have different activated states in a membrane potential dependent manner.

Figure 27:
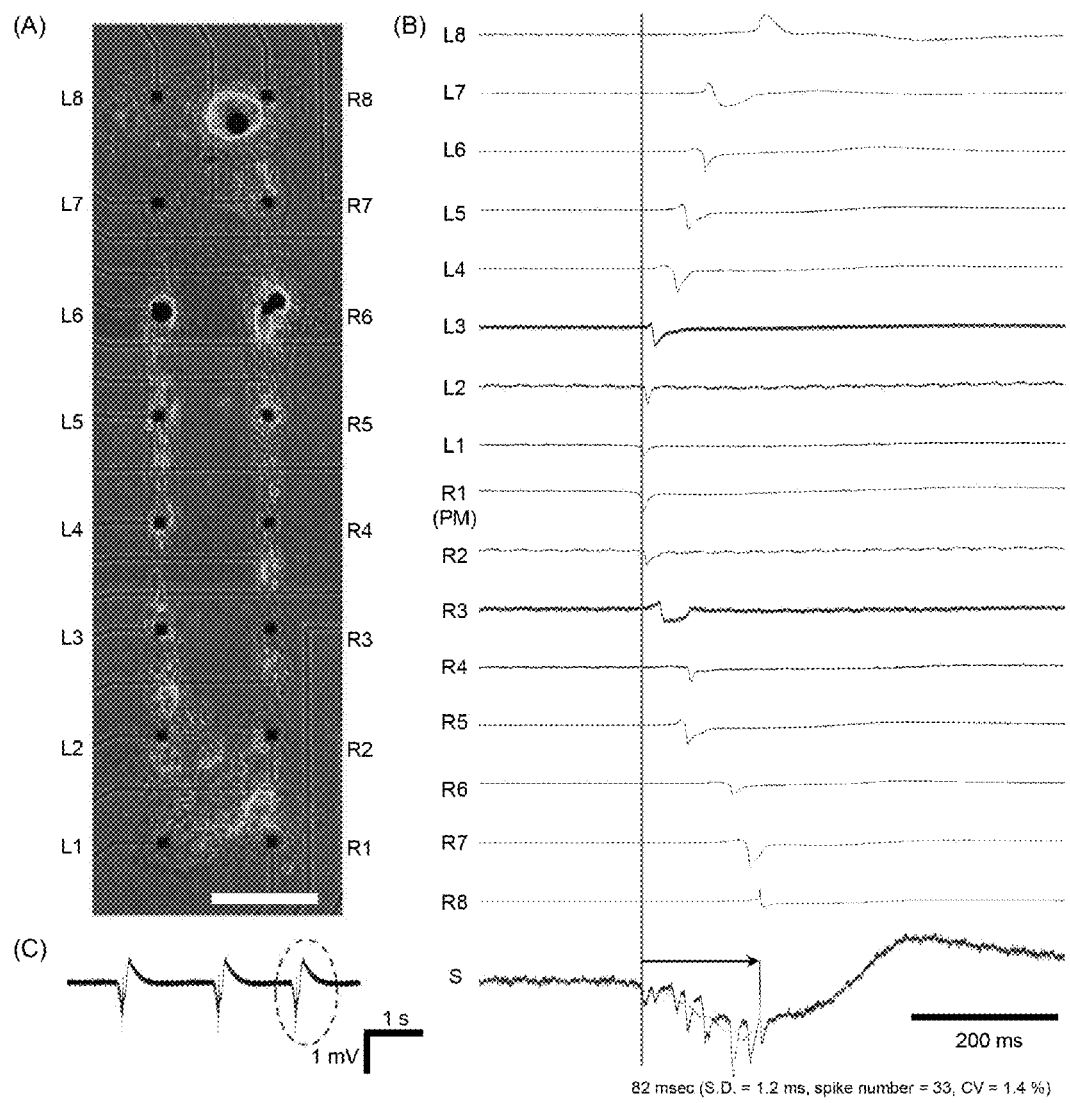
FIG. 27 shows examples of: (A) an annularly arranged cardiomyocytes network; (B) FP waveforms of cells obtained from each electrode of the network of (A); (C) a composite FP waveform composing the waveforms of (B). This example shows an example in which the pulsation signal is transmitted normally from the PM area.
Figure 28:
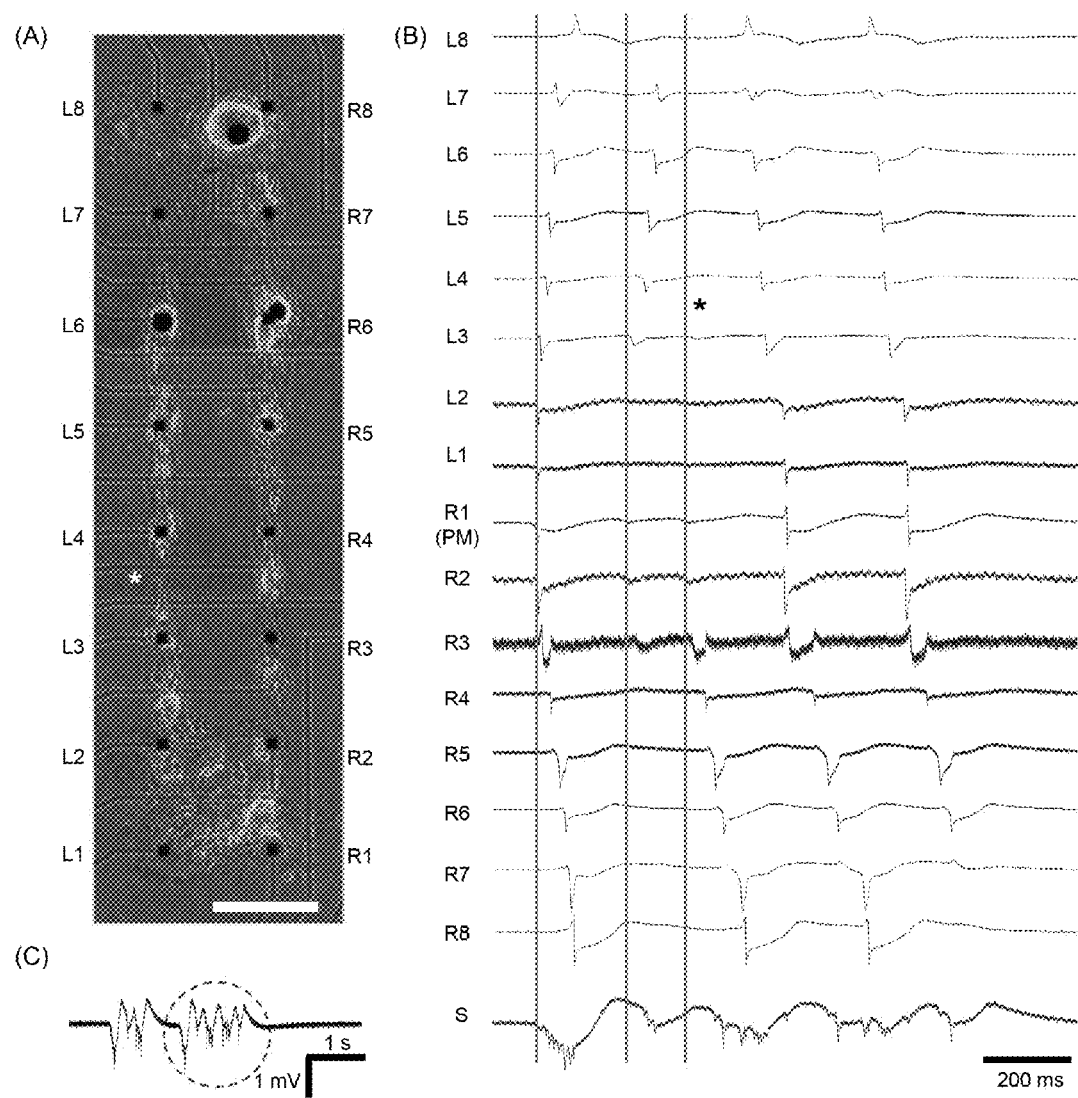
FIG. 28 shows examples of: (A) an annularly arranged cardiomyocyte network; (B) FP waveforms of cells obtained from each electrode of the network of (A); (C) a composite FP waveform composing the waveforms of (B). This example shows an example in which the pulsation signal is transmitted abnormally from the PM area.

FIG. 27 and FIG. 28 show an example in which the FP data from each electrode are actually superimposed by an arithmetic circuit as described in FIG. 26. In FIG. 27, as shown in FIG. 27(A), the cardiomyocyte network is annularly arranged; microelectrodes are arranged at regular intervals along the network. In the annular cardiomyocyte network in which the pacemaker (PM) area is located at electrode R1, it can be seen from the FP waveform of each electrode shown in FIG. 27(B) that the pulsation signal is transmitted from R2→R8 or L1→L8. The S waveform at the bottom is the superimposed waveform. FIG. 27 (C) shows the result of a long-term measured composite waveform. This is an actual composite FP waveform which includes information on the FP transmission required for estimating the waveform for the QT area in the electrocardiogram. As can be seen from this figure, when the pulsation signal is transmitted from the area PM in a normal way, the composite waveform is a smooth waveform as can be seen from FIG. 27(C). On the other hand, in an arrhythmia state where the pulsation signal from the PM area is no longer transmitted in a normal way, the S, a composite FP, becomes a very disturbed-waveform as can be seen from FIG. 28(B). Also in FIG. 28(C), which corresponds to the electrocardiogram, the composite FP waveform is a waveform with a similar shape to the waveform for arrhythmia. It should be particularly noted here that when arrhythmia is predicted based only on one electrode data of each microelectrode of FIG. 28 (B), it is difficult to predict the occurrence of a significant arrhythmia in some observed electrodes (L5, for example). However, a more accurate prediction is possible when a composite FP waveform is used as can be seen in FIG. 28(B) S or FIG. 28(C).

Figure 29:
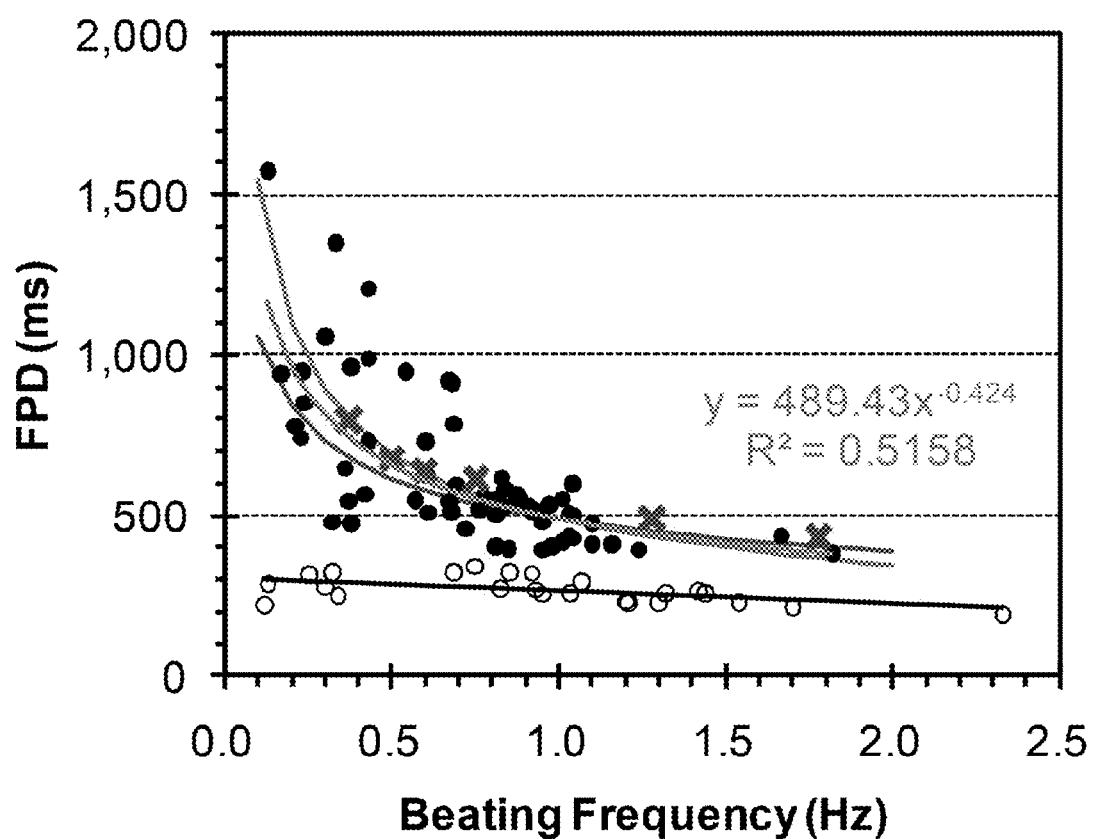
FIG. 29 is a graph showing an exemplary relationship between the beating frequency (beating frequency) of cardiomyocytes and the FPD during the cardiomyocyte-network measurements which are measurable by the cell measurement system of the present invention.

FIG. 29 is a graph showing the size of the FPD in relation to the pulsation period of cardiomyocytes. The result of the measurements of the FPD for cardiomyocytes with various autonomous pulsations by the apparatus system of the present invention is indicated in black circles. As can be seen from this result, it can be seen that the cells varied their pulsation period depending on the value of the FPD. This suggests that when the measurement is performed with cardiomyocytes with various autonomous pulsations, side effects such as stopping or destabilization of the pulsation period by an agent raise the possibility that the FPD changes are due to a cause other than natural blocking of ion channels. In addition, the red×mark denotes the value of the FPD when the pulsation period of the cell was forced to change by forced pulsation. It can be seen that the FPD becomes stable by maintaining a certain pulsation period over a certain period of time by continuous external stimulation.

Figure 30:
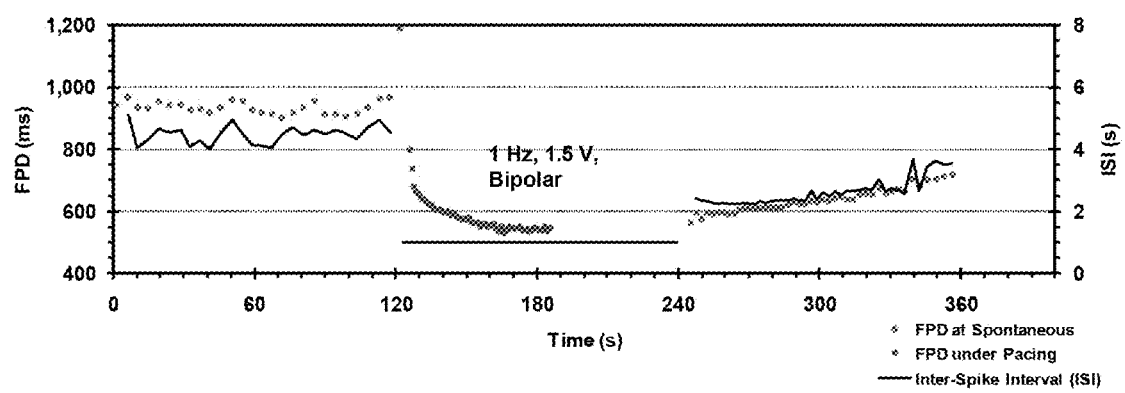
FIG. 30 is a graph showing an example of chronological change of FPD when forced pulsation is given to the cardiomyocytes during the cardiomyocyte-network measurements which are measurable by the measurement system of the present invention.

FIG. 30 shows an actual example of the change over time of the FPD of cardiomyocytes when external forced pulsatile stimulation is given using the system of the present invention to cardiomyocytes which are autonomously pulsating. It can be seen in this example that initially the autonomous pulsation interval is about 4 seconds, then the value of the FPD significantly changes immediately after the cell was given a forced pulsation stimulus of 1 Hz, then the FPD is stabilized at the position of 550 ms at approximately 30 seconds after the start of stimulation. It can also be seen that even after the forced pulsatile stimulation, the autonomous pulsation period varies, and the FPD steadily increases. As can be seen from these results, it is desirable to test the agent toxicity after 30 seconds from the start of forced pulsatile stimulation where the FPD is stable.

Figure 31:
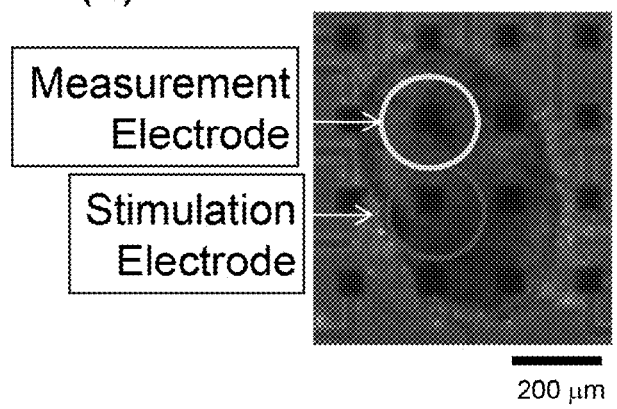
FIG. 31 is a photomicrograph showing an example of the cellular network arrangement when the FPD is measured when forced pulsation is given to cardiomyocytes during the cardiomyocyte-network measurements which are measurable by the measurement system of the present invention.
Figure 31:
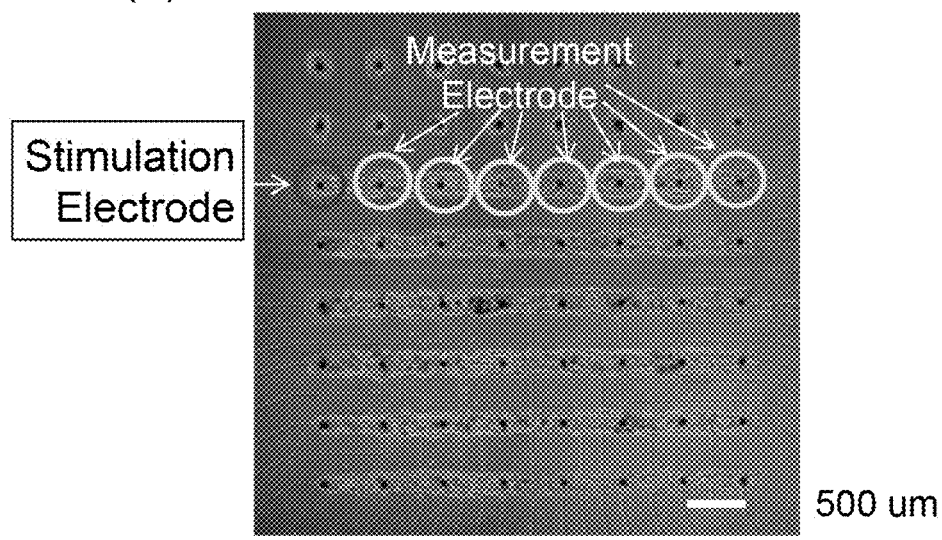

FIG. 31 shows an actual example of the arrangement of cells when measuring the FPD or transmission time T or transmission velocity V while giving external forced pulsatile stimulation using the system of the present invention. FIG. 31(a) is an example of measurement of stimulation with cell populations that are disposed to cover at least two microelectrodes. While providing forced stimulation signals at a fixed interval of 60 beats per minute from the stimulating electrode, for example, the FPD of the cells at the adjacent measurement electrode, or the transmission time T or the transmission speed V from the time of stimulation at the stimulating electrode to the cells on the measuring electrode are measured. FIG. 31 (b) shows an example in which forced pulsatile stimulation is given by a stimulation microelectrode disposed at the end point of the network of cardiomyocytes which are arranged in a straight line, the FPD, T and V of cardiomyocytes on each electrode are measured for the transmission by a microelectrode array disposed along the network of the cardiomyocytes at regular intervals, and for example, prediction of the occurrence of arrhythmia by a composite FP of the FPs of each recording electrode, the relationship between T and V of each electrode as well as the data of each of the electrodes to the stimulation signals of the stimulating electrode can be estimated. However, what is shown here is only an example of the arrangement of the cells. It is also possible to make similar measurements by providing forced pulsations in the PM area of the annular cellular network shown in FIG. 27, or alternatively, it is also possible to make measurements of the FPD on the minimum number of cells using the stimulating electrode, on which the cells are placed, as a measurement electrode.

For all examples so far, the cardiomyocyte network is described only for cardiomyocytes. However, it is intended to include embodiments where fibroblasts are added to have properties similar to biological tissues.

Figure 32:
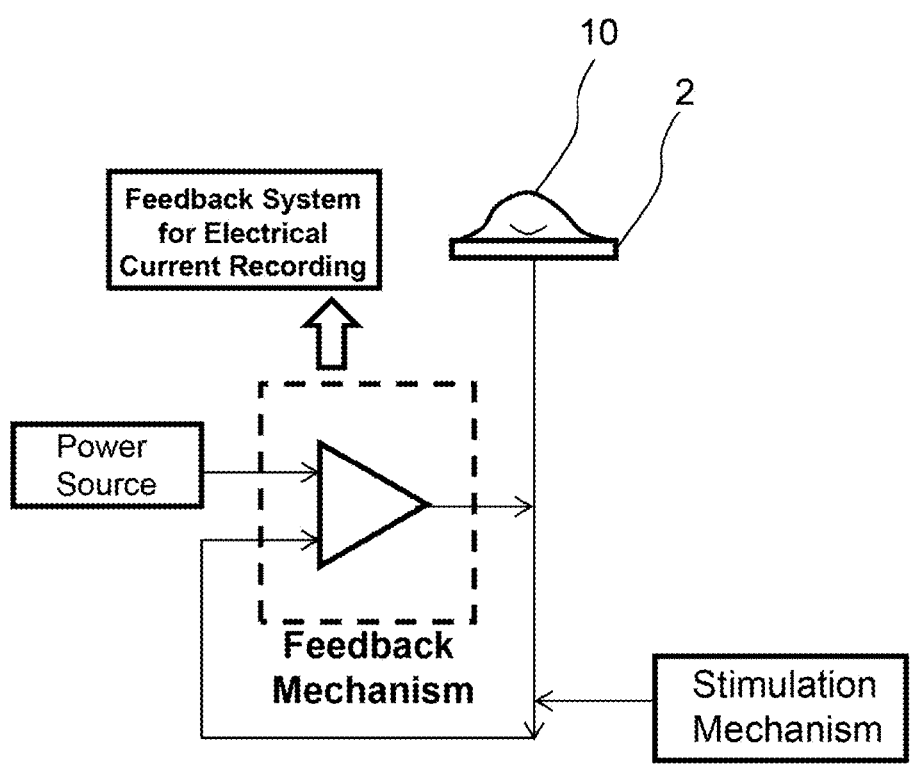
FIG. 32 is a schematic diagram showing an example of using a mechanism to maintain a constant potential at microelectrodes using a feedback control of a trace electrode potential to measure the FP of cardiomyocytes during the cardiomyocyte-network measurements which are measurable by the measurement system of the present invention.

FIG. 32 shows a potential clamp-type feedback control mechanism to maintain a constant voltage of microelectrode 2 and make measurements for the FP of cells disposed on the microelectrode 2. Here, the FP of cells is estimated by analyzing the result in real time by monitoring the current supplied from the external power supply to maintain the potential of the electrode 2 instead of measuring the amplified signal from the electrodes in the conventional configuration. It shows an example of the change over time of the FPD of the cardiomyocytes. As the potential is to be kept constant, in this context, it is normally chosen to take a value of zero, however, in the case that the state of cells is changed, for example, by changing the potential of depolarization, it is also possible to adjust to those different potentials.

Figure 33:
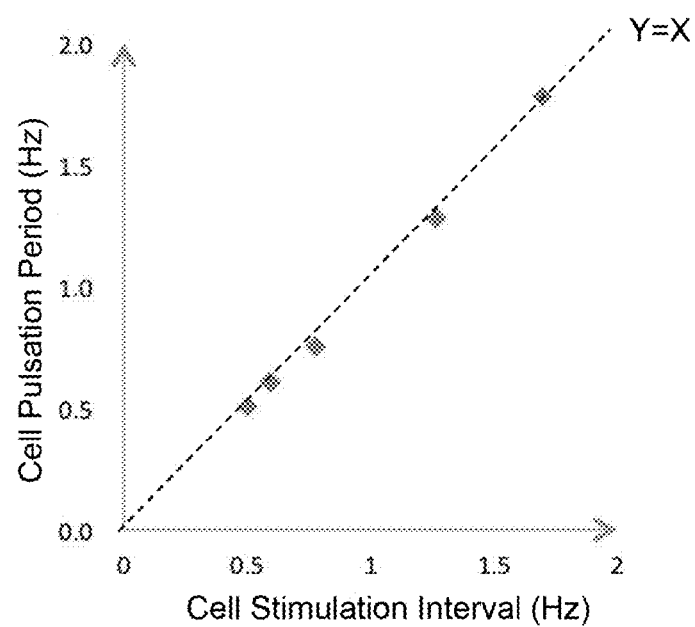
FIG. 33 is a graph showing an example of the relationship with the response of the beating frequency of the cardiomyocyte population when forced pulsation is given to a partial area of the cardiomyocyte population during the cardiomyocyte-network measurements which are measurable by the measurement system of the present invention.

FIG. 33 is a graph of an example of the results of actually measuring the change in the period of pulsation of the cell population when forced pulsatile stimulation is provided using the system of the present invention described above in a partial area of the cell population which has differentiated from human ES cells into cardiomyocytes. As can be seen from this graph, it is found that for the normal population of cardiomyocytes, when the forced stimulation of 0.6 Hz to 1.8 Hz e.g., is given as in this example, the pulsation follows linearly in response to the forced stimulation in all of this range.

Figure 34:
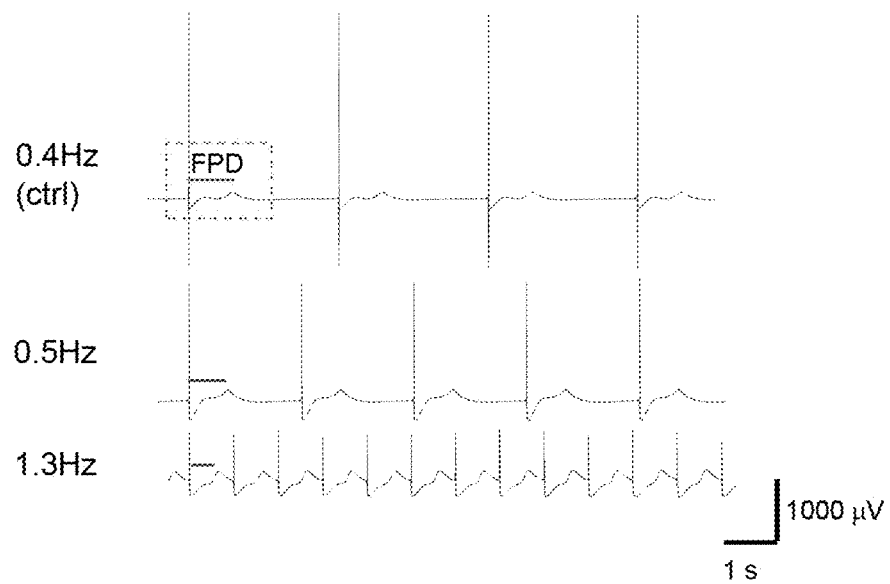
FIG. 34 is a graph showing an example of the change in the length of the FPD when forced pulsation is given to a partial area of the cardiomyocyte population during the cardiomyocyte-network measurements which are measurable by the measurement system of the present invention. A graph showing (a) an example of the relationship of the change in the length of the FPD and the change in the FP waveform caused by forced pulsatile stimulation; and (b) an example of the change in the length of the FPD in response to the change in the stimulation interval of the forced pulsatile stimulation
Figure 34:
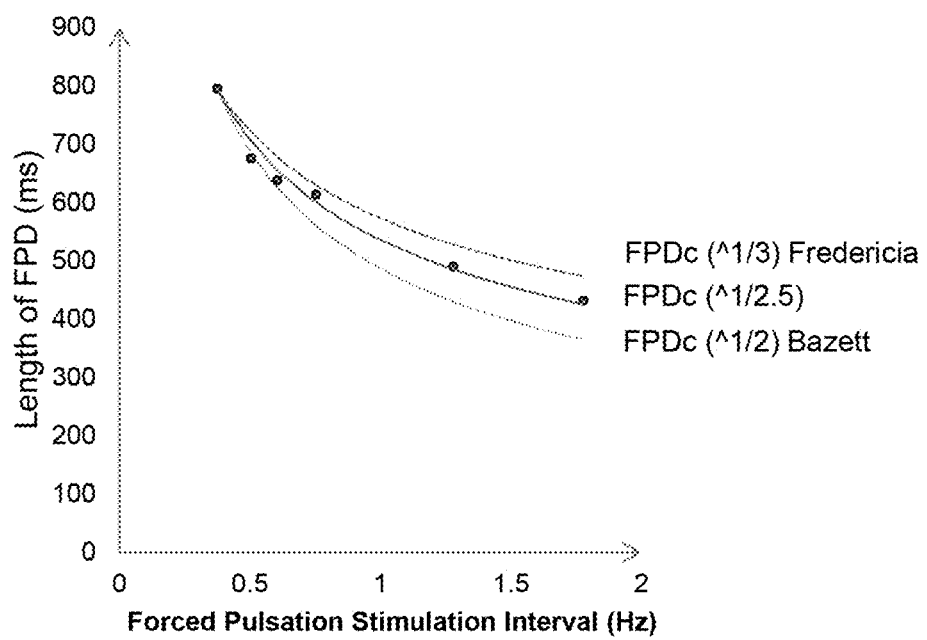

FIG. 34 (a) shows changes in the waveform of the FP and in the length of the FPD of the cardiomyocyte population under forced pulsatile stimulation where the pulsation period of the cell population is the same as the interval of the forced pulsatile stimulation when forced pulsatile stimulation is actually provided. As can be seen from the graph, the FP waveform changes and the length of the FPD shortens by shortening the interval of the forced pulsatile stimulation. As shown in FIG. 34(b), a graph of the change of the FPD indicates that this shortening depends on the cycle of the forced pulsation interval (RR). According to a known study of the relationship between a heart rate and the length of the QT interval in a human heart [Patrick Davey, How to correct the QT interval for the effects of heart rate in clinical studies. Journal of Pharmacological and Toxicological Methods 48 (2002) 3-9], a Fredericia correction with respect to this compensation relationship, i.e., in order to make a correction to the length of QT ($QT_c$) during cardiopulsation at a pulsation period of 60 beats per minute mainly depends on whether or not it conforms with the converted value of $QT_c=QT/(RR)^{1/3}$, or with the converted value of $QT_c=QT/(RR)^{1/2}$ which has been proposed by Bazett due to the fact that it is not possible to make a relative comparison because of change in the length of the QT due to the difference in the pulsation rate. As described above, the length of QT in vivo corresponds to the superposition of the length of the FPD measured across the cellular network measured by the present system. That is, it suggests that the FPD itself of each cell should enter into the range of the correction of Fredericia or Bazett. In fact, however, the result of FIG. 34(b) indicates that $QT_c=QT/(RR)^{1/2.5}$, showing that it lies between the correction of Fredericia and the correction of Bazett. In addition, FIG. 35 is a table summarizing the data shown in the graphs of FIG. 33 and FIG. 34.

These results indicate that evaluation of the quality of cardiomyocytes to be actually used for screening or in regenerative medicine can be addressed by measuring the response of the cardiomyocytes when forced pulsatile stimulation is given to the cardiomyocytes. In other words, the following procedures are noted:

1) providing forced pulsatile stimulation to a cardiomyocyte or a cardiomyocyte population; evaluating as to whether the cell or the population of the cells respond to the forced pulsatile stimulation and respond at the same interval as the forced pulsatile stimulation; verifying what frequency range of the response of the cells to the forced pulsation signal; and determining that one of the sufficient conditions for a healthy cardiomyocyte is met when it is demonstrated that the pulsation follows the stimulation; more specifically, determining that one of the sufficient conditions for a healthy cardiomyocyte is met when it is demonstrated that the pulsation follows the stimulation up to at least 1.8 Hz, for example.

2) determining that one of the sufficient conditions for a healthy cardiomyocyte is met when it is verified that the change in the FPD in response to the forced pulsatile stimulation is between $FPD/(RR)^{1/3}$ and $FPD/(RR)^{1/2}$ within a range of the frequency at which the follow-up of the pulsation of the cells in response to the forced pulsatile stimulation interval (RR) has been confirmed.

By using the above procedures, quality control of cardiomyocytes can be achieved. A healthy cardiomyocyte is a cell that is capable of making a stable pulsation. Here, the cell population that underwent differentiation induction may be used as the cell population to be evaluated, or the cardiomyocytes that underwent a differentiation induction may be dispersed for measurement and evaluation on a single cell basis, or the dispersed cardiomyocytes may be collected and used as a cell population for measurement, or alternatively, the dispersed cardiomyocytes may be mixed with fibroblasts derived from a human heart and used as a new cellular population for the measurement and the evaluation. These cardiomyocytes can be used for the cardiotoxicity test.

Figure 36:
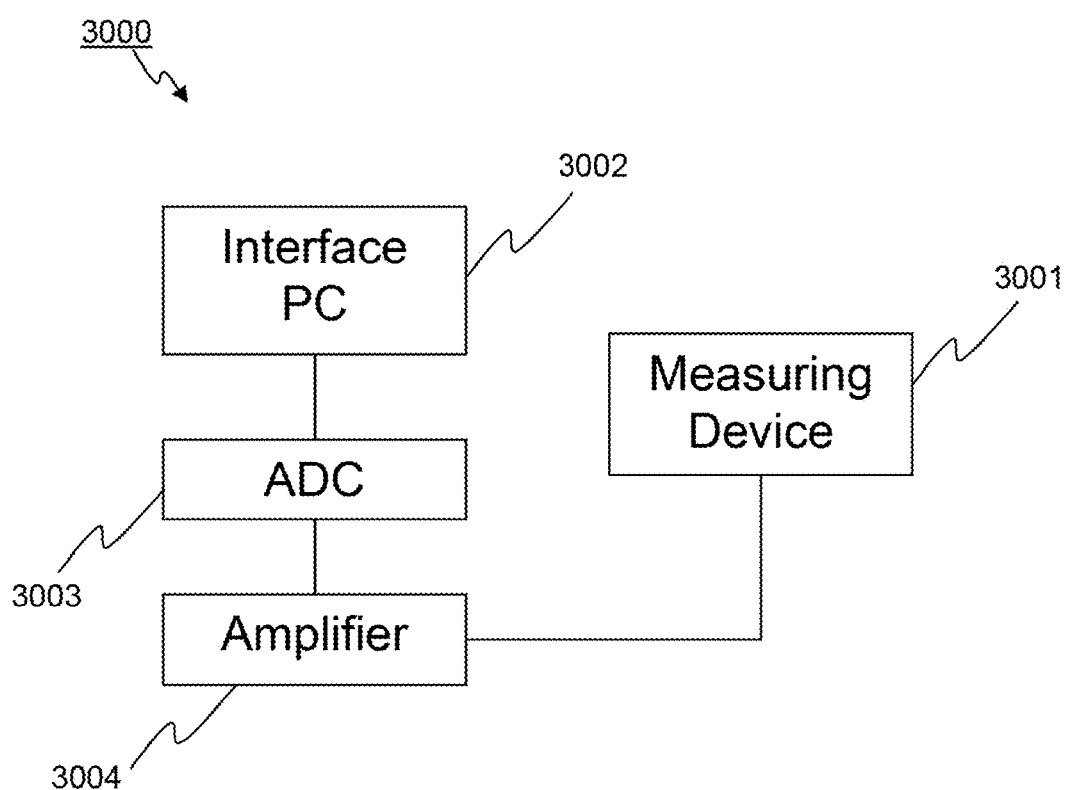
FIG. 36 is a block diagram showing an example of the overall configuration of the cardiotoxicity testing apparatus of the present invention.

FIG. 36 is a block diagram showing an exemplary overall configuration of a cardiotoxicity testing apparatus (or a cardiotoxicity testing apparatus system) according to an embodiment of the present invention. The cardiotoxicity testing apparatus 3000 of the present invention is basically composed of a measuring unit 3001 and a control/analysis unit 3002. An amplifier 3004 for amplifying the electrical signals from the measurement unit 3001, and an analog-to-digital converter (ADC) 3003 that converts analog signals from the amplifier 3004 to digital signals intervention are arranged between the measurement unit 3001 and the control/analysis unit 3002 (for example: a personal computer). The personal computer 3002 for an interface receives a signal from the ADC and makes recording, analysis and display or the like. The measuring unit 3001 essentially comprises a culture vessel having a multi-electrode array comprising a plurality of microelectrodes, an x-y stage for disposition of the unit 3001, an optical system comprising an optical microscope, a laser light source, an optical camera and the like. The culture vessel having a multi-electrode array comprising a plurality of microelectrodes can also be manufactured by microfabrication technology, but those commercially available (for example: MED-P515A, Alfa Med Scientific, Japan) may also be used.

Figure 37:
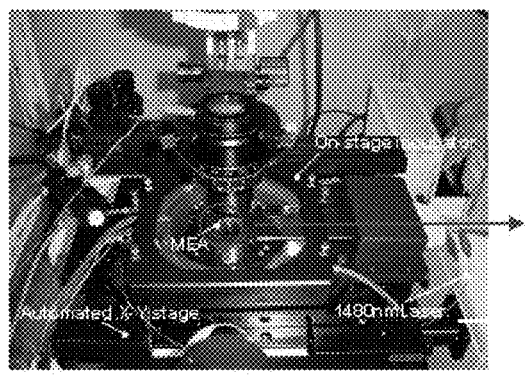
FIG. 37 is an enlarged view of the measurement unit of the cardiotoxicity testing apparatus according to one embodiment of the present invention.
Figure 37:
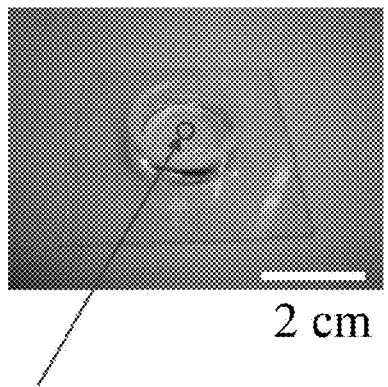
Figure 37:
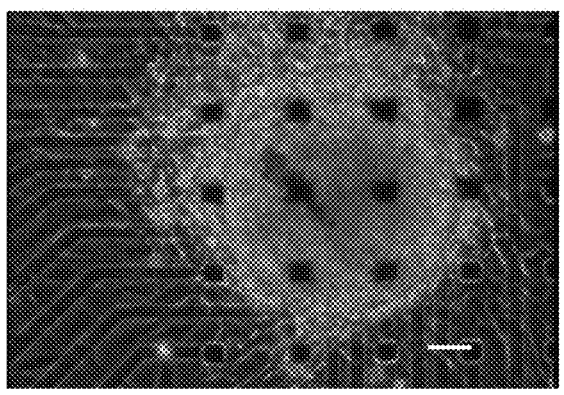

FIG. 37A is an enlarged view of the measurement unit 3001 which is the core of the cardiotoxicity testing apparatus system 3000 of the present invention. FIG. 37B is an enlarged view of a multi-electrode tip (or a culture vessel) having a multi-electrode array used in the system of the present invention. FIG. 37C is a diagram that has further enlarged the electrode portion. As shown in the figure, a plurality of microelectrodes are arranged in an array, and lead wires (or leads) are connected respectively to each of the microelectrode, and a cardiomyocyte cluster derived from a human ES cell has been placed thereon.

Figure 38:
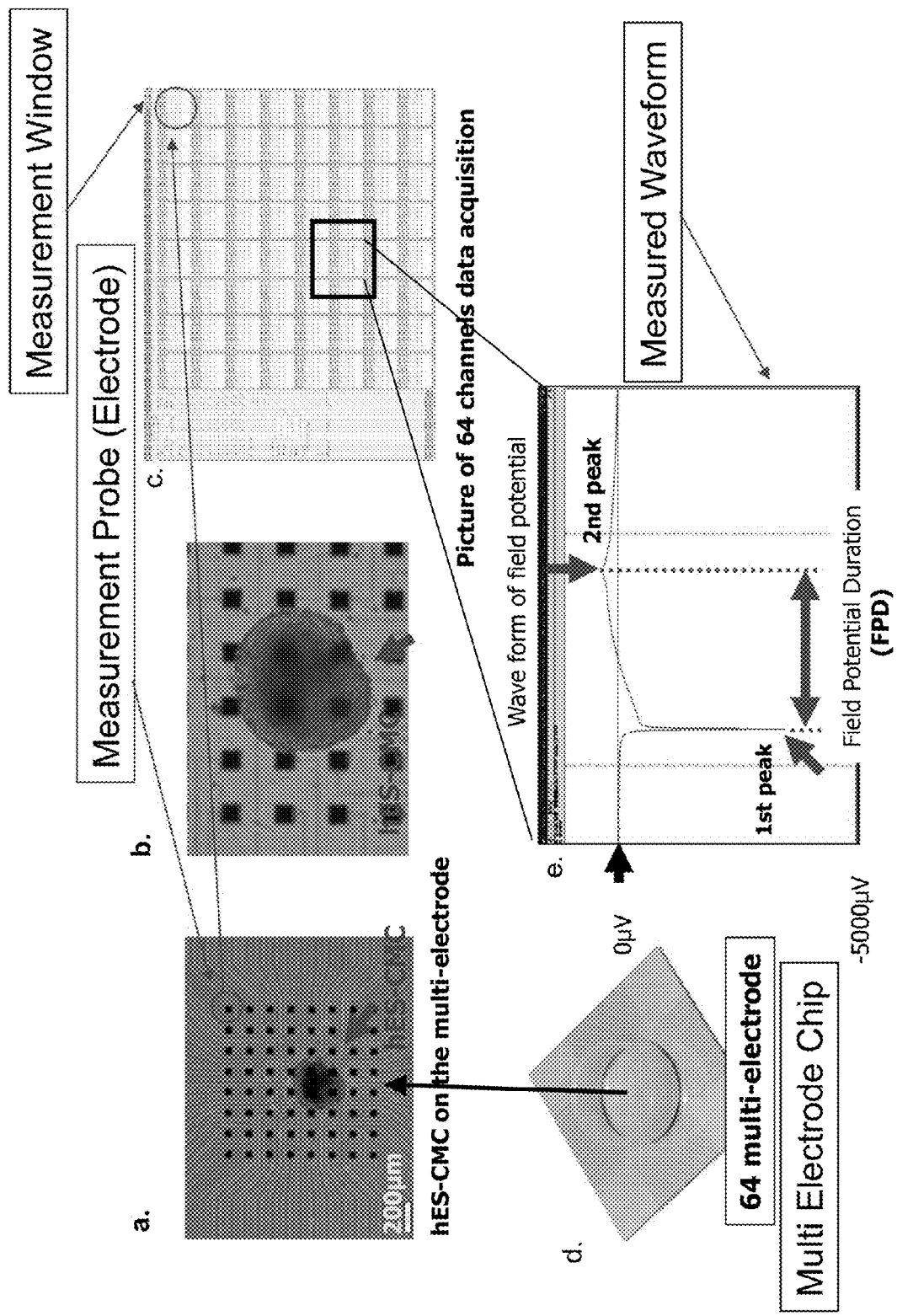
FIG. 38 is a diagram showing correspondence between the electrode of the chip and the measurement window (a-c), and a display example of the data used for the analysis (e), when evaluating the toxicity of the agent on cardiomyocytes (b) using the multi-electrode array chip (a, b, d).

FIG. 38 is a diagram showing a correspondence between the electrodes of the chip and the measurement window (FIG. 38a-c) when evaluating the toxicity of the agent against cardiomyocytes (FIG. 38b) using a multi-electrode array chip (FIG. 38a, b, d) and a display example of the data used for analysis (FIG. 38e).

One example, in which an inspection of cardiotoxicity of an agent is performed using a cardiotoxicity testing apparatus of the present invention, will be described below.

Materials and Methods

1. Cell Culture

The human ES cell-derived myocardial clusters were purchased from Cellartis. They were received in raw and recovered using a glass capillary (Vitrolife), cultured in a medium plus 20% inactivated FBS, 1% non-essential amino acids, 1% penicillin-streptomycin, and 0.2% β-mercaptoethanol in DMEM (all purchased from Invitrogen).

2. Preparation of a Multi-Electrode Tip (Day 0-3)

Collected clusters were then placed in a multi-electrode tip (Alfa Med Scientific). The day on which they were placed was set to Day 0. Clusters for which a 1st peak of an extracellular potential (FP) of 200 mV or more was acquired on Day 3 was used for data acquisition. A multi-electrode membrane potential measurement system (Nikkyo Technos Corp.) was used to acquire data.

3. Agent Application (after Day 4)

Pre-agent application data (called 'Before') was acquired for 10 minutes before agent application. The agent was dissolved in deionized distilled water (DDW) or DMSO, and diluted in PBS before its application. The final concentration for application was 0.1 µM and 1 µM for E-4031, 0.1 mM and 1 mM for DL-sotalol, and 0.1 mM and 1 mM for Diltiazem. Extracellular potential duration (FPD) and STV (short term variability) of the FPD was calculated from the acquired data.

4. Data Analysis

A steep downward peak of the FP corresponds to the inflow of Na$^+$. A gradual upward peak corresponds to the outflow of K$^+$. The FPD was defined as the time between the Na$^+$ and K$^+$ peaks. In addition, the STV of the FPD was evaluated as the variation between beats of FPD. STV was calculated by the following equation.

$$STV = \sum \frac{|FPD_n - FPD_{n+1}|}{N \times \sqrt{2}}$$

$N$ = Total number of $FPD$

The increase in the variation between the FPDs can be evaluated as an increase in the value of STV. To reduce the influence to the FPD due to variations in the beat rates, correction of FPD and the STV of the FPD were made using the formula of Fredericia correction below to obtain cFPD and the cSTV.

$$FPDc = \frac{FPD}{\sqrt[3]{RR}}$$

(RR is the time between the Na$^+$ peak just before the FP)

5. Procedure to Make a 2-Dimensional Plot

A QT prolongation or a prolongation of APD, and their STVs have been used individually in order to assess the risk of cardiac toxicity of an agent. In order to evaluate the prolongation of FPD and the increase of STV integrally, the present inventors have developed a "two-dimensional plot". X-axis represents the frequency of clusters (the FPD score) for which the FPD has extended by 10% of more than a previous value. Y-axis represents the frequency of clusters (STV score) for which the STV increased by 100% or more than a previous value. Of 2 concentrations that were applied to respective clusters, if the above-mentioned increase was observed in any of the concentrations, it was evaluated as "prolonged (FPD)" and "increased (STV)". In this plot, the agent is plotted in the area that is dependent on the strength of the cardiac toxicity of the agent.

6. Results

Two-Dimensional Plot

Figure 39:
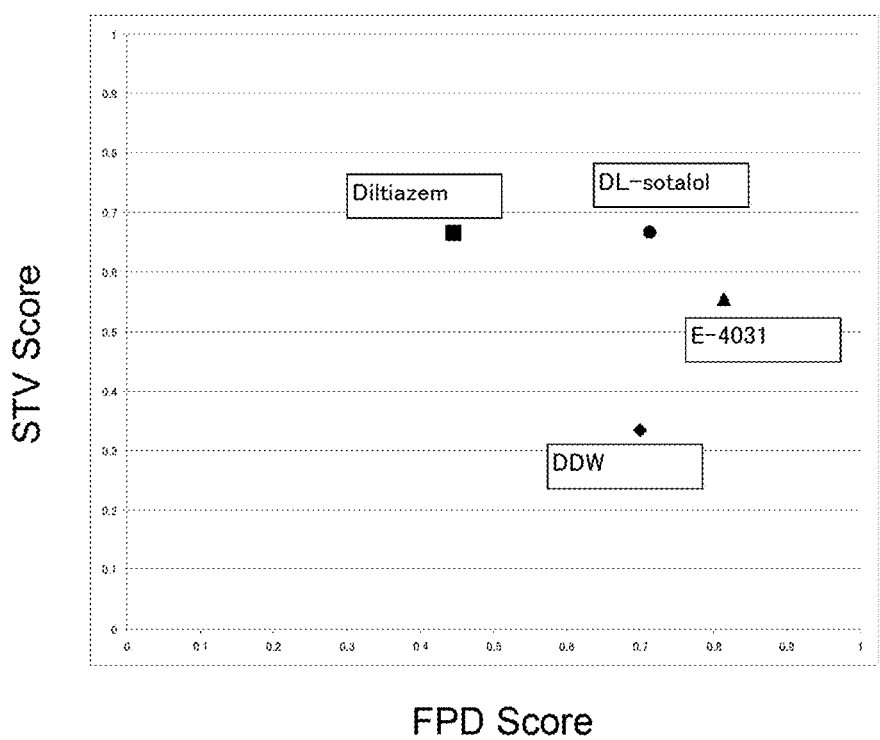
FIG. 39 shows a two-dimensional plot produced by a cardiac toxicity testing method according to an embodiment of the present invention for Diltiazem, DL-sotalol, E-4031 and DDW.

FIG. 39 is a two-dimensional plot of the agents that were evaluated. E-4031 and DL-sotalol were plotted in the upper right corner of the figure. Diltiazem was plotted in the upper left corner, and DDW was plotted in the lower right corner. E-4031 and DL-sotalol are an IKr inhibitor, and it is known that they increase the APD and STV both in vivo and in vitro. E-4031 is an agent for which a development was interrupted due to the high risk of cardiac toxicity, and thus is an agent with high cardiotoxicity. DL-sotalol is an anti-arrhythmic agent, but the risk of lethal arrhythmias cannot be ignored, and thus is considered have high cardiac toxicity. Diltiazem is a Ca$^{2+}$ channel inhibitor, and it is known that APD thereof decreases in vivo, and thus the risk of cardiac toxicity is considered to be low. DDW was considered to have no cardiac toxicity. Thus, the upper right area in the figure is judged as the area of "high cardiac toxicity" and the upper left and lower right areas are judged as the area of "low cardiac toxicity" in the obtained plot. The level of cardiac toxicity can be evaluated depending on in which area an unknown agent is plotted in the two-dimensional plot when the agent was evaluated by the present evaluation method.

Figure 40A:
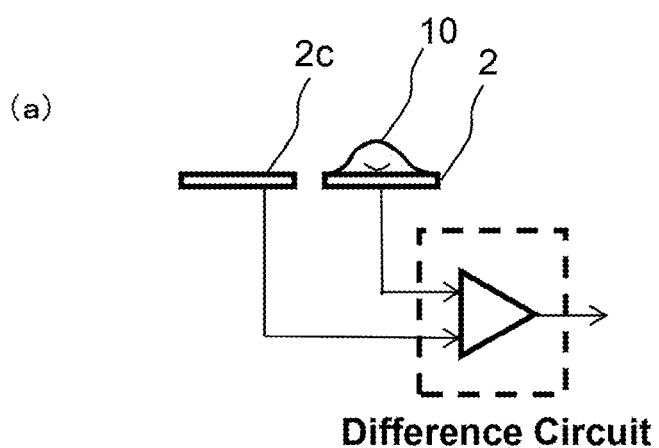
FIG. 40a schematically shows a difference circuit between a reference electrode and microelectrodes for noise removal during a measurement of an electrode potential in accordance with the present invention. (a) A schematic diagram of an example of a circuit illustrating the principles.
Figure 40B:
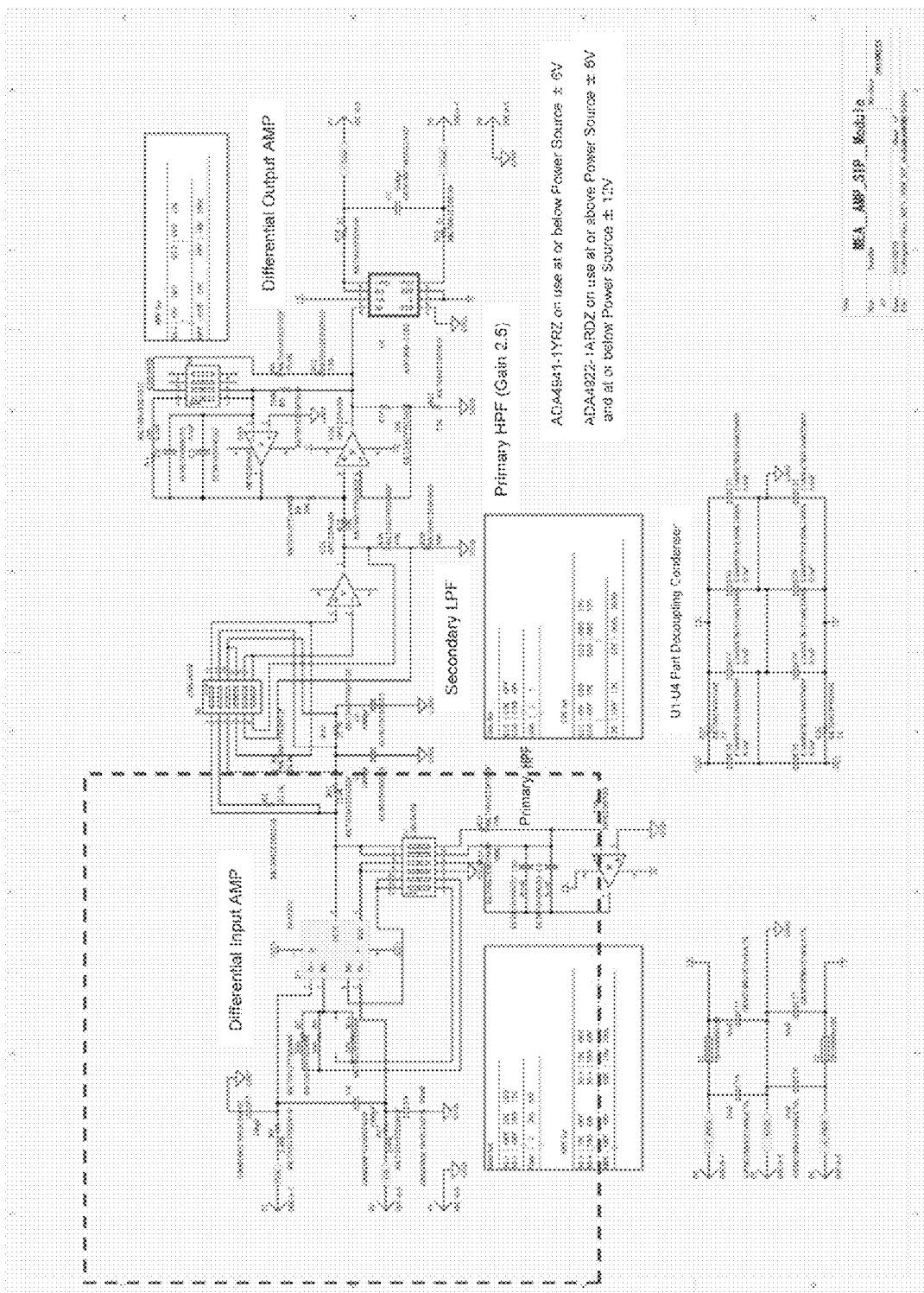
FIG. 40b schematically shows a difference circuit between a reference electrode and microelectrodes for noise removal during a measurement of an electrode potential in accordance with the present invention. (b) A circuit diagram of an example of an amplifier circuit incorporating the difference circuit.
Figure 40C:
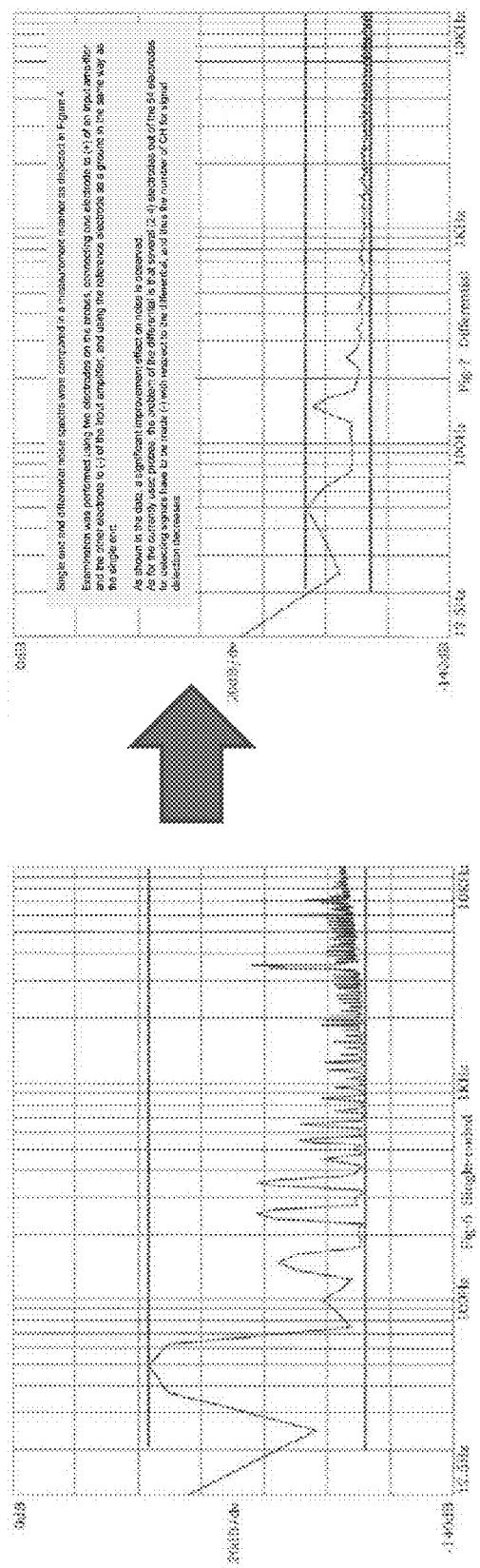
FIG. 40c schematically shows a difference circuit between a reference electrode and microelectrodes for noise removal during a measurement of an electrode potential in accordance with the present invention. (c) A diagram showing an example in which noise is reduced by the circuit.

FIG. 40(a) schematically shows a circuit for outputting a value of the difference in electric potential between a microelectrode 2 on which a cell 10 is disposed and a comparison electrode 2c, which is in the vicinity of the microelectrode 2, and on which no cell is disposed, for use in electrically reducing noise in cell signals. In fact, as shown in FIG. 40(b), by incorporating this circuit in the first stage of the amplifier circuit, it is found that the noise reduction does not depend on a specific frequency, as shown in FIG. 40(c). The position of the reference electrode 2c is preferably in the vicinity of the microelectrode. For example, it is fully functional if it is located at a distance of 50 µm, and it can function to reduce noise if it is within a distance of 1 mm.

Figure 41:
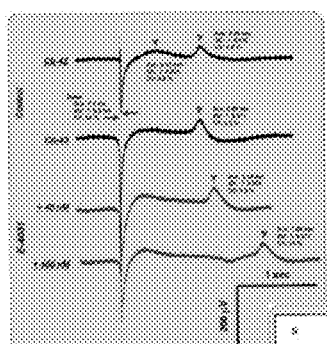
FIG. 41 is a diagram schematically showing an example of a comprehensive evaluation method for cardiotoxicity evaluation in accordance with the present invention. (a) The degree of an prolongation of the FPD from the FPD data of the cells is plotted in the X-axis, and the magnitude of temporal fluctuations of the FPD is plotted in the Y axis. (b) An example of a plot for the average data from the above results, plotted in the X-Y diagram.
Figure 41:
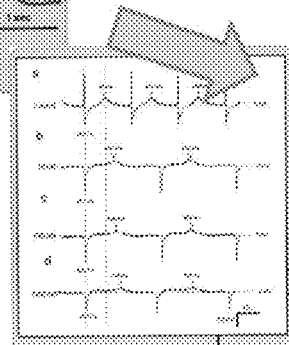
Figure 41:
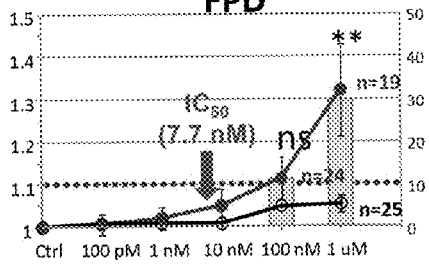
Figure 41:
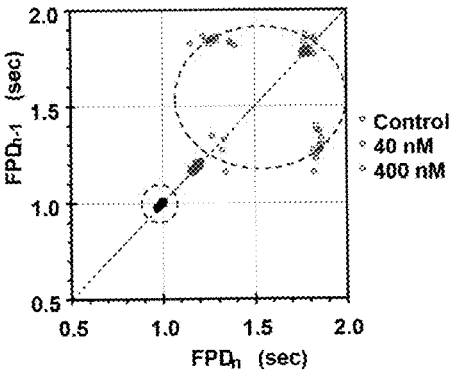
Figure 41:
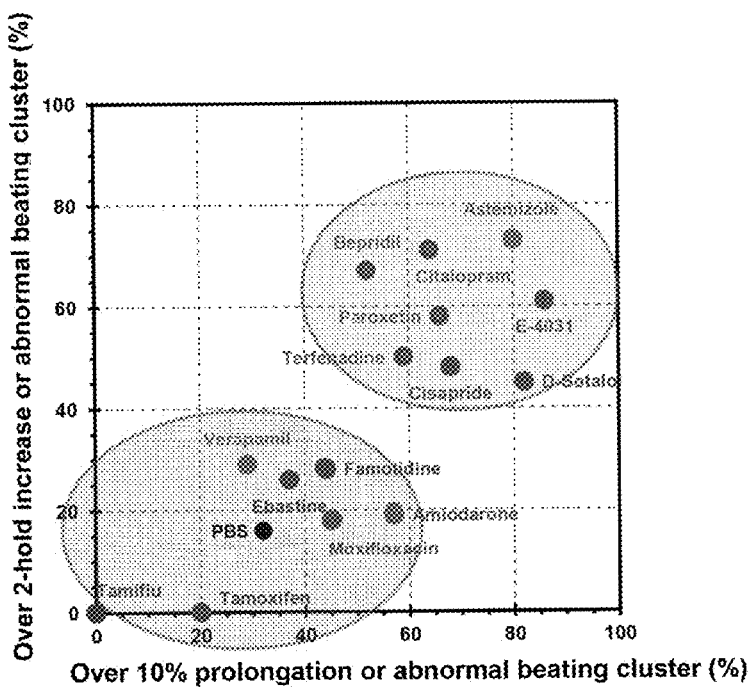

FIG. 41 is a diagram schematically showing an example of a comprehensive cardiotoxicity evaluation method of the present invention. Regarding the values for the FPD obtained from the results of measurements of membrane potential of cardiomyocytes after addition of an agent of a particular concentration, the results are plotted taking a level of the FPD prolongation as a value on the X axis and taking STV, which is derived from Poincare plotting of the magnitude of the fluctuations with time of the FPD described above, as a value on the Y axis. FIG. 41 (b) is one example of the results plotted in an X-Y diagram for a variety of agents. As can be seen from the figure, an agent in the area where the increase in the prolongation of the FPD and the fluctuation (STV) is decrease can be determined as having a QT prolongation but no cardiac toxicity, while cardiac toxicity such as TdP can be predicted when prolongation of the FPD and the fluctuation of (STV) occur simultaneously (upper right in the X-Y diagram).

Figure 42:
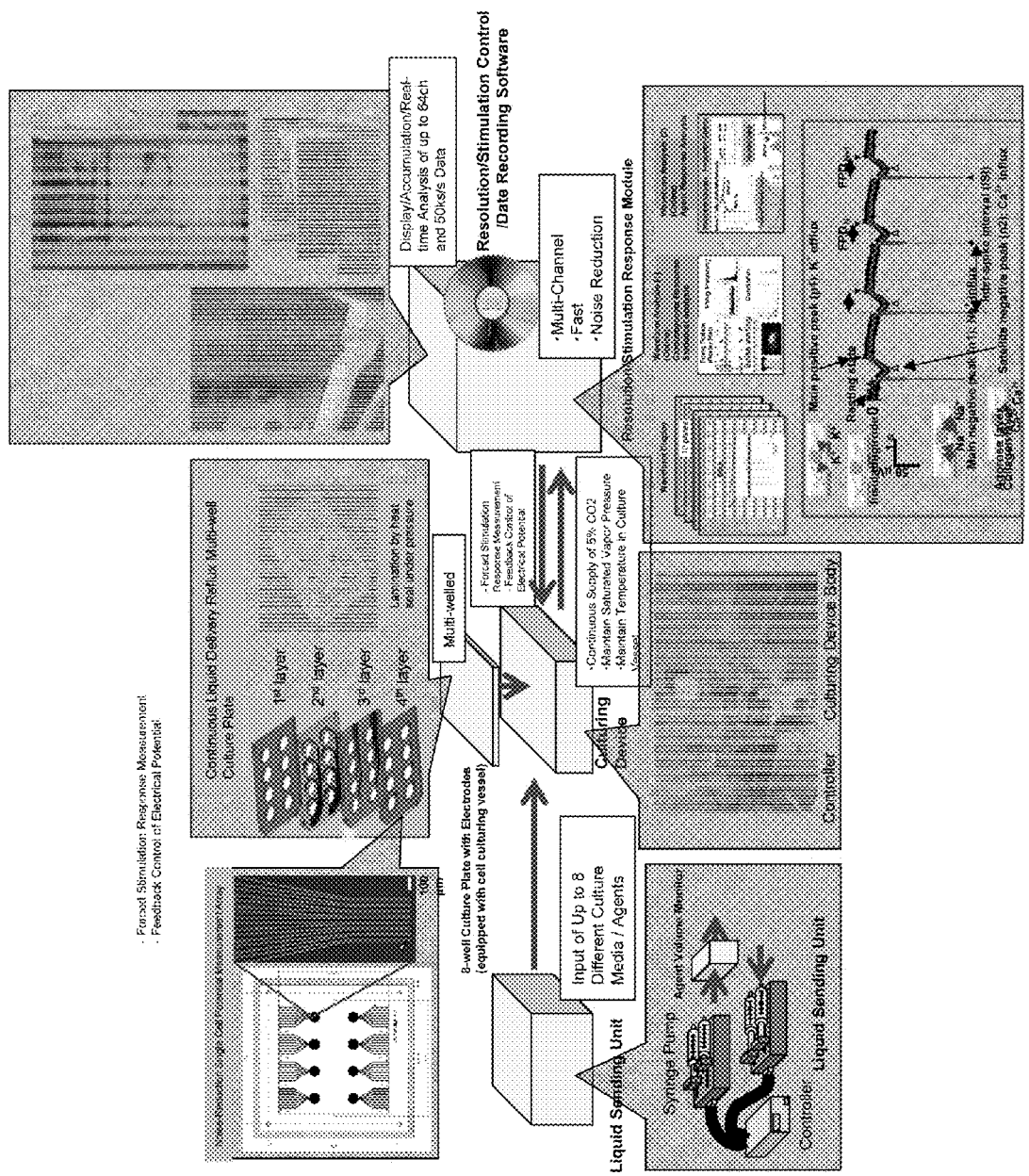
FIG. 42 is a schematic diagram showing an example of the configuration of a system for measuring the cardiac toxicity of the present invention.

FIG. 42 is a schematic diagram showing an example of the configuration of a system for measuring the actual cardiac toxicity. The system of this embodiment includes a liquid sending unit, a cell culture measurement unit, and a cell analysis/stimulation unit.

The liquid sending unit can send liquid by a syringe pump system or a peristaltic pump system or a HPLC pump system by which the culture solution is continuously fed to each of the cell culture chambers in which cells are cultured in the measurement unit. In addition, a resistive heating wire for temperature control is wound around the outer circumference of the pipe of for sending liquid, and a solution is always introduced at a constant temperature by monitoring the temperature of the liquid in the tube continuously with a detecting mechanism of heat such as a micro-thermocouple type K or a thermistor, and adjusting the temperature of the liquid to be introduced in terms of the degree of resistance heating for controlling solution temperature. In addition, the liquid sending unit includes a piping in which mechanisms such as junction pipes and switching pipes are arranged for addition of agents to be tested, and through which desired concentrations of agents can be introduced into each of the cell culture chambers. Further, the quantitative determination of the concentration of the agent solution desirably includes addition of a mechanism in which a portion of an inlet pipe of the liquid is optically transparent, and by which quantitative evaluation can be made by spectrophotometric measuring in the range of 280 nm-800 nm wavelengths. Likewise, it is also desirable that a mechanism for waste liquid is added in which a part of the waste tube is optically transparent, and by which quantitative evaluation is possible by measurement of spectroscopy absorption in the range of 280 nm to 800 nm wavelengths. The controlled temperature of the agent solution preferably approximates a normal temperature of a human body, and from this point of view, it is desirable to be able to control the temperature in the range of 30 degrees to 45 degrees centigrade.

Figure 43:
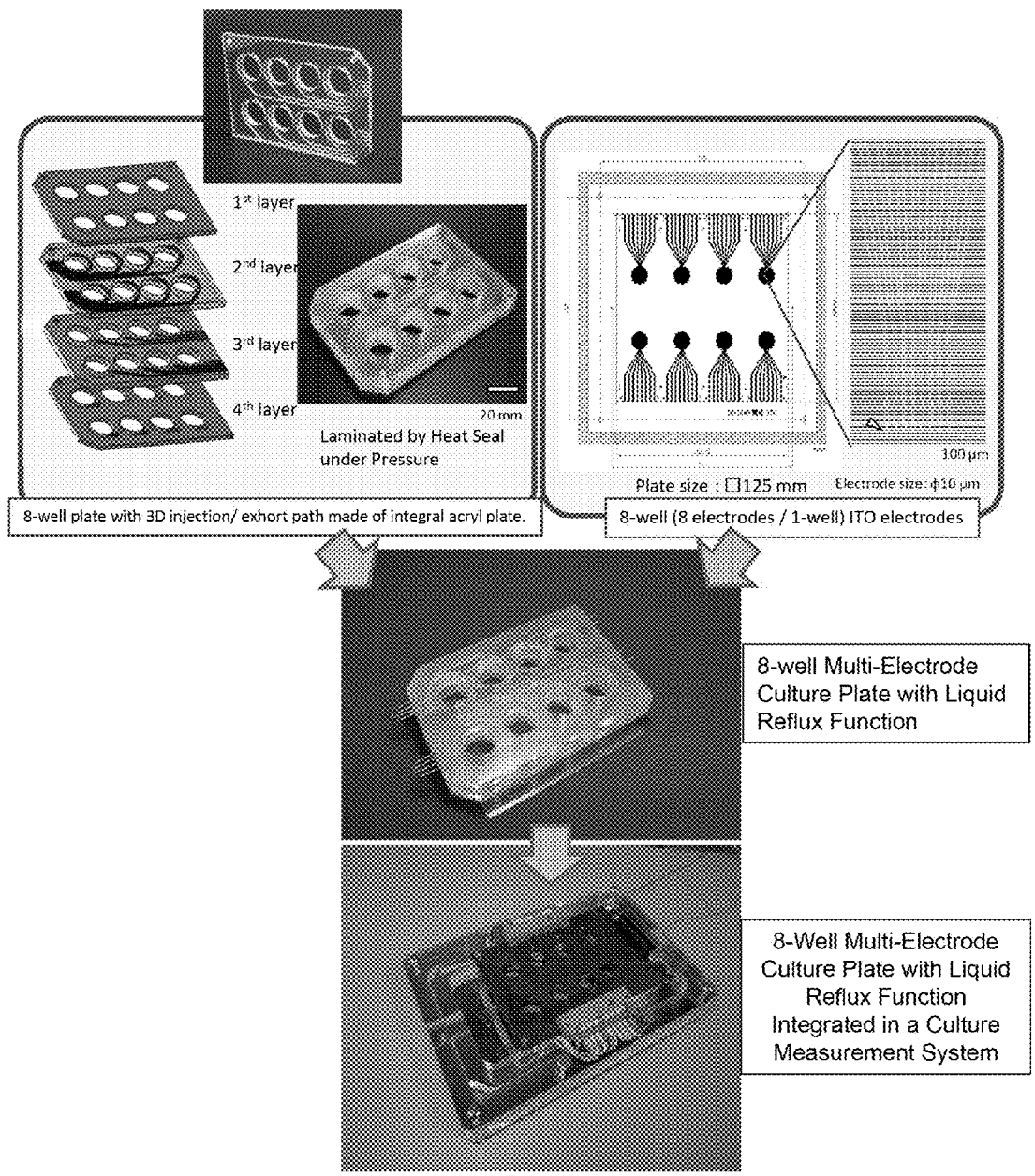
FIG. 43 is a schematic diagram and a photography showing an example of the configuration of the measurement chamber of the cell culture system to measure the cardiac toxicity of the present invention.
Figure 44:
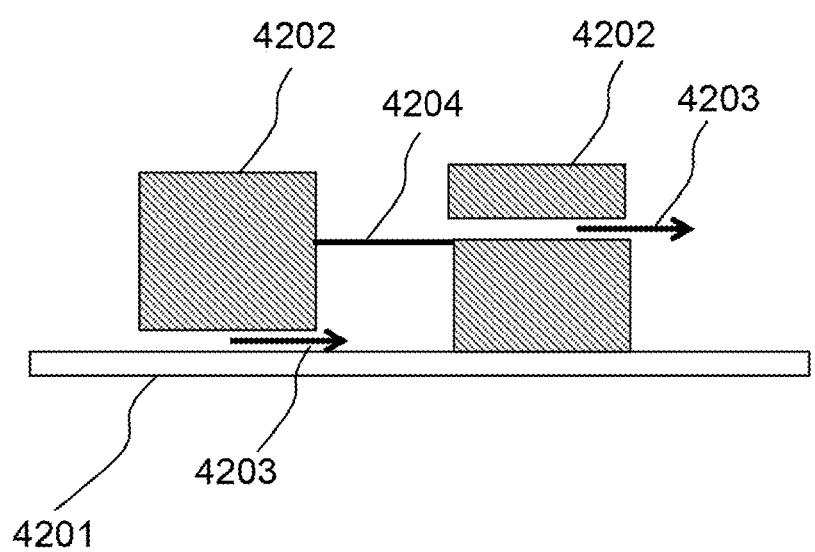
FIG. 44 is a diagram schematically showing a cross-section of the measuring cell culture plate.

FIG. 43 shows schematic diagrams and photographs of an example of a configuration of a measurement chamber of a cell culture system for measuring cardiac toxicity of the present invention. The cell culture vessel 4202 on which an introducing mechanism and a draining mechanism of the culture liquid is arranged has been adhered to the multi-electrode substrate 4201 on which a plurality of membrane potential measurement electrodes are arranged (see FIG. 44), forming a cell-culture-measurement plate capable of measuring 8 samples at the same time. As shown in FIG. 44 in which a cross-sectional view of a cell culture measurement plate is schematically shown, in the cell culture vessel 4202, the inlet of the solution is arranged in a fan-shaped form spread in the bottom surface closest to the multi-electrode substrate 4201, while the liquid draining mechanism has been deployed in a fan shape in the same direction as the direction of the interface of the liquid surface at a position that determines the height of the liquid surface 4204 at the top.

Figure 45:
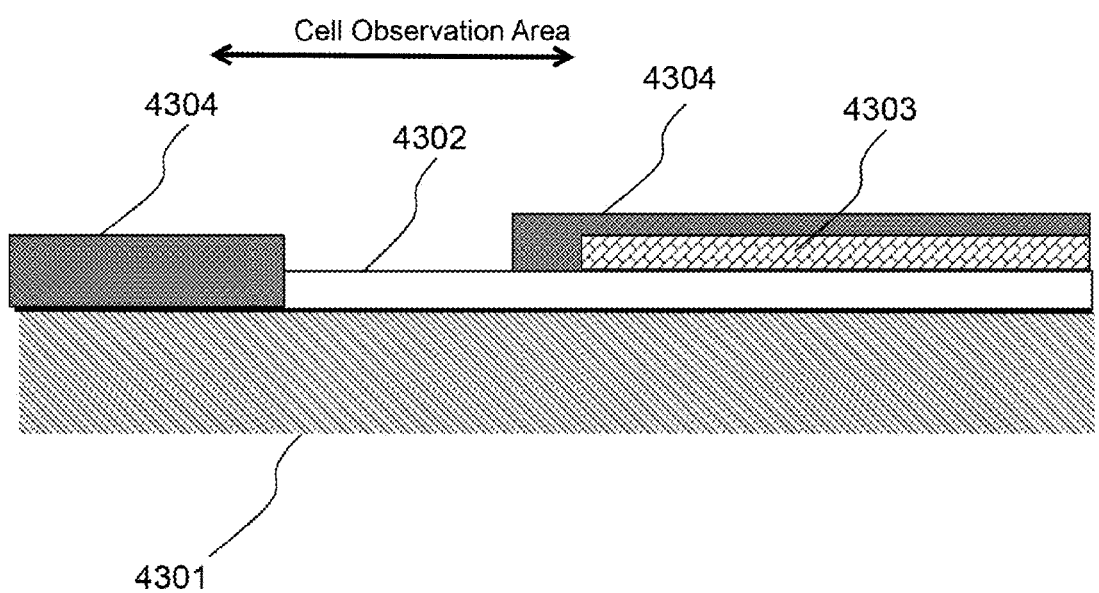
FIG. 45 is a diagram schematically illustrating a configuration of the electrode wire electrode arrangement being disposed in a multi-electrode substrate.

FIG. 45 is a diagram schematically illustrating a configuration of electrode wires of the electrode arrangement arranged in a multi-electrode substrate. In the present invention, in order to observe the shape of the cell, transparent electrodes such as ITO electrodes are used. However, an increase in the length of the wiring will results in a high resistance compared to normal metal electrodes due to their characteristics as a transparent electrode, and as a result the impedance becomes very large especially for a large plate such as the multi-electrode substrate. In order to avoid this problem, a metal layer may be disposed in the same arrangement as the transparent electrode to reduce the resistance value owing to the conductivity of the metal electrode. In fact, in the area for culturing the cells, a wiring using a transparent electrode 4302 on a glass substrate 4301 is disposed in order to perform an optical observation, while in an area not used for observing cells, a metal layer 4303 is disposed thereon to overlap the transparent electrode and the upper surface of which is coated with an insulating film. The metal electrode materials as used herein may be, for example, gold, platinum, titanium, copper, aluminum, and the like.

Figure 12:
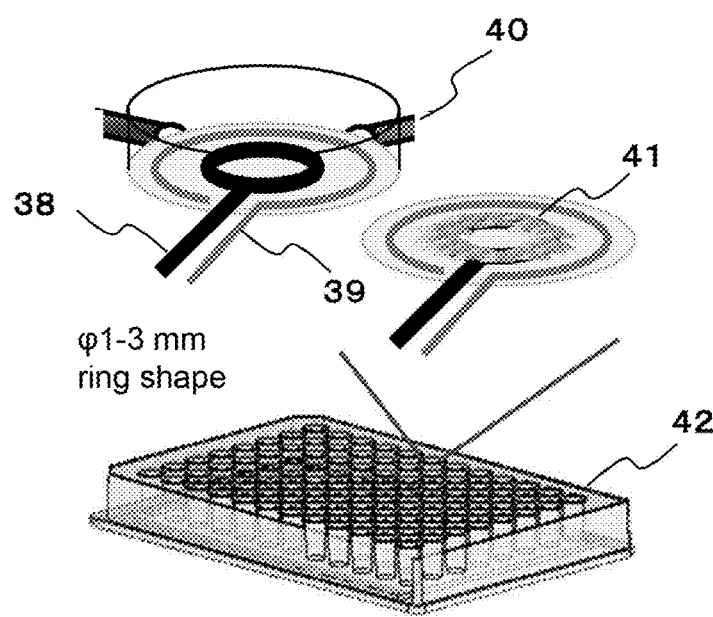
FIG. 12(a) is a schematic view showing an exemplary re-entry circuit measurement apparatus using an annular electrode.
FIG. 12(b) is a graph showing normal pulse data and abnormal pulse data actually measured with the electrode.
Figure 12:
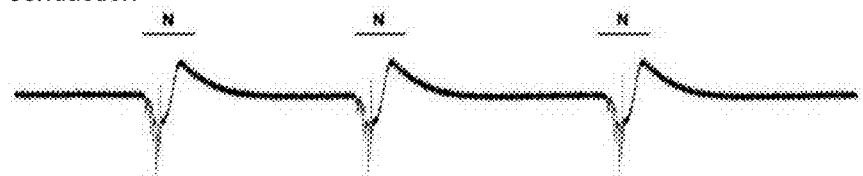
Figure 12:
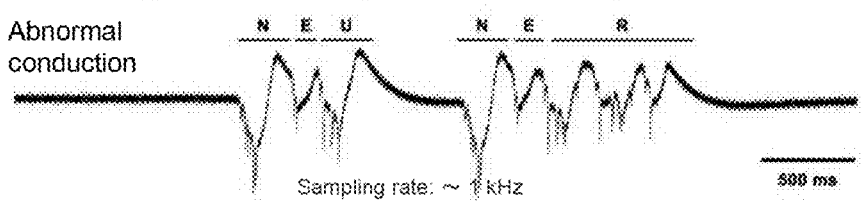
Figure 46:
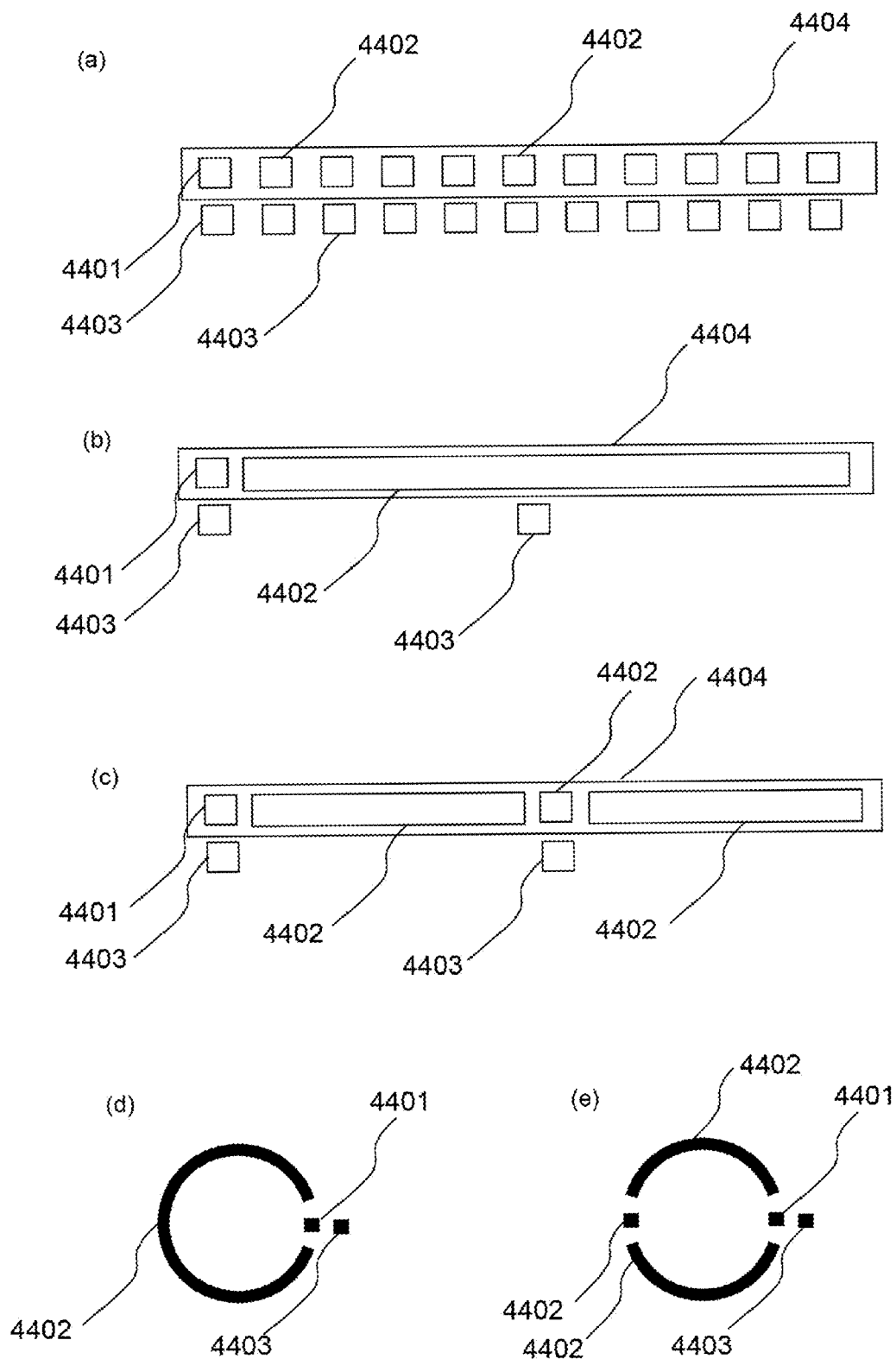
FIG. 46 is a schematic diagram showing an example of a multi-electrode arrangement of electrodes on the substrate.

FIG. 46 is a schematic diagram showing an example of electrode arrangement disposed on a multi-electrode substrate. First, in FIG. 46(a), there are arranged a stimulating electrode 4401 to locally stimulate the end of the myocardial cardiomyocyte network arranged in series in a cell culture area 4404, measuring electrodes 4402 for measuring the excitation conduction of cardiomyocytes stimulated by stimulation electrodes and a reference electrode 4403 for noise reduction. It is possible to measure the results of a plurality of local responses of a cardiomyocyte network obtained from each of the measurement electrodes 4402, and a fluctuation of the transmission rate can be determined by a comparative analysis of the degree of the transmission rate between the measurement electrodes. In FIG. 46 (b), there is shown a configuration where the measurement electrodes are connected in a straight line. By this configuration, it is possible to measure the waveform similar to the waveform of an electrocardiogram of the ST area (ventricular area) of the electrocardiogram. In FIG. 46 (c), there is shown a configuration that facilitates acquisition of the FP waveform of a local point of cardiomyocytes by separating a part of FIG. 46(b). FIG. 46 (d) is an example of an electrode arrangement for measuring cells arranged in a ring form on a ring-shaped electrode. Although these are intended to measure the cardiomyocyte network arranged in a ring shape as shown in FIG. 11 and FIG. 12, they differ in that a part of the ring-shaped measurement electrode is cut out, and a stimulating electrode for providing local forced stimulations is arranged therein, and a reference electrode is arranged for noise reduction. Further, in FIG. 46 (e), there is shown a configuration in which the measurement electrodes are split and it is possible to measure responses of a local portion of the cardiomyocytes.

INDUSTRIAL APPLICABILITY

According to the present invention, it is made possible to evaluate whether cardiomyocytes obtained through differentiation of stem cells, such as iPS cells, are healthy cardiomyocytes that can be used for agent screening or regenerative medicine for cardiomyocytes.

DESCRIPTION OF REFERENCE NUMERALS

1: transparent substrate, 2: microelectrode, 2c: reference electrode, 2': lead wire of microelectrode 2, $3_1, 3_2, 3_3, 3_4$: a wall by agarose gel, $4_1, 4_2, 4_3$ and $4_4$: gap, 7: peripheral surrounding wall, $8_1, 8_2, 8_3$: pipe, PC: personal computer, Ms: operation signal of PC, 10, $10_1, 10_2, 10_3, ---, 10_n$: cardiomyocytes or fibroblasts, 15: transparent stage of an optical observation device, 16: X-Y drive unit, 18: Z drive unit, $CH_1, CH_2, CH_3, CH_n$: cell holding unit, CCC: cell communication channel, $10_G$: cell population, $11_a$: barrier, $11_b$: opening, 19, 191,192,193: dichroic mirror, 20, 201: a band-pass filter, 21, 211: camera, 22: light source, 221: fluorescent light source, 23,231: band-pass filter, 24,241: shutter, 25: condenser lens, 26: objective lens, 27: movable electrode, 28: ground electrode, 29, 291: switching circuit, 30, 301: electrical signal measuring circuit, 31,311: electrical stimulation circuit, 32: cardiomyocytes, 33: fibroblasts, 34: pipette for cell placement, 35: N-th round transmission pathway, 36: (N+1)th round transmission pathway, 37: (N+2)th round transmission pathway, 38: measuring electrode, 39: reference electrode, 40: liquid sending system, 41: cell population arranged in a ring shape, 42: 96-well plate, 43: photo-sensitive element of a camera, 44: cell, 45: cell stimulation electrode, 100: cardiotoxicity testing apparatus, 3000: cardiotoxicity testing apparatus, 3001: measurement unit, 3002: PC interface, 3003: analog-to-digital converter, 3004: amplifier, 4201: multi-electrode substrate, 4202: cell culture vessel, 4203: flow of a solution, 4204: liquid level, 4301: glass substrate, 4302: transparent electrode, 4303: metal layer, 4304: insulating film, 4401: stimulating electrode, 4402: measurement electrodes, 4403: reference electrode, 4404: cell culturing area.

The invention claimed is:

1. A cardiotoxicity testing apparatus, comprising:
   a transparent substrate;
   an area surrounded by a wall formed on the transparent substrate, wherein the area is filled with a liquid cell culture medium;
   a cell population comprising a plurality of stably pulsating cardiomyocytes which are disposed in the area that is filled with the cell culture medium;
   a microelectrode provided in the area that is filled with the cell culture medium, wherein a cardiomyocyte of the cell population or a local portion of the cell population is placed on the microelectrode;
   a reference electrode provided in the area that is filled with the cell culture medium;
   an electrical potential measuring means for measuring the electrical potential of the cardiomyocyte placed on the microelectrode, comprising lead wires which are connected respectively to each of the microelectrode and a lead wire which is connected to the reference electrode;
   a recording means for recording data of the electrical potential of the cardiomyocytes before and after addition of a test agent measured by the electrical potential measuring means; and
   a control means for controlling the measuring means and the recording means to calculate the magnitude of variation in an elapsed time between a peak position of sodium-ion inflow into the cell and a peak position of potassium-ion outflow from the cell in a field potential waveform of the pulsation of cardiomyocytes (field potential duration) (FPD) by comparison of temporally adjacent pulsation signals, wherein the magnitude of the variation of the FPD is the short-term variability (STV) or the long-term variability (LTV) of the FPD.

2. The cardiotoxicity testing apparatus according to claim 1, wherein the control means is configured to calculate the FPD and the magnitude of the variation of the FPD, and to use as an index a combination of the FPD and the magnitude of the variation of the FPD that were calculated.

3. The cardiotoxicity testing apparatus according to claim 1, wherein the magnitude of the variation of the FPD is the short-term variability (STV) of the FPD.

4. The cardiotoxicity testing apparatus according to claim 1, wherein the cell population comprising the stably pulsating cardiomyocytes comprises a cellular network comprising a plurality of cardiomyocytes and fibroblasts that are capable of transmitting the pulsation.

5. The cardiotoxicity testing apparatus according to claim 1, which is configured to enable provision of at least one microelectrode on which the cell is placed with a stimulus for forced pulsation at regular intervals, wherein the microelectrode is for placing a cell containing a stably pulsating cardiomyocyte.

6. A cardiotoxicity testing method, comprising:
   measuring the magnitude of fluctuation of a waveform of the field potential of pulsating cardiomyocytes by comparison of adjacent pulsation signals; and
   examining the toxicity of an agent that acts on cardiomyocytes by assessing whether or not the rate at which the pulsation produced by the population of the cardiomyocytes propagates in the cellular network area is delayed when the agent acting on the cells is added to the culture medium using the cardiotoxicity testing apparatus according to claim 1.

7. A cardiotoxicity testing method, comprising:
   measuring the magnitude of fluctuation of a waveform of the field potential of pulsating cardiomyocytes by comparison of adjacent pulsation signals; and
   examining the toxicity of an agent that acts on cardiomyocytes by assessing whether or not the rate at which the pulsation produced by the population of the cardiomyocytes propagates in the cellular network area is delayed when the agent acting on the cells is added to the culture medium using the cardiotoxicity testing apparatus according to claim 1,
   the method further comprising at least one of the following steps:
   (i) providing a forced pulsatile stimulation at regular intervals to a cell, wherein the cell is placed on at least one microelectrodes for placing the cells of the cellular network;
   (ii) measuring the magnitude of the fluctuations of the field potential waveform of cardiopulsation collected from each microelectrode on which the cell is placed by comparison of the adjacent pulsation signals;
   (iii) measuring the magnitude of the variation of the elapsed time (field potential duration) between the peak position of the outflow of potassium ions from the cell and the peak position of the outflow of sodium ions from the cell by comparison of the adjacent pulsation signals in the waveform of the field potential;
   (iv) measuring the magnitude of the fluctuations of the field potential waveform of cardiopulsation collected from each microelectrode on which the cell is placed by comparing between the adjacent pulsation signals the fluctuation of time or the speed of transmission of the pulsation from the area in which the pulsation of the cell of the cellular network generates to the observation electrode;
(v) measuring the membrane potential by differentiating each field potential waveform of cardiopulsation collected from each microelectrode on which the cells is placed;
(vi) measuring the degree of disturbance of the transmission of the pulsation of the entire cell population to be compared to the electrocardiogram data by overlapping the field potential waveforms of the pulsating cardiomyocytes collected from each electrode on which the cell is placed to generate a composite field potential waveform;
(vii) analyzing the amount of current supplied by an electric control mechanism using a feedback control mechanism to maintain a constant potential of the microelectrode on which the cell is placed; and
(viii) starting measurements after at least 30 seconds from the start of the periodic forced pulsatile stimulation on the cell.

8. The method according to claim 7, wherein the magnitude of the variation of the FPD is the short-term variability (STV) in FPD.

9. A cardiotoxicity testing apparatus, comprising:
a transparent substrate;
a pacemaker area comprising a cell population including a plurality of stably pulsating cardiomyocytes placed on the transparent substrate;
a cellular network comprising a plurality of cardiomyocytes and fibroblasts that are arranged in series, disposed on the transparent substrate and transmit the pulsation in conjunction with the cell population;
a wall formed on the transparent substrate to surround the periphery of the cell population and the cellular network and to fill a cell culture medium;
a culture-medium supply/drain channel for supplying and/or draining the cell culture medium to and/or from the area surrounded by the wall;
an agent delivery channel for introducing an agent acting on the cells to the cell culture medium;
a microelectrode on which a single cell of the cell population or a local portion of the cell population is placed;
microelectrodes on which each individual cell of the cellular network is respectively placed;
a reference electrode provided in the area which is filled with the cell culture medium and is surrounded by the wall;
a potential-measuring means for measuring a membrane potential of the cell that is placed on the microelectrode using lead wires which are connected respectively to each of the microelectrodes and a lead wire which is connected to the reference electrode; and
a control/recording means for controlling an electrical stimulation delivered to the microelectrode and recording data of the potential measured by the potential measuring means, wherein the control/recording means control the potential-measuring means to calculate the magnitude of variation in an elapsed time between a peak position of sodium-ion inflow into the cell and a peak position of potassium-ion outflow from the cell in a field potential waveform of the pulsation of cardiomyocytes (field potential duration) (FPD) by comparison of temporally adjacent pulsation signals, wherein the magnitude of the variation of the FPD is the short-term variability (STV) or the long-term variability (LTV) of the FPD.

10. The cardiotoxicity testing apparatus according to claim 9, comprising an electrode for providing a stimulus locally at an end point of the cellular network in which cells are arranged in series.

11. The cardiotoxicity testing apparatus according to claim 9, wherein the cellular network is arranged in a ring shape, and wherein a portion of the ring is cutout and an electrode for locally providing a stimulus is located at the cutout point.

12. The cardiotoxicity testing apparatus according to claim 9, wherein the control/recording means is configured to measure the magnitude of the fluctuation of the waveform of the field potential of the cardiopulsation collected from each of the microelectrodes on which each of the cells is placed by comparing between the adjacent pulsations the fluctuations of transmission time or transmission speed of the pulsation of the cells of the cellular network from the area where the pulsation of the cell is generated to the observation electrode.

13. The cardiotoxicity testing apparatus according to claim 9, comprising a temperature control mechanism to maintain the cardiomyocytes at an appropriate temperature.

14. The cardiotoxicity testing apparatus according to claim 9, wherein the microelectrodes constitute a multi-electrode array consisting of a plurality of microelectrodes.

15. A cardiotoxicity testing method, comprising steps of:
preparing a cell population containing a plurality of stably pulsating cardiomyocytes;
culturing the cell population in a culture vessel, wherein a multi-electrode array is disposed on the bottom surface of the culture vessel;
adding a subject agent to the cell population being cultured to measure a membrane potential of the culture cell population using a multi-electrode array, wherein the membrane potential of the culture cell population is measured and data of the membrane potential is acquired before and after the addition of the agent;
measuring the magnitude of fluctuation of a waveform of the field potential of pulsating cardiomyocytes by comparison of adjacent pulsation signals; and
calculating an elapsed time from a peak inflow of sodium ions into the cell to a peak outflow of potassium ions from the cell (field potential duration) (FPD) and the magnitude of the variation of the FPD of the waveform of the field potential (FP) based on the data of the membrane potential acquired to assess the cardiotoxicity of the agent using as an index a combination of the calculated FPD and the magnitude of the variation of the FPD, wherein the magnitude of the variation of the FPD is the short-term variability (STV) or the long-term variability (LTV) of the FPD.

16. The method according to claim 15, wherein the magnitude of the variation of the FPD is the short-term variability (STV) in FPD.

* * * * *